United States Patent
Stankova et al.

(10) Patent No.: US 9,957,294 B2
(45) Date of Patent: May 1, 2018

(54) COMPOSITIONS AND METHODS FOR ANALYZING HISTIDINE PHOSPHORYLATION

(71) Applicants: Salk Institute for Biological Studies, La Jolla, CA (US); Sanofi, Paris (FR)

(72) Inventors: Magda Stankova, Tucson, AZ (US); Fahad Al-Obeidi, Tucson, AZ (US); Jacques Mauger, Oro Valley, AZ (US); Robert A. Binnie, Tucson, AZ (US); Tony Hunter, Del Mar, CA (US); Jill Meisenhelder, Vista, CA (US); Stephen Rush Fuhs, San Diego, CA (US)

(73) Assignees: Salk Institute for Biological Studies, La Jolla, CA (US); Sanofi, Paris (FR)

( * ) Notice: Subject to any disclaimer, the term of this patent is extended or adjusted under 35 U.S.C. 154(b) by 813 days.

(21) Appl. No.: 14/485,578

(22) Filed: Sep. 12, 2014

(65) Prior Publication Data
US 2015/0004173 A1    Jan. 1, 2015

Related U.S. Application Data

(63) Continuation of application No. PCT/US2013/030917, filed on Mar. 13, 2013.

(60) Provisional application No. 61/641,607, filed on May 2, 2012, provisional application No. 61/610,180, filed on Mar. 13, 2012.

(51) Int. Cl.
| | |
|---|---|
| *C07K 16/40* | (2006.01) |
| *C07K 17/08* | (2006.01) |
| *C07K 7/06* | (2006.01) |
| *C07K 7/08* | (2006.01) |
| *G01N 33/68* | (2006.01) |
| *C07K 16/44* | (2006.01) |
| *G01N 33/573* | (2006.01) |

(52) U.S. Cl.
CPC ............ *C07K 7/06* (2013.01); *C07K 7/08* (2013.01); *C07K 16/40* (2013.01); *C07K 16/44* (2013.01); *C07K 17/08* (2013.01); *G01N 33/573* (2013.01); *G01N 33/6812* (2013.01); *C07K 2317/33* (2013.01); *C07K 2317/34* (2013.01); *G01N 2333/9123* (2013.01)

(58) Field of Classification Search
None
See application file for complete search history.

(56) References Cited

U.S. PATENT DOCUMENTS

| | | | | |
|---|---|---|---|---|
| 9,035,068 B2* | 5/2015 | Muir | ............ | A61K 31/675 548/255 |
| 2002/0065225 A1* | 5/2002 | Muimo | ............ | C07K 14/4712 435/7.23 |

FOREIGN PATENT DOCUMENTS

WO    WO 2012/040523    3/2012

OTHER PUBLICATIONS

Campbell (Monoclonal Antibody Technology, 1984, Chapter 1, pp. 1-32).*
International Search Report from patent PCT Application No. PCT/US2013/030917, 5 pages, (dated Jul. 2, 2013).
Kee and Muir, "Chasing phosphohistidine, an elusive sibling in the phosphoamino acid family," *ACS Chem. Biol.* 7(1): 44-51 (Jan. 20, 2012).
Kee et al., "A pan-specific antibody for direct detection of protein histidine phosphorylation," *Nature Chem. Biol.* 9(7):416-421 (Jul. 2013).
Kee et al., "Development of stable phosphohistidine analogues," *J. Am. Chem. Soc.* 132:14327-14329 (Sep. 9, 2010).
McAllister et al., "Fmoc-chemistry of a stable phosphohistidine analogue," *Chem. Commun.* 47:1297-1299 (2011).
Mukai et al., "Stable triazolylphosphonate analogues of phosphohistidine," *Amino Acids* 43:857-874 (Nov. 22, 2011).
Written Opinion from patent PCT Application No. PCT/US2013/030917, 5 pages, dated Jul. 2, 2013.

* cited by examiner

*Primary Examiner* — Sharon X Wen
(74) *Attorney, Agent, or Firm* — Klarquist Sparkman, LLP

(57) ABSTRACT

A peptide is disclosed of the general structure: Z—W—Y, wherein Z and Y are independently a one to eight amino acid sequence wherein the amino acids are selected from glycine and alanine and W is a non-hydrolyzable pHis analogue. Such peptides can be used to produce sequence-independent anti-phosphohistidine antibodies. Also provided are antibodies that specifically bind to a peptide comprising a phosphohistidine (or a non-hydrolyzable pHis analogue) but fail to specifically bind to an identical peptide containing histidine instead of phosphohistidine.

17 Claims, 23 Drawing Sheets

Histidine 1-pTza

R = H, CH₃
3-pTza

Fig. 3

```
1    MANLERTFIAIKPDGVQRGLVGEIIKRFEQKGFRLVAMKFLRASEEHLKQHYIDLKDRPF    60    Nm23-H2_HUMAN
1    MANLERTFIAIKPDGVQRGLVGEIIKRFEQKGFRLVAMKFLRASEEHLKQHYIDLKDRPF    60    Nm23-H2_MOUSE
1    MANCERTFIAIKPDGVQRGLVGEIIKRFEQKGFRLVGLKFMQASEDLLKEHYVDLKDRPF    60    Nm23-H1_HUMAN
1    MANSERTFIAIKPDGVQRGLVGEIIKRFEQKGFRLVGLKFLQASEDLLREHYTDLKDRPF    60    Nm23-H1_MOUSE
     ***.**********************************:**:;***: **:** ******

61   FPGLVKYMNSGPVVAMVWEGLNVVKTGRVMLGETNPADSKPGTIRGDFCIQVGRNIIHGS   120    Nm23-H2_HUMAN
61   FPGLVKYMNSGPVVAMVWEGLNVVKTGRVMLGETNPADSKPGTIRGDFCIQVGRNIIHGS   120    Nm23-H2_MOUSE
61   FRGLVKYMQSGPVVAMVWEGLNVVKTGRVMLGETNPADSKPGTIRGDFCIQVGRNIIHGS   120    Nm23-H1_HUMAN
61   FTGLVKYMHSGPVVAMVWEGLNVVKTGRVMLGETNPADSKPGTIRGDFCIQVGRNIIHGS   120    Nm23-H1_MOUSE
     *.*****:*****************************************************

121  DSVKSAEKEISLWFKPEELVDYKSCAHDWVYE    152    NME2_HUMAN
121  DSVESAEKEIHLWFKPEELIDYKSCAHDWVYE    152    NME2_MOUSE
121  DSVESAEKEIGLWFHPEELVDYTSCAQNWIYE    152    NME1_HUMAN
121  DSVKSAEKEISLWFQPEELVEYKSCAQNWIYE    152    NME1_MOUSE
     ***;******  ***;****::*.***::*:**
```

COMPOSITIONS AND METHODS FOR ANALYZING HISTIDINE PHOSPHORYLATION

CROSS REFERENCE TO RELATED APPLICATIONS

This is a continuation of International Application No. PCT/US2013/030917, filed Mar. 13, 2013, which claims the benefit of U.S. Provisional Application No. 61/610,180, filed on Mar. 13, 2012, and U.S. Provisional Application No. 61/641,607, filed on May 2, 2012. The disclosure of the prior applications is hereby expressly incorporated by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: one 75,000 byte ASCII (text) file named "7158-91474-04_Sequence_Listing.txt, 73.7 KB," created on Sep. 11, 2014.

BACKGROUND

Protein phosphorylation regulates virtually all cellular processes and aberrant phosphorylation is the underlying cause of numerous cancers. The majority of intracellular proteins are phosphorylated at any given time, and, while 9 of the 20 amino acids can be phosphorylated, Ser, Thr, and Tyr phosphorylation has attracted the majority of attention in eukaryotic organisms. Histidine (His) phosphorylation has long been implicated in signal transduction (e.g. prokaryotic "two-component" systems); however, its role in mammalian cells remains largely unexplored. This is due to the difficulty in studying His phosphorylation by standard biochemical techniques.

Unlike pTyr, pSer and pThr, phosphohistidine (pHis) is heat and acid labile. Consequently, the importance of His phosphorylation has been greatly underestimated. Despite the brief half-life of pHis under acidic conditions (18-25 sec half-life in 1 M HCl, 49° C.), the high-energy, phosphoramidate bond of pHis is stabilized by basic conditions, and the half-life in protein substrates is strongly influenced by neighboring amino acid residues indicating it is highly context dependent (12 day half-life of histone H4 at RT, pH 7.6). Thus, new tools are needed to bring this under-appreciated post-translational modification to light.

Despite the paucity of knowledge about His phosphorylation in eukaryotic signal transduction, there is growing evidence implicating His kinases in cancer and tumor metastasis. In fact, the first metastasis suppressor gene identified (by its reduced expression in highly metastatic melanoma cell lines) is one of only two known mammalian His kinases; Nm23-H1 (AKA NME1 or nucleoside diphosphate kinase [NDPK-A]). Nm23 family members are involved in intracellular nucleotide homeostasis as well as in both physiological and pathophysiological cellular processes such as proliferation, differentiation, development, apoptosis, cytokinesis and metastasis, through mechanisms that remain largely unknown.

Nm23-H1 and the closely related Nm23-H2 (NME2/NDPK-B) catalyze transfer of phosphate from ATP onto nucleoside diphosphates (NDPs) through a pHis enzyme intermediate. Nm23-H1/-H2 also possess His kinase activity, transferring the phosphate from the active site pHis onto a His in a target protein. However, the lack of pHis-specific antibodies (Abs) and pHis's instability under typical conditions used for proteomics have made it difficult to study the role His phosphorylation plays in suppression of metastasis. Phosphospecific Abs exist for pSer, pThr and pTyr, and these, combined with biochemical and proteomic techniques, have proved invaluable in the study of protein phosphorylation in cellular signaling and cancer. Until recently, the difficulties in creating stable pHis peptides have precluded generation of pHis specific Abs. Development of non-cleavable pHis analogues now makes this possible [Kee et al., (2010) J Am Chem Soc. 132, 14327-9 and McAllister et al., (2011) Chem Commun. 47, 1297-9]. These pHis analogues will be used as immunogens to make Abs specific for both biologically relevant pHis isomers, 1- and 3-pHis (FIG. 1). Anti-1- and 3-pHis Abs will serve as novel tools to study His kinase activity of Nm23 proteins as well as yet undiscovered His kinases and their substrates.

It has been estimated that 6% of phosphorylation in eukaryotes occurs on His and that pHis could be 10-100 times more abundant than pTyr. Despite this, only a handful of mammalian pHis proteins, two His kinases (Nm23-H1/-H2) and a single pHis phosphatase (PHPT1) have been identified. For the few known pHis substrates, this phosphorylation has proved essential to their function and revealed novel signaling pathways. Nm23-H2 phosphorylates KCa3.1 (H358) and is required for potassium channel activation. Phosphorylation of heterotrimeric Gs protein subunit β1 (H266) by Nm23-H2 activates Gs and regulates basal cAMP accumulation. Furthermore, Nm23-H2, G proteins and caveolin expression are mutually dependent for stable localization and caveolae formation. Histone H4 phosphorylation (H18) is associated with enhanced cell proliferation in liver and thymus. The development of pHis-specific Abs combined with improved techniques for pHis peptide enrichment and identification by MS will be used to greatly expand the number of known pHis targets and determine which ones play a role in suppression of tumor metastasis by His kinases. In addition, this protocol may identify novel His kinases, since known His kinases autophosphorylate on His.

SUMMARY

As disclosed herein peptides are provided that comprise non-hydrolyzable phosphohistidine analogues, 1-pTza & 3-pTza, for use as immunogens (see FIG. 1). Such peptides, comprised only of immunogenically neutral amino acids with small side chains (e.g., alanine and glycine) and a non-hydrolyzable phosphohistidine analogue, are used in generating antibodies that bind to proteins that comprise a phosphohistidine, but fail to bind to proteins of identical sequence wherein the histidine residue is not phosphorylated. In one aspect of the present disclosure, peptides comprising a library of random sequences (Lam, K. et. al., (1991) Nature, 354, 82-4) of immunogenically neutral amino acids with short side chains (e.g., alanine and glycine) in addition to one of the two non-hydrolyzable pHis analogues are used to generate sequence-independent anti-pHis Abs.

The present disclosure is also directed to methods of generating sequence-independent anti-pHis antibodies as well as the sequence-independent anti-phosphohistidine (pHis) specific poly- and monoclonal anti-phosphohistidine (pHis) antibodies themselves and hybridoma cell lines expressing such antibodies. In accordance with one embodiment an antibody is provided that specifically binds to a peptide or protein comprising a phosphorylated histidine, independent of amino acid sequence, but does not specifically bind to a peptide of identical sequence lacking a phosphorylated histidine. The antibody can be either a polyclonal or monoclonal antibody. Hybridoma cell lines and procaryotic cells producing such antibodies in a recombinant form are also encompassed by the present invention.

The present invention is also directed to a method of identifying proteins comprising a phosphorylated histidine, comprising the steps of contacting a sample comprising a protein with the sequence-independent anti-phosphohistidine (pHis) specific poly- or monoclonal anti-phosphohistidine (pHis) antibodies disclosed herein.

BRIEF DESCRIPTION OF THE DRAWINGS

FIG. 3. Amino acid sequence alignment of the histidine kinases Nm23-H1 and Nm23-H2. Human Nm23-H1 (SEQ ID NO: 13) and Nm23-H2 (SEQ ID NO: 11) proteins are 88% identical. Mouse Nm23-H1 (SEQ ID NO: 14) is 98% identical to human Nm23-H1 (SEQ ID NO: 13); and mouse Nm23-H2 (SEQ ID NO: 12) is 94% identical to human Nm23-H2. Non-conserved residues are highlighted in grey. The catalytic, autophosphorylation site at H118 is indicated in bold letter. Nm23-H1 and -H2 autophosphorylate themselves on the catalytic His residue (H118). The kinases themselves can therefore serve as positive and negative controls for testing the specificity of the rabbit antisera in applications such as immunoblotting and immunoprecipitation.

FIG. 6A shows the results of anti-1-pTza antisera to detect in vitro Nm23 autophosphorylation. Lane 1 indicates a doublet that is not present in lane 3 (the negative control where Nm23 phosphorylation was conducted in the absence of ATP). FIG. 6B shows the results of anti-3-pTza antisera to detect in vitro Nm23 autophosphorylation. Only backround/non-specific binding was detected.

FIGS. 8A & 8B show the coomassie detection limit vs. the anti-1-pTza antisera detection limit, respectively for rNm23-H1 autophosphorylation. The coomassie limit of detection was approximately 25-50 ng, whereas the anti-1-pTza antisera detection limit was 5 to 10 times higher. Specifically, bleed 3 is approximately 5-10-fold higher titer than bleed 2 and 7305-4 has 2 fold higher titer than 7305-3. 7306-4 only showed non-specific binding (despite a positive result in 1-pTza peptide dot blots). FIG. 8C shows the titer levels continue to increase in the fourth bleed of 7306 and 7305 rabbits. FIG. 8D shows that a polyclonal antibody against Nm23 that detects both phosphorylated & unmodified Nm23-H1 detects both bands on a western blot. FIG. 8E compares the titer of bleed 4 vs. bleed 5 for detecting rNm23-H1 autophosphorylation using 7305 anti-sera with the 5th bleed approximately two fold higher than the 4th bleed.

As shown in FIG. 9B, 7305-5 anti-serum can detect pFLAG-Nm23-H1.

FIG. 10A shows the results of anti-1-pHis antibodies recovered from four multiclones identified by 1-pTza peptide ELISA used to probe a western blot of pGEX-Nm23-H1 transformed E. coli lysates. Lysates were loaded with or without first being incubated at 95° C. The results show that the multiclonal anti-1-pHis antibodies (with 7 being an example of a 1-pTza ELISA positive, but pHis negative multiclone) bound to the autophosphorylated Nm23-H1 protein, and that binding was heat sensitive. Three hybridoma multiclones from rabbit 7305 were subsequently selected for subcloning and generation of monoclonal hybridoma cell lines. FIG. 10B shows data from a subset of four such subclones derived from multiclones 1, 50 and 77. As in FIG. 10A, lysates from pGEX-Nm23-H1 transformed E. coli were loaded with or without first being incubated at 95° C. Each of the subclones could specifically bind histidine phosphorylated Nm23-H1, as well as other histidine-phosphorylated proteins present in the E. coli lysate.

FIG. 12A is an initial screen of subclones (8-1 to 8-11) and FIG. 12B is a rescan of the positive 7303 subclones identified in FIG. 12A, wherein the image was optimized to more clearly show the weak signal for phospho-PGAM. Lane 1 was treated with acid and heat, and so no phosphohistidines should be present; lanes 2 and 3 represent different concentrations of in vitro autophosphorylated PGAM (25 and 500 ng, respectively). Positive controls using polyclonal antibodies from the 11th bleed of the rabbit 7303 (7303-11) and affinity-purified 3-pHis antibodies show binding to the autophosphorylated PGAM at both concentrations. 7 of 12 subclones produced a weak signal for phospho-PGAM 500 ng.

DETAILED DESCRIPTION

Definitions

Figure 1:
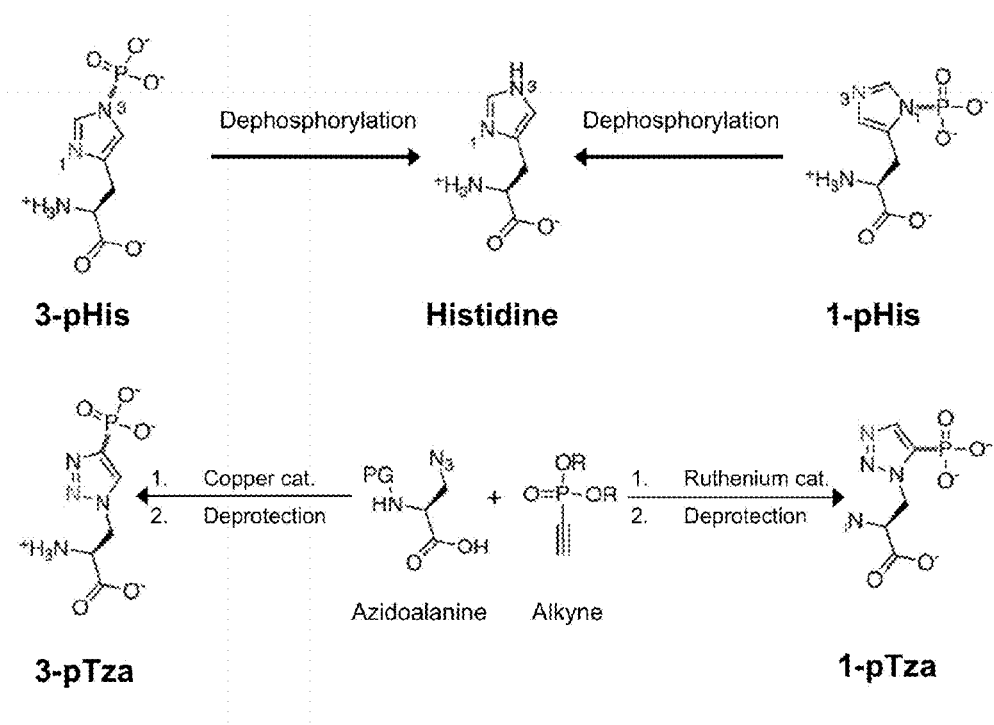
FIG. 1. Non-hydrolyzable pHis analogues: 3-pTza and 1-pTza. Structures of phosphohistidine isomers; 3- and 1-phosphohistidine (3-pHis and 1-pHis) are shown in FIG. 1. Non-hydrolyzable 3-pHis and 1-pHis analogues, 1-phosphoryltriazolylalanine (1-pTza) and 3-phosphoryltriazolylalanine (3-pTza), are synthesized via a "click chemistry" reaction between an azidoalanine and an alkyne. The same building blocks with different catalysts are used to make both isomers.
Figure 2A:
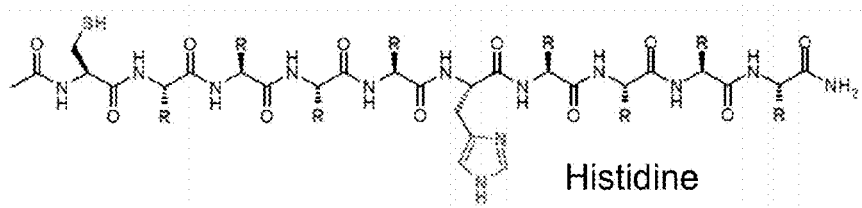
FIG. 2A-2C. Incorporation of the pHis analogues 1-pTza and 3-pTza into immunizing peptides. Three synthetic peptide libraries have been synthesized, consisting of either histidine or a non-hydrolyzable pHis analogue flanked by randomized, non-immunogenic amino acids (glycine [R=H] and alanine [R=CH3]), to promote generation of sequence-independent anti-pHis Abs. Each library is a complex mixture of peptides ($2^8$=256) that are acylated at the N-terminus and contain an N-terminal L-cysteine for coupling to a carrier protein such as keyhole limpet hemocyanin (KLH). A. The library incorporating histidine will be used for negative selection of Abs that recognize non-phosphorylated histidine. B. & C. The immunizing peptide libraries, one for each isomer, contain the non-hydrolyzable analogues, 1-pTza or 3-pTza.
Figure 2B:
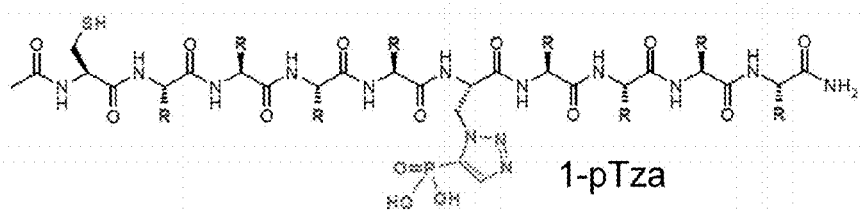
Figure 2C:
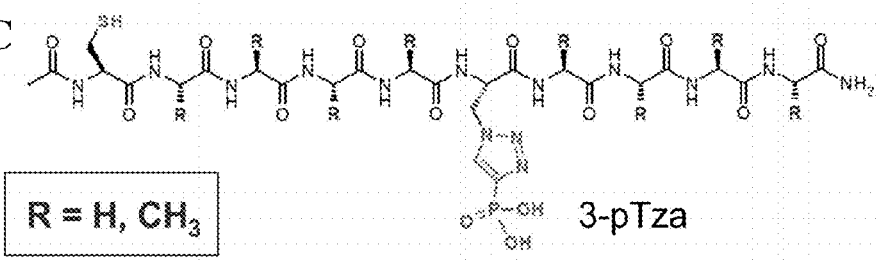

In describing and claiming the invention, the following terminology will be used in accordance with the definitions set forth below.

The term "about" as used herein means greater or lesser than the value or range of values stated by 10 percent, but is not intended to limit any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

The term "antibody" or "antibodies" as used herein refers to all types of immunoglobulins, including IgG, IgM, IgA, IgD, and IgE, including Fab or antigen-recognition fragments thereof. The antibodies may be monoclonal or polyclonal and may be of any species of origin, including (for example) mouse, rat, rabbit, goat, sheep, pig, chicken, horse, or human, or may be chimeric antibodies, or camelid (single chain) antibodies. See, e.g., M. Walker et al., Molec. Immunol. 26: 403-11 (1989); Morrison et al., Proc. Nat'l. Acad. Sci. 81: 6851 (1984); Neuberger et al., Nature 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.), or by recombining variable regions into expression vectors. The antibodies may also be chemically constructed according to the method disclosed in U.S. Pat. No. 4,676,980 (Segel et al.).

The term "specifically bind" means a special and precise interaction between two molecules which is dependent upon their structure, resulting in a high preference of binding between the two molecules relative to other molecules.

As used herein the term "patient" without further designation is intended to encompass any warm blooded vertebrate domesticated animal (including for example, but not limited to livestock, horses, cats, dogs and other pets) and humans.

In the present disclosure, a "chimeric antibody" refers to an antibody obtained by linking a variable region of an antibody of one species with a constant region of an antibody of another species. For example, such a chimeric antibody can be obtained as follows. A mouse is immunized with an antigen. A portion coding an antibody variable part (variable region) which binds to the antigen is cut out from a gene coding a monoclonal antibody of the mouse. The portion is linked with a gene coding a human bone marrow-derived antibody constant part (constant region). These linked genes are incorporated in an expression vector. The expression vector is then introduced into a host which produces a chimeric antibody (Refer to, for example, Japanese Unexamined Patent Application Publication No. Hei 8-280387, U.S. Pat. Nos. 4,816,397, 4,816,567, and 5,807, 715).

In the present disclosure, a "humanized antibody" refers to an antibody obtained by grafting a genome sequence of an antigen-binding site (CDR) of a non-human-derived antibody onto a gene of a human antibody (CDR grafting).

Preparation methods of such chimeric antibodies have been known (refer to, for example, EP239400, EP125023, WO90/07861, and WO96/02576). In the present invention, a "functional fragment" of an antibody means a part (a partial fragment) of an antibody, which retains a capability of specifically recognizing an antigen of the antibody from which the part is originated. Specific examples of the functional fragment include Fab, Fab', F(ab')2, a variable region fragment (Fv), a disulfide-linked Fv, a single-chain Fv (scFv), sc(Fv)2, a diabody, a polyspecific antibody, and polymers thereof.

Embodiments

Detailed Description

As disclosed herein a library of random peptide sequences is provided wherein each peptide sequence comprises an analog of phosphohistidine wherein the phosphate group is stably linked as a phosphonate to a carbon in the histidine analog. More particularly, two non-hydrolyzable phosphohistidine analogues, 1-pTza & 3-pTza, respectively (see FIG. 1), have been incorporated into synthetic peptides for use in generating antibodies specific for proteins that comprise a phosphohistidine. In one aspect of the present disclosure peptides comprised of only immunogenically neutral amino acids (e.g., alanine and glycine) and a non-hydrolyzable pHis analogue are used to promote generation of sequence-independent anti-pHis Abs. In one embodiment the non-hydrolyzable pHis analogue is 1-pTza or 3-pTza. In a further embodiment the peptide comprises an amino acid that is linked to a hapten carrier protein. In one embodiment the carrier protein is keyhole limpet hemocyanin. In a further embodiment the 1-pTza or 3-pTza containing peptide further comprises a lysine, tyrosine or cysteine amino acid having a carrier protein linked to this amino acid. In one embodiment the 1-pTza or 3-pTza containing peptide comprises a cysteine covalently linked to keyhole limpet hemocyanin through a disulfide bond formed with the cysteine side chain.

In accordance with one embodiment a peptide is provided with the general formula Z—W—Y, wherein Z and Y are amino acid sequences comprised of immunogenically neutral amino acids having short side chains, and independently ranging in length from about 2 to about 8 amino acids in length, and W is a non-hydrolyzable pHis analogue. In one embodiment the amino acids are either glycine or alanine; however, any amino acid (natural or synthetic) can be used that tends not to induce a specific immune response. In one embodiment the non-hydrolyzable pHis analogue is 1-pTza or 3-pTza. In one embodiment the peptide comprises an amino acid that can be used for covalent attachment of additional compounds including, for example, a carrier protein. In one embodiment an additional amino acid is added at the amino or carboxy terminus of the peptide of the formula Z—W—Y wherein the additional amino acid is cysteine, tyrosine or lysine. In one embodiment the peptide is further modified to include an amino (N)-terminal acylation, and/or a carboxy (C)-terminal amidation.

In one embodiment the peptide comprises the structure

Cys-Z—W—Y wherein

Z is a sequence selected from the group consisting of $X_1$, $X_1X_2$, $X_1X_2X_3$, $X_1X_2X_3X_4$ (SEQ ID NO: 1), $X_1X_2X_3X_4X_5$ (SEQ ID NO: 2), $X_1X_2X_3X_4X_5X_6$ (SEQ ID NO: 3), $X_1X_2X_3X_4X_5X_6X_7$ (SEQ ID NO: 4) and $X_1X_2X_3X_4X_5X_6X_7X_8$ (SEQ ID NO: 5);

W is an amino acid selected from

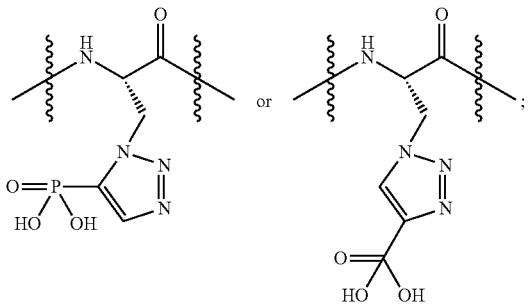

Y is a sequence selected from the group consisting of $X_{11}$, $X_{11}X_{12}$, $X_{11}X_{12}X_{13}$, $X_{11}X_{12}X_{13}X_{14}$ (SEQ ID NO: 6), $X_{11}X_{12}X_{13}X_{14}X_{15}$ (SEQ ID NO: 7), $X_{11}X_{12}X_{13}X_{14}X_{15}X_{16}$ (SEQ ID NO: 8), $X_{11}X_{12}X_{13}X_{14}X_{15}X_{16}X_{17}$ (SEQ ID NO: 9) and $X_{11}X_{12}X_{13}X_{14}X_{15}X_{16}X_{17}X_{18}$ (SEQ ID NO: 10);

wherein $X_1$, $X_2$, $X_3$, $X_4$, $X_5$, $X_6$, $X_7$, $X_8$, $X_{11}$, $X_{12}$, $X_{13}$, $X_{14}$, $X_{15}$, $X_{16}$, $X_{17}$ and $X_{18}$ are independently alanine or glycine. In one embodiment the N-terminal amine is acylated and the C-terminal carboxylic acid group is replaced with an amide. In another embodiment Z and Y are each independently 4 to 7 amino acid sequences. In one embodiment both Y and Z are four amino acids in length. In one embodiment one of the amino acids of Z or Y is substituted with an amino acid (e.g. histidine, tyrosine, lysine or cysteine) or such an amino acid is added to the N- or C-terminus of the peptide that allows for covalent attachment of additional moieties, such as carrier proteins. The peptide in some embodiment further comprises a carrier protein linked to the peptide, and in one embodiment the carrier protein is keyhole limpet hemocyanin covalently linked to the side chain of the cysteine of said peptide. In accordance with the present invention any carrier protein known to those skilled in the art can be used in accordance with the embodiment disclosed here.

In one embodiment a composition is provided comprising a plurality of peptides that differ in their primary sequence but conform to the general structure of Z—W—Y as defined herein. Such a composition is called a library. In one embodiment a library including at least 256 different peptides is provided wherein each of said 256 peptides has the structure Cys-Z—W—Y or Z—W—Y, wherein Z is a sequence selected from the group consisting of $X_1$, $X_1X_2$, $X_1X_2X_3$, $X_1X_2X_3X_4$ (SEQ ID NO: 1), $X_1X_2X_3X_4X_5$ (SEQ ID NO: 2), $X_1X_2X_3X_4X_5X_6$ (SEQ ID NO: 3), $X_1X_2X_3X_4X_5X_6X_7$ (SEQ ID NO: 4) and $X_1X_2X_3X_4X_5X_6X_7X_8$ (SEQ ID NO: 5);

W is an amino acid selected from

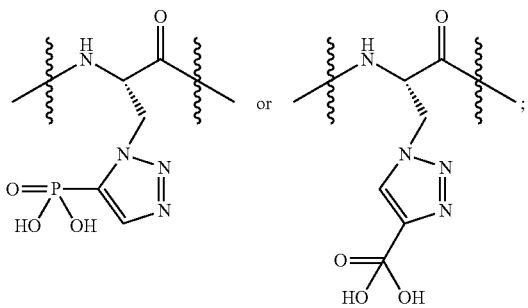

Y is a sequence selected from the group consisting of $X_{11}$, $X_{11}X_{12}$, $X_{11}X_{12}X_{13}$, $X_{11}X_{12}X_{13}X_{14}$ (SEQ ID NO: 6), $X_{11}X_{12}X_{13}X_{14}X_{15}$ (SEQ ID NO: 7), $X_{11}X_{12}X_{13}X_{14}X_{15}X_{16}$ (SEQ ID NO: 8), $X_{11}X_{12}X_{13}X_{14}X_{15}X_{16}X_{17}$ (SEQ ID NO: 9) and $X_{11}X_{12}X_{13}X_{14}X_{15}X_{16}X_{17}X_{18}$ (SEQ ID NO: 10); wherein $X_1$, $X_2$, $X_3$, $X_4$, $X_5$, $X_6$, $X_7$, $X_8$, $X_{11}$, $X_{12}$, $X_{13}$, $X_{14}$, $X_{15}$, $X_{16}$, $X_{17}$ and $X_{18}$ are independently alanine or glycine. In a further embodiment the N-terminal amine is acylated and the C-terminal carboxylic acid group is replaced with an amide.

In one embodiment two separate libraries of peptides are provided. The first representing a 1-Phosphohistidine Mimetic Peptide Library and having the general structure:

AcCys-A/G-A/G-A/G-A/G-1-pTza-A/G-A/G-A/G-A/G-CONH$_2$ and the second library representing a 3-Phosphohistidine Mimetic Peptide Library and having the general structure:

AcCys-A/G-A/G-A/G-A/G-3-pTza-A/G-A/G-A/G-A/G-CONH$_2$, wherein Ac=acylated N-Terminus, Cys=L-Cysteine for coupling antigens to KLH, A=Alanine, G=Glycine. The designation A/G indicates that either amino acid can be used at that position, thus each library contains a mixture of $2^8$=256 peptides. In one embodiment the peptides are synthesized under conditions where an alanine or glycine is randomly added to the growing peptide chain during synthesis. 1-pTza and 3-pTza=stable phosphohistidine analogues (Kee et al., *J. Am. Chem. Soc.*, 2010).

In accordance with one embodiment the general structure of the 1-pTza and 3-pTza Peptide Libraries is as follows, wherein X is a non-hydrolyzable pHis analogue

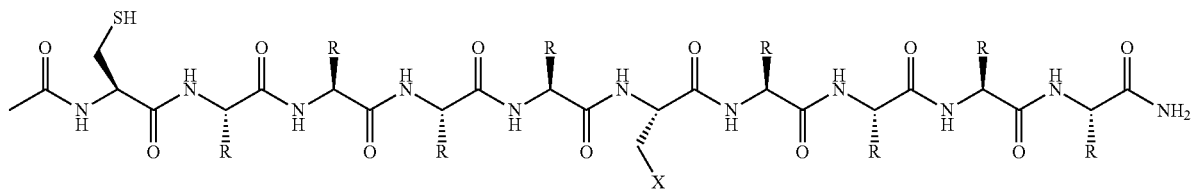

wherein R is H or CH$_3$.

More particularly, in one embodiment the structure of the 1-pTza Peptide Library is

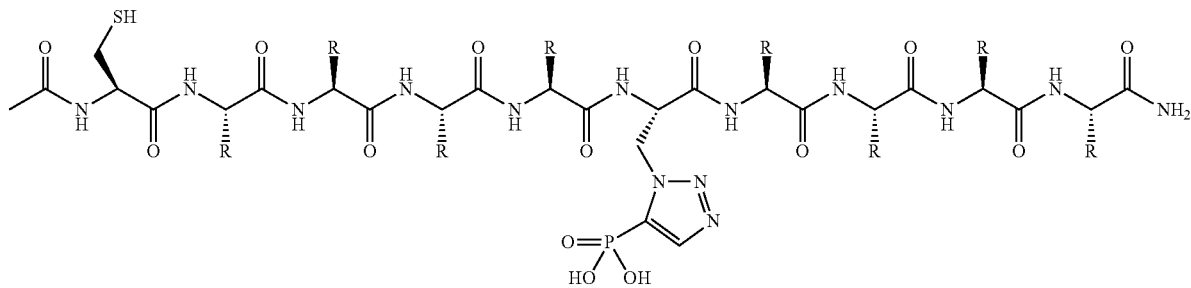

and the structure of the 3-pTza Peptide Library is

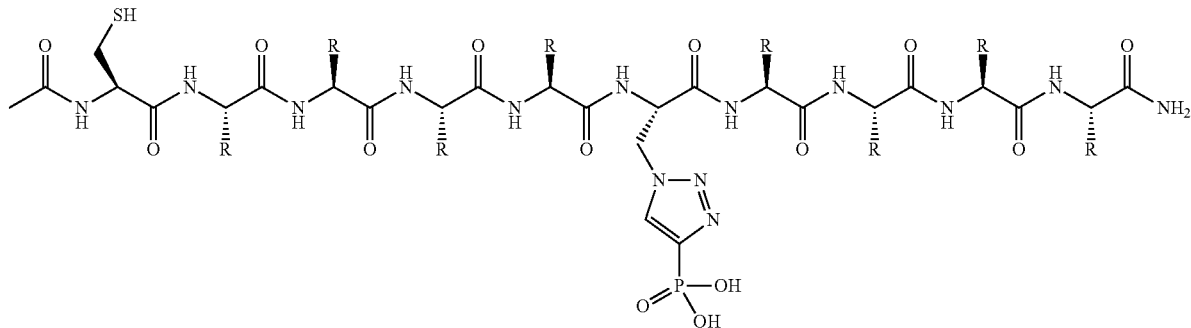

R = H, CH$_3$

The peptides disclosed herein can be used to generate sequence-independent anti-pHis antibodies. In accordance with one embodiment a method for producing sequence-independent anti-pHis antibodies is provided wherein the method comprises i) immunizing a host with a peptide of the general structure Z—W—Y as disclosed herein; and ii) obtaining an antibody-containing host serum produced as a response to said immunization.

In one embodiment the host is immunized with a composition comprising a peptide of the general structure Z—W—Y wherein Z is a sequence selected from the group consisting of $X_1$, $X_1X_2$, $X_1X_2X_3$, $X_1X_2X_3X_4$ (SEQ ID NO: 1), $X_1X_2X_3X_4X_5$ (SEQ ID NO: 2), $X_1X_2X_3X_4X_5X_6$ (SEQ ID NO: 3), $X_1X_2X_3X_4X_5X_6X_7$ (SEQ ID NO: 4) and $X_1X_2X_3X_4X_5X_6X_7X_8$ (SEQ ID NO: 5);

W is an amino acid selected from

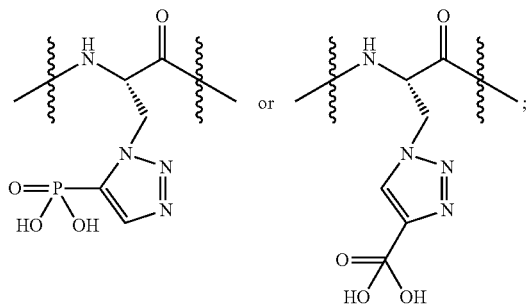

Y is a sequence selected from the group consisting of $X_{11}$, $X_{11}X_{12}$, $X_{11}X_{12}X_{13}$, $X_{11}X_{12}X_{13}X_{14}$ (SEQ ID NO: 6), $X_{11}X_{12}X_{13}X_{14}X_{15}$ (SEQ ID NO: 7), $X_{11}X_{12}X_{13}X_{14}X_{15}X_{16}$ (SEQ ID NO: 8), $X_{11}X_{12}X_{13}X_{14}X_{15}X_{16}X_{17}$ (SEQ ID NO: 9) and $X_{11}X_{12}X_{13}X_{14}X_{15}X_{16}X_{17}X_{18}$ (SEQ ID NO: 10); wherein $X_1$, $X_2$, $X_3$, $X_4$, $X_5$, $X_6$, $X_7$, $X_8$, $X_{11}$, $X_{12}$, $X_{13}$, $X_{14}$, $X_{15}$, $X_{16}$, $X_{17}$ and $X_{18}$ are independently alanine or glycine. In a further embodiment each of the peptides of the libraries are covalently linked to a carrier protein such as KLH. In one embodiment each of the peptides of the libraries comprises one or more peptide selected from the group consisting of lysine, cysteine and tyrosine wherein the carrier protein is linked to the side chain of the lysine, cysteine and/or tyrosine amino acid. Composition comprising the libraries (with or without the covalently linked carrier protein) can be optionally combined with an adjuvant to enhance the immunogenic response when the composition is injected into an animal. In one embodiment the adjuvant is Freund's Complete or Incomplete Adjuvant that is mixed/emulsified with the peptide-carrier protein prior to being injected.)

In one embodiment the host is immunized with a 1-pTza Peptide Library of compounds having the general structure of

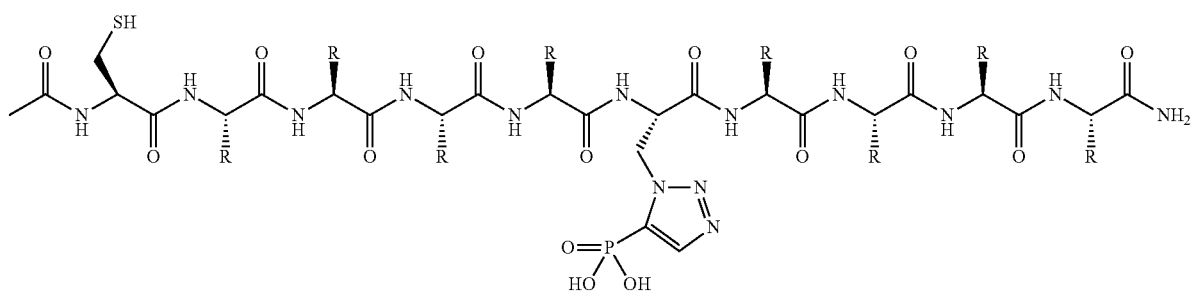

or with a 3-pTza Peptide Library of compounds having the general structure of

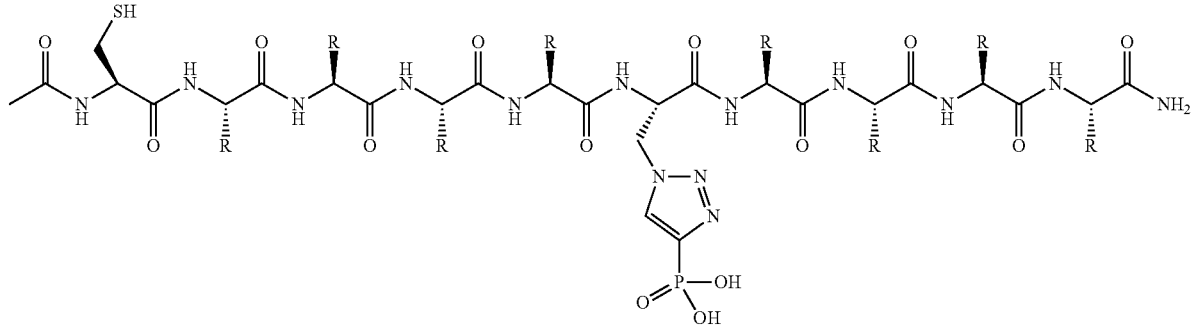

R = H, CH$_3$

In one embodiment the peptides comprising the pTza Peptide Library further include a covalently bound carrier protein such as KLH, to create a hapten antigen. Any adjuvant known to those skilled in the art can be used in the method of generating antibodies. In one embodiment the adjuvant is selected from the group consisting of Bacille Calmette-Guerin, Complete Freund's adjuvant, Incomplete Freund's adjuvant and QS-21 (QS-21 is a purified plant extract that enhances the ability of the immune system to respond to vaccine antigens. It is derived from the Soap bark tree.).

Polyclonal antibodies of the invention may be produced according to standard techniques by immunizing a suitable animal (e.g., rabbit, goat, etc.) with an antigen encompassing a peptide for the general formula Z—W—Y as disclosed herein, covalently linked to a carrier protein, and emulsified with an adjuvant Immune serum is collected from the animal after immunization using standard techniques, and the polyclonal antibodies are then isolated from the immune serum, in accordance with known procedures of affinity purification. The present invention also encompasses the antibodies produced by applicants' invention. In accordance with one embodiment an affinity column is provided for isolating anti-pHis antibodies, wherein the affinity column comprises a peptide of the general formula Z—W—Y as disclosed herein covalently linked to a solid support.

Mouse or rabbit monoclonal antibodies of the invention may be produced in a hybridoma cell line according to standard techniques known to those skilled in the art including for example, the well-known technique of Kohler and Milstein. Nature 265: 495-97 (1975); Kohler and Milstein, Eur. J. Immunol. 6: 511 (1976); see also, CURRENT PROTOCOLS IN MOLECULAR BIOLOGY, Ausubel et al. Eds. (1989). Commercial vendors including, for example, Epitomics can be contracted to undertake splenocyte fusion and hybridoma production after being supplied with spleens form mice or rabbits immunized with an appropriate immunogen. Monoclonal antibodies so produced are highly specific, and improve the selectivity and specificity of diagnostic assay methods provided by the invention. For example, a solution containing the appropriate antigen may be injected into a mouse and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Alternatively, rabbit fusion hybridomas may be produced as described in U.S. Pat. No. 5,675,063, C. Knight, Issued Oct. 7, 1997. The rabbit spleen cells are fused with a (previously patented) suitable fusion partner to create an immortal cell line which is then grown in a suitable selection media, such as one including hypoxanthine-aminopterin-thymidine (HAT), and the cell supernatant screened for monoclonal antibodies having the desired specificity. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, Science 246: 1275-81 (1989); Mullinax et al., Proc. Nat'l Acad. Sci. 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., Proc. Natl. Acad. Sci., 82: 8653 (1985); Spira et al., J. Immunol. Methods, 74: 307 (1984)). The invention also provides hybridoma clones that produce monoclonal antibodies specific for any protein containing a phosphohistidine. The heavy and light chain sequences from a mouse or rabbit hybridoma can be cloned and sequenced, and introduced into both eukaryotic and prokaryotic expression vectors to produce recombinant antibodies.

In accordance with the present disclosure the antibodies produced by immunizations with the peptides disclosed herein will specifically bind to peptides comprising a phosphohistidine, but will not specifically bind to an identical peptide that comprises a histidine in place of the phosphohistidine. In one embodiment the antibody is polyclonal, and in another embodiment the antibody is monoclonal. The present invention also encompasses any hybridoma cell line producing such antibody. Accordingly, the antibodies of the present disclosure will specifically bind to histidine bearing amino acid sequences only when the protein is phosphorylated at the histidine (i.e, the protein comprises a 1- or -3-pHis). In one embodiment the antibody will specifically bind to an amino acid sequence of at least 3, 4, 5, 8 or 10 amino acids in length that bears a phosphohistidine, optionally an internal phosphohistidine. In one embodiment the antibody will specifically bind to an amino acid sequence bearing a phosphohistidine, optionally an internal phosphohistidine, wherein the amino acid sequence has a maximum length of 1,000, 800, 600, 500, 400, 300, 200, 100, 50, 25, 15, 10 or 5 amino acids. In one embodiment the antibody will be specific for any and all amino acid sequences bearing a phosphohistidine (i.e., will bind to proteins containing a phosphohistidine independent of amino acid sequence, but will not bind to an amino acid sequence lacking a phosphohistidine).

In one embodiment an isolated antibody, or an antigen-binding fragment thereof is provided wherein the antibody comprises a heavy chain variable domain comprising the amino acid sequence of SEQ ID NO: 19, and a light chain variable domain comprising the amino acid sequence of SEQ ID NO: 20. In one embodiment the antibody is a monoclonal antibody and in a further embodiment the antibody is a rabbit antibody. In one embodiment the antibody is recombinant. In one embodiment the antibody specifically binds to peptides comprising a phosphohistidine, but will not specifically bind to an identical peptide that comprises a histidine in place of the phosphohistidine. In one embodiment the antibody will specifically bind to an amino acid sequence that comprises a 1-pHis amino acid. In one embodiment the antibody is produced by injecting a mammal with an immunogen comprising a 1-pTza Peptide Library of compounds having the general structure of

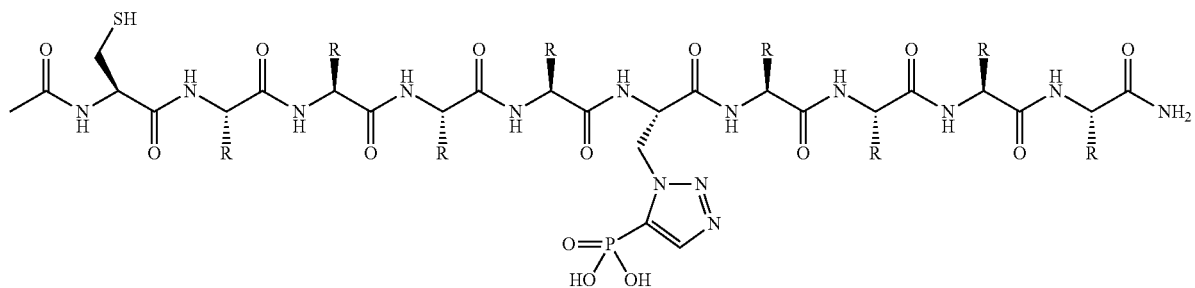

or with a 3-pTza Peptide Library of compounds having the general structure of

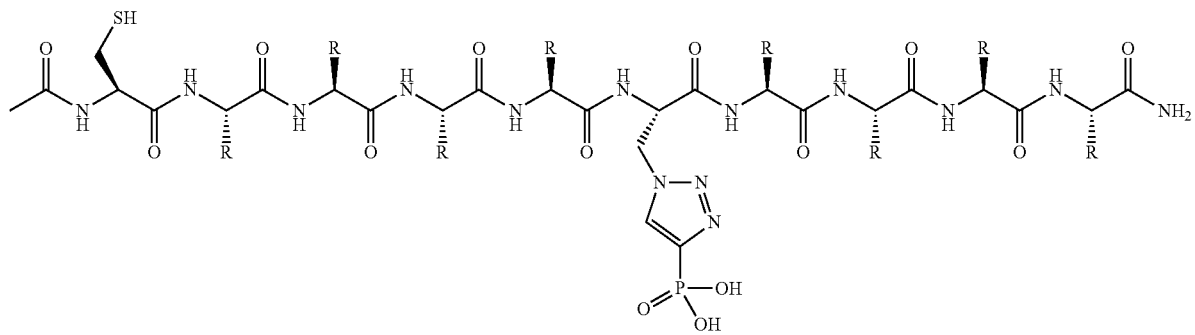

R = H, CH₃

In a further embodiment the antibody is produced by injecting a mammal with the above immunogen, wherein the immunogen further comprises a carrier protein. In one embodiment an isolated polynucleotide is provided encoding an antibody that specifically binds to peptides comprising a phosphohistidine, but will not specifically bind to an identical peptide that comprises a histidine in place of the phosphohistidine. In one embodiment the antibody will specifically bind to an amino acid sequence that comprises a 1-pHis amino acid. In one embodiment the isolated polynucleotide encodes an antibody comprising the amino acid sequences of SEQ ID NO: 19 and 20. In one embodiment the nucleic acid sequence comprises SEQ ID NO: 21 and/or SEQ ID NO: 22.

In accordance with another embodiment the disclosure also provides a method for screening biological samples to detect proteins comprising a phosphohistidine. The method comprises the steps of:

(a) incubating/mixing a biological sample with at least one antibody that specifically binds to peptides comprising a phosphohistidine (i.e., will not bind to an identical peptide that comprises a histidine in place of the phosphohistidine) under conditions suitable for formation of a reagent-antibody complex (phosphohistidine-antibody complex). Since phosphohistidine is heat and acid labile, biological samples will be buffered at pH 8.0 or above and handled in such a manner that will preserve histidine phosphorylation (i.e. the avoidance of heat and acidic conditions whenever possible.) In addition, the phosphohistidine specific phosphatase PHPT1 may be inhibited or depleted from cells through RNA interference, either transiently or stably in a cell line expressing PHPT1 shRNAs.

(b) detecting the presence of said complex in said sample, wherein the presence of said complex indicates the presence of a protein comprising a phosphohistidine in said sample. In one embodiment the antibody is labeled. In one embodiment the anti-pHis antibody is not directly labeled but is detected via a labeled secondary antibody. Means for producing a detectable signal include the use of radioactive labels, fluorescent labels, enzyme labels, and so forth. Examples of suitable immunoassays are the radioimmunoassay, immunofluorescence methods, enzyme-linked immunoassays, immuno-(western) blotting, immunoprecipitation, and the like.

The peptides and antibodies disclosed herein may be conjugated to a solid support suitable for a diagnostic assay (e.g., beads, plates, slides or wells formed from materials such as latex or polystyrene) in accordance with known techniques. Antibodies of the invention, may likewise be conjugated to detectable groups such as radiolabels (e.g., $^3$H, $^{14}$C, $^{33}$P, $^{35}$S, $^{125}$I, $^{131}$I), enzyme labels (e.g., horseradish peroxidase, alkaline phosphatase), far-red laser-activated dyes, and fluorescent labels (e.g., fluorescein) in accordance with known techniques.

In accordance with one embodiment an isolated or purified antibody is provided that specifically binds to a peptide or protein comprising a phosphorylated histidine independent of amino acid sequence. However, the antibody does not bind to an identical amino acid that lacks a phosphorylated histidine and only contains non-phosphorylated histidine. In one embodiment the antibody is a polyclonal antibody, and in another embodiment the antibody is a monoclonal antibody. The present dislcosure is also directed to antibodies are humanized or are chimeric. Nucleic acids and vectors encoding the antibodies or portions thereof, recombinant cells that contain the nucleic acids, and compositions comprising the antibodies or antigen-binding fragments are also part of the present disclosure.

In one embodiment a kit is provided for detecting proteins that comprise a phosphohistidine. In one embodiment the kit comprises a polyclonal or monoclonal antibody that specifically binds to peptides/proteins comprising a phosphohistidine independent of the sequence of the peptide/protein. In one embodiment the kit further comprises a secondary antibody conjugated to a detectable label. The kit may alternatively or in addition include one or more containers, e.g., vials, tubes, bottles, and the like, optionally containing the antibody and assay reagents in a lyophilized form or in an aqueous solution. Preferably, the kits will also include instructions for use.

EXAMPLE 1

Generation of Sequence Independent pHis Antibodies

Histidine exists as two tautomers and undergoes rapid tautomerization, with a hydrogen present at either N1 or N3 of the imidazole ring. Consequently, phosphorylation can occur at either N1 (1-pHis) or N3 (3-pHis) of the imidazole ring and isomerization can occur between N1 and N3. The local hydrogen-bonding environment of target His residues likely determines specificity of pHis at N1 or N3 in proteins.

Unsuccessful attempts have been made to generate pHis antibodies-pHis containing peptide immunogens are hydrolyzed too rapidly to elicit an immune response. In 2010, two groups (Muir-Rockefeller & Webb-Leeds) successfully synthesized stable analogs of pHis (pTza). The Muir group successfully incorporated the analogs into synthetic peptides, and raised the first sequence-specific pHis antibody (histone H4). pHis substrates lack an obvious pattern/motif in flanking amino acids and so it has been difficult to generate pHis antibodies that recognize more than one single kinase target sequence.

To generate sequence independent pHis antibodies, non-hydrolyzable phosphohistidine analogs were synthesized and then incorporated into synthetic peptides containing these pHis analogs flanked by randomized Gly and Ala. These peptide libraries were coupled to KLH, emulsified with Freund's adjuvant, and injected into New Zealand White rabbits. The rabbits were bled and antibodies recovered by affinity purification. Validation of the recovered anti-1-pHis and anti-3-pHis polyclonal antibodies was conducted based on standard immunoblot and immunoprecipitation procedures using purified pHis proteins and cell lysates.

Materials and Methods

Reagents and their sources were as follows: KLH for peptide conjugation (Calbiochem; catalog no. 374817), Rosetta 2 (DE3) Competent Cells (Novagen; Catalog no. 71397), Glutathione Resin (GenScript; catalog no. L00206), PreScission Protease (GE Healthcare; catalog no. 27-0843-01), PBS blocking buffer with 1% Casein (BioRad; catalog no. 161-0783). Freund's Complete Adjuvant and Freund's Incomplete Adjuvant (Calbiochem; catalog no. 344289 and 344291), Adenosine 5'-triphosphate disodium salt solution (Sigma; catalog no. A6559), 2,3-diphosphoglycerate (Sigma; catalog no. D5746).

Immunizing Peptide Library Synthesis

Three synthetic peptide libraries have been synthesized, consisting of either histidine or a non-hydrolyzable pHis analogue flanked by randomized amino acids (glycine [R=H] and alanine [R=CH3]), to promote generation of sequence-independent anti-pHis Abs. Each library is a complex mixture of peptides that are acylated at the N-terminus and contain L-cysteine for coupling to KLH. The three libraries each comprise polypeptides 10 amino acid in length and of the general structure:

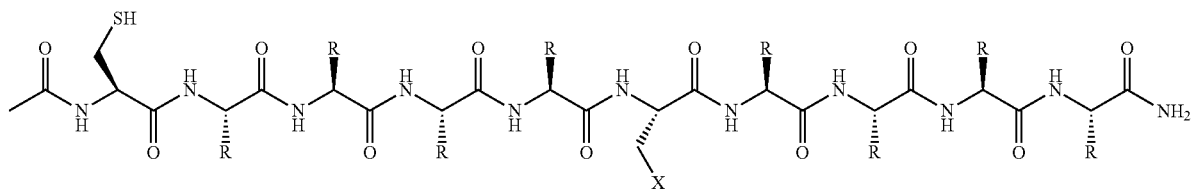

wherein
R is independently Gly or Ala (randomly assigned);
X is His, 1-pTza or 3-pTza (pTza=phosphoryltriazolylalanine);
each polypeptide is acylated at the N-terminus; and each polypeptide comprises an L-Cysteine (e.g., at or near the N- or C-terminus) for chemical ligation to a carrier protein (e.g., KLH). The total number of polypeptide combinations is $2^8 \times 3 = 768$, and thus each of the three libraries (His, 1-pTza and 3-pTza contain 256 unique polypeptides The library incorporating histidine was used for negative selection of Abs that recognize non-phosphorylated histidine. The immunizing peptide libraries, one for each isomer, contain the non-hydrolyzable analogues, 1-pTza & 3-pTza, respectively. The pTza peptide libraries were coupled to KLH through their L-cysteine by the heterobifunctional linker m-maleimidobenzoyl-N-hydroxysuccinimide ester (MBS) according to previously published methods (Using Antibodies: A Laboratory Manual by Ed Harlow, Ch 5) wherein the carrier KLH is activated and purified prior to the coupling.

Rabbit Immunization

In general, rabbits were immunized every three to four weeks and serum was collected ten days after each immunization. Each rabbit was injected intradermally with 0.5 ml antigen mixed with 0.5 ml adjuvant where Complete Freund's Adjuvant was used for the initial injection, and each subsequent injection was made with Freund's Incomplete Adjuvant.

Peptide Dot Blots

Each of the three peptide libraries (0.5 mg) was dissolved in PBS and used to make a 1 ug/ul stock solution. Six fold, 1:5 serial dilutions were performed with a starting concentration of 500 ng/ul for each peptide library. 1 ul of each peptide dilution was spotted on nitrocellulose membranes (Whatman Protran BA85) and allowed to dry for 30 min Membranes were then blocked for 1 hr at room temperature in blocking buffer (0.1% Casein Block [BioRad] in 0.2×

Figure 5A:
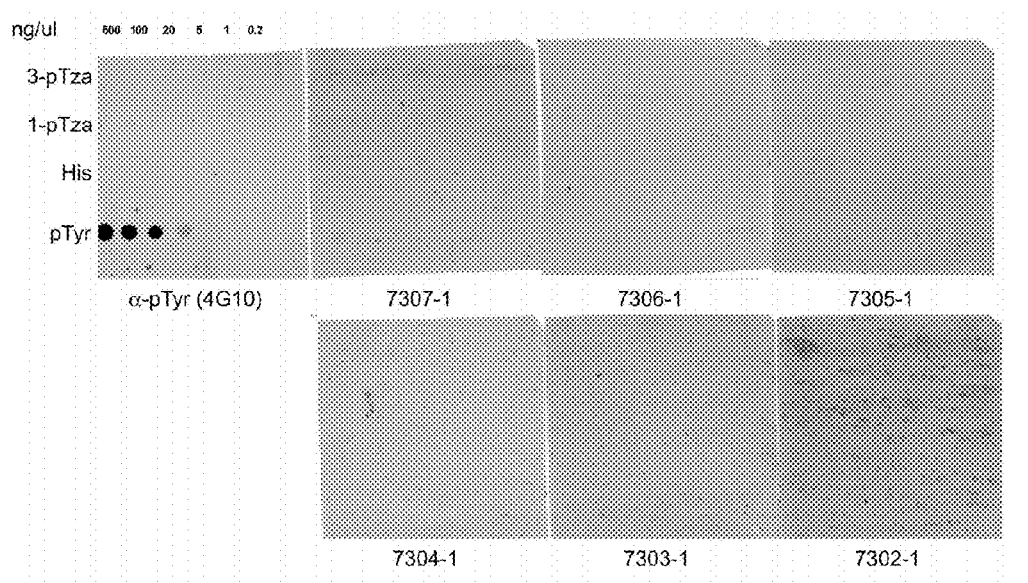
FIGS. 5A-5C. provides the results of immunization of rabbits with the 1-pTza and 3-pTza synthetic peptide libraries. Three New Zealand White rabbits were immunized with the 3-pTza synthetic peptide library (7302, 7303 and 7304), and three rabbits were immunized with the 1-pTza synthetic peptide library (7305, 7306 and 7307). Bleeds were taken at 30 days after initial immunization and 10 days after subsequent immunizations. Dot blots consisting of the two peptide, phophohistidine analogs (1-pTza and 3-pTza), as well as a non-phosphylated negative control (His) and a phosphorylated tyrosine negative control (pTyr) were analyzed to measure antibody titer in the rabbits. Bleed 1 (FIG. 5A) fails to detect IgG against the phosphorylated peptide analogs as expected, since early antisera contains mostly IgM. Bleed 2 (FIG. 5B) reveals antibodies having specificity for the respective immunogen. Specifically, rabbit serum was used at 1:500 dilution (and not affinity purified) and 5 of 6 rabbits' serum shows reactivity specific to the immunogen, with no cross-reactivity between 1-pTza and 3-pTza isomers or His and pTyr peptides. An antibody that binds phosphorylated tyrosine (4G10) detects the pTyr peptide on the dot blots as indicated in FIGS. 5A and 5C. Similar results were obtained for Bleeds 3 and 4.
Figure 5B:
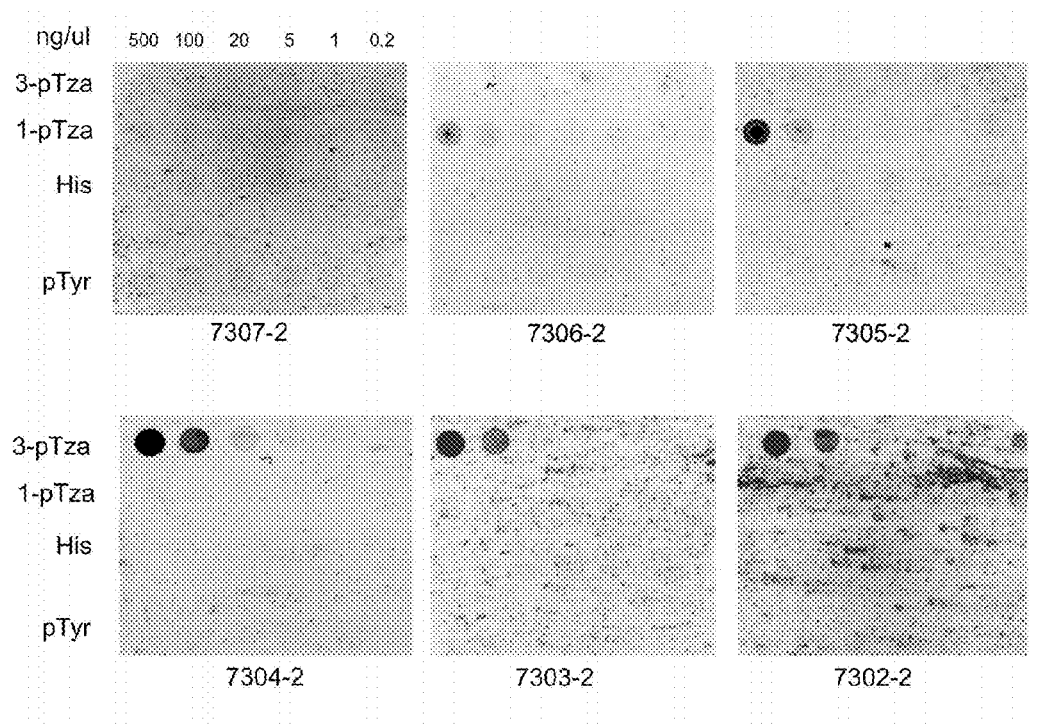
Figure 5C:
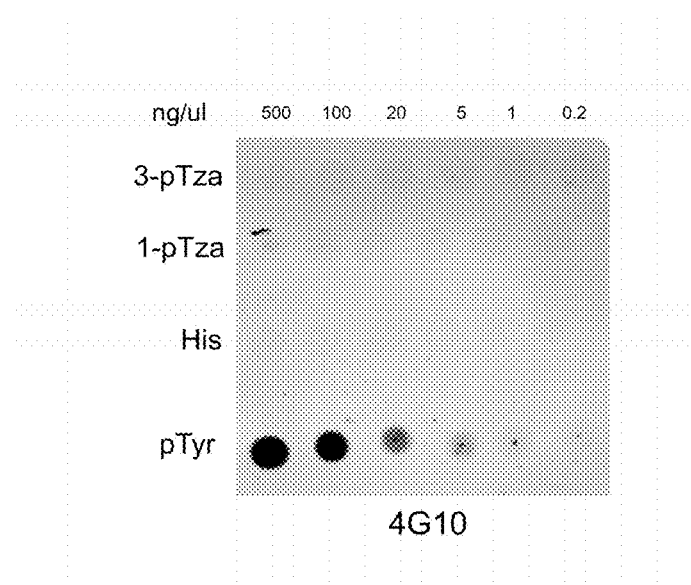
Figure 6A:
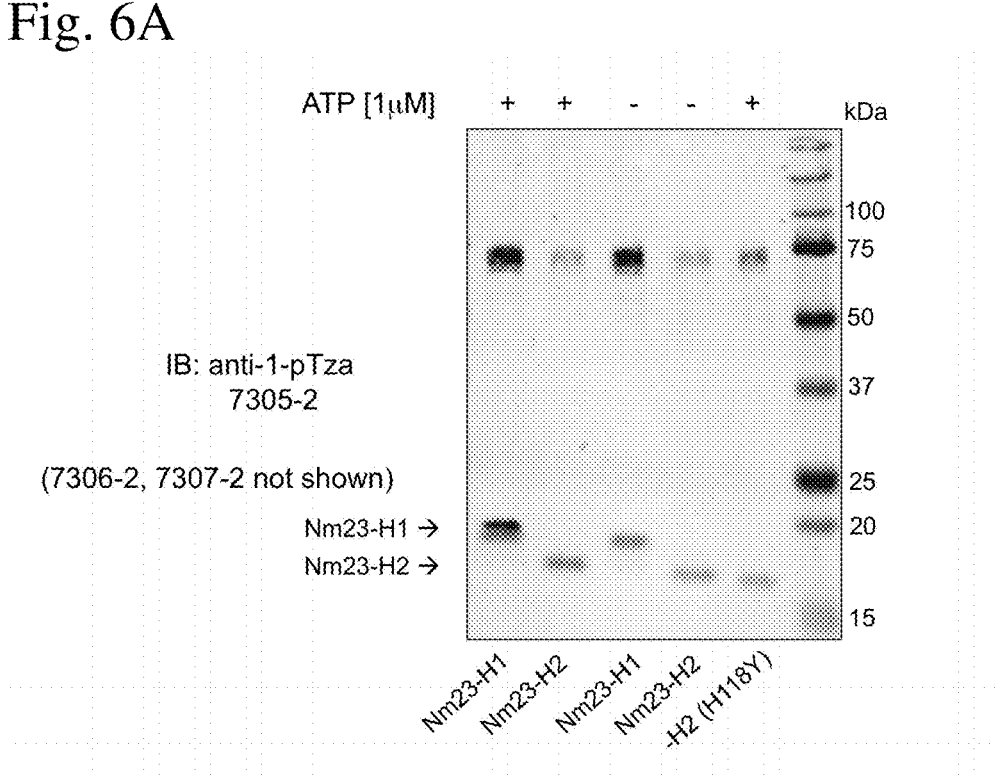
FIGS. 6A & 6B. demonstrate the polyclonal antibodies are capable of binding to proteins autophosphorylated on histidine as well as the 1-pTza and 3-pTza analogs. Recombinant human Nm23 (rNm23) was synthesized and GST-tagged Nm23 proteins purified using a glutathione resin. The column was washed and GST was cleaved on resin with PreScission protease, releasing Nm23 which was then concentrated and allowed to autophosphoryate using standard procedures. Nm23 proteins were incubated for 10 min at room temperature in TMD buffer (20 mM Tris pH 8.0, 5 mM MgCl$_2$, 1 mM DTT) with 1 uM ATP.
Figure 6B:
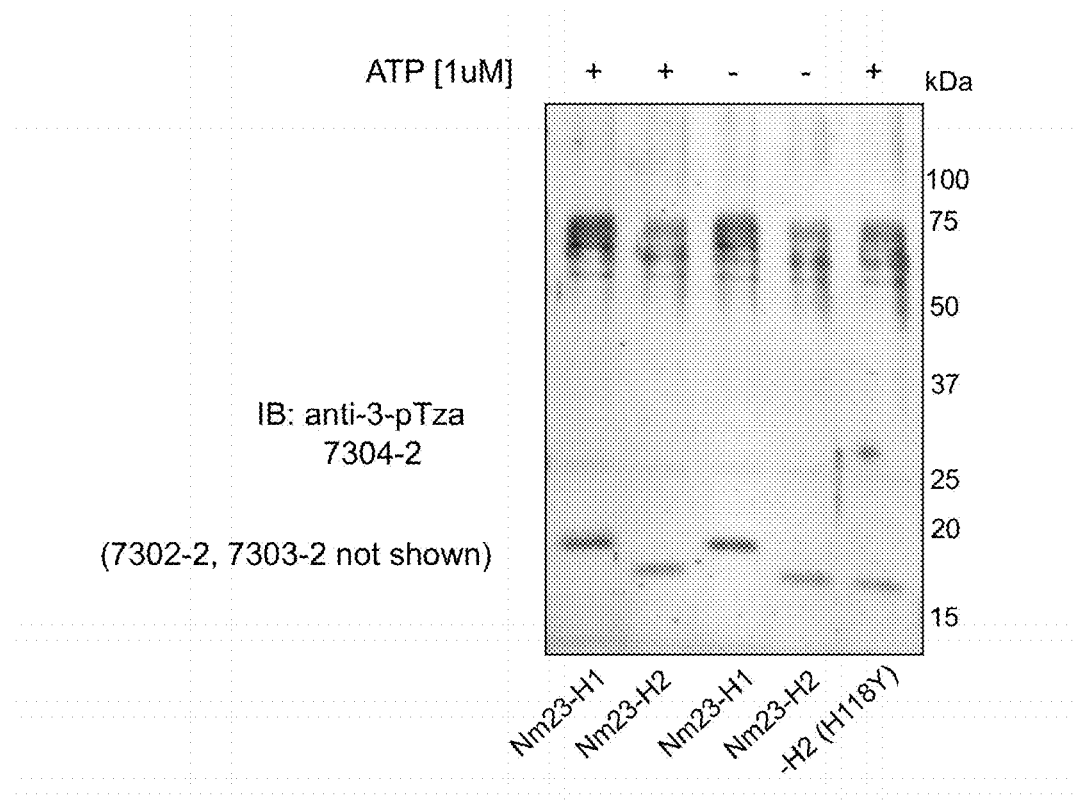

PBS) prior to overnight incubation at 4° C. with rabbit antisera diluted 1:1000 in blocking buffer supplemented with 0.1% Tween-20. Membranes were washed with 0.1% TBST and incubated Alexa Fluor 680 goat anti-rabbit IgG secondary antibodies (Invitrogen, Cat. A21109) diluted at 1:20,000 in 0.1% TBST for 45 min at room temperature. Membranes were then washed and imaged using the LI-COR Odyssey Infrared Imaging System. FIG. 5 (A-E) shows the results of such dot blots for the first four bleeds of the six rabbits used. Rabbits are identified by numbers (7302-7307). Rabbits 7302-7304 were injected with the 3-pTza analog; rabbits 7305-7307 were injected with the 1-pTza analog.

Recombinant Nm23 and PGAM Expression and Purification

The pGEX-Nm23-H1 plasmid was created by inserting Nm23-H1 into the BamH1/EcoRI restriction sites of the GST fusion vector pGEX-6-P1 using the following primers; Forward 3'-GATCGGATCCATGGCCAACTGTGAGCGTAC-5' (SEQ ID NO: 15) and Reverse 3' GATCGAATTCTCATTCATAGATCCAGTTCTC-5' (SEQ ID NO: 16). The pGEX-PGAM plasmid was created by inserting PGAM into the BamH1/EcoRI restriction sites of the same vector using the following primers; Forward 3'-GATCGGATCCATGGCCGCCTACAAACTGGTG-5' (SEQ ID NO: 17) and Reverse 3' GATCGAATTCTCACTTCTTGGCCTTGCCCTG-5' (SEQ ID NO: 18). Rosetta 2 (DE3) competent cells were transformed with pGEX-Nm23-H1 and an overnight culture of LB Amp [50]/Chl [34] was inoculated with a single colony for protein expression. The next day, a 1:100 dilution of overnight culture was used to inoculate 200 mL LB Amp [50]/Chl [34] to an $OD_{600}$ of 0.2 and protein expression was induced at $OD_{600}$=0.6 with 1 mM IPTG for 3 hrs at 30° C. E. coli were pelleted at 5,000×g for 10 min at 4° C. and stored at −80° C. until protein purification.

Purification of Nm23-H1 and PGAM: bacterial pellets were thawed on ice, resuspended in 1 mL GST Lysis Buffer (50 mM Tris-HCl pH 8.0, 100 mM NaCl, 1 mM DTT)/50 mL culture and sonicated to lyse cells (8 sec. pulse, rest 1 mM, 4× (on ice)). Sonicated lysates were spun at 14,000×g for 30 min at 4° C. to pellet insoluble material. The Glutathione Resin (1.5 mL slurry per 200 mL culture) was equilibrated by washing with GST Lysis Buffer. The washed resin was resuspended with 2 mL GST Lysis Buffer/200 mL culture and the supernatant from bacterial lysates was transferred from ultracentrifuge tubes to fresh 15 mL conical tubes, combined with the washed resin and rotated 1.5 hrs at 4° C. The bound resin was pelleted (1000×g for 2 min at 4° C.) and washed 3× with 10 mL GST Lysis buffer.

Ice-cold PreScission Protease Buffer (50 mM Tris-HCl pH 7.0, 150 mM NaCl, 1 mM EDTA, 1 mM DTT) was used to resuspend the washed, pelleted resin and 2.5 ul PreScission Protease (5U/200 mL culture) was added and incubated overnight at 4° C. to cleave GST and release purified Nm23-H1 and PGAM from the resin. The resin was then pelleted (1000×g for 5 min at 4° C.) and the supernatant was carefully removed, transferred to a concentrator/desalting column (Millipore, Ultrafree 0.5-5K MWCO) in 500 ul increments and spun at 12,000×g, 4° C. until the volume reached 50 ul. Buffer exchange was performed by adding 3×450 ul Storage Buffer (50 mM Tris-HCl pH 8.0, 100 mM NaCl, 1 mM DTT) to the 50 ul concentrated sample. Purified, concentrated Nm23-H1 and PGAM proteins were brought to 10% Glycerol in Buffer B, aliquoted, frozen in liquid nitrogen and stored at −80° C. until use.

Nm23 Autophosphorylation Assay

Autophosphorylation of recombinant Nm23-H1 was performed using ATP as the phosphate donor for Nm23-H1; as a negative control, reactions were performed lacking ATP. 1 ul recombinant Nm23-H1 [1 ug/ul] was added per 50 ul TMD buffer (20 mM Tris-HCl pH 8.0, 5 mM MgCl2, 1 mM DTT). ATP (0.1-1 mM) was added fresh from aliquots of a 10 mM stock solution. Reactions were incubated at room temperature for 10 min and immediately stopped by addition of 5×pH 8.8 Sample Buffer (50 mM Tris-HCl pH 8.8, 2% SDS, 100 mM DTT, 10% Glycerol, 10 mM EDTA, 0.01% bromophenol blue).

Reactions were not heated prior to loading on 12.5% polyacrylamide gels (made with minimal pH 6.8 stacking gels) to preserve phosphorylation of histidine by limiting exposure to heat and low pH. The acid treated controls were performed by adding 15 ul 1M HCL to completed autophosphorylation reactions with incubation at 37° C. for 15 min, followed by neutralization with 15 ul 1M NaOH. All gels were run at 80-100V for approximately 3 hrs at 4° C. to prevent generation of heat. Proteins were transferred at 30V to PVDF membranes, overnight at 4° C. for immunoblotting by standard procedures. The detection limit for anti-pHis antisera was assayed by making a 1:2 serial dilutions (200, 100, 50, 25, 12 and 6 ng) of autophosphorylated Nm23-H1 kinase in TMD buffer. 5×pH 8.8 Sample Buffer was added to each dilution followed by analysis by SDS-PAGE (without heating) and immunoblotting with the pHis antisera diluted at 1:1000 in blocking buffer supplemented with 0.1% Tween-20. Membranes were washed and imaged as described above using the LI-COR Odyssey Infrared Imaging System.

PGAM Autophosphorylation Assay

Autophosphorylation of recombinant PGAM was performed using 2,3-diphosphoglycerate (2,3-DPG) as the phosphate donor; as a negative control, reactions were performed lacking 2,3-DPG and/or treated with heat and/or acid for 10 min 1 ul recombinant PGAM [1 ug/ul] was added per 50 ul TMD buffer and reactions were incubated at 30° C. for 10 min followed by addition of 5×pH 8.8 Sample Buffer. SDS-PAGE and immunoblotting were performed as described for Nm23-H1.

Figure 7A:
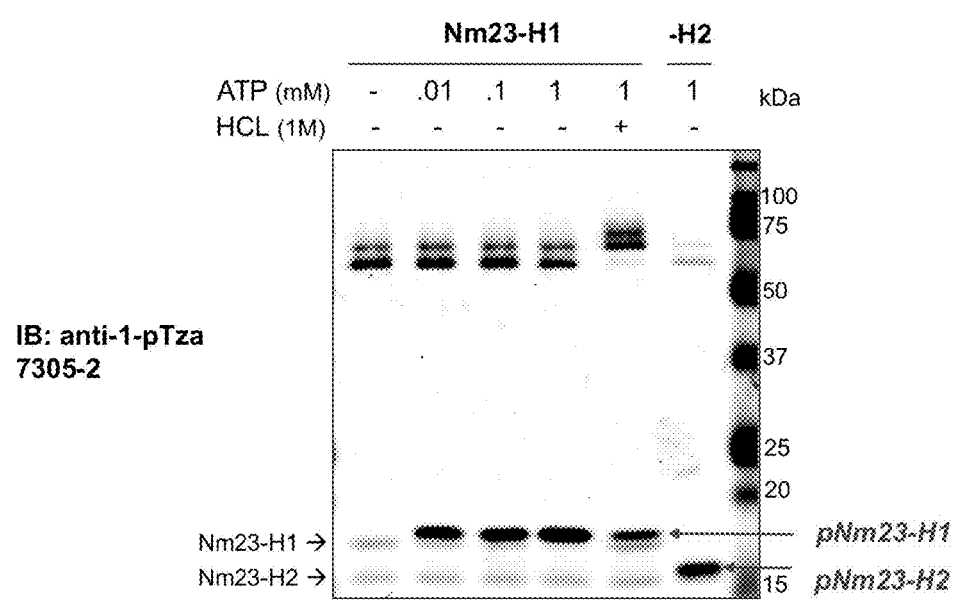
FIGS. 7A & 7B. provide data demonstrating that the detected rNm23 autophosphorylation is reversible. Recombinant Nm23-H1 and Nm23-H2 were autophosphorylated in vitro. 10 mM incubation at RT in TMD Buffer (20 mM Tris pH=8.0, 5 mM MgCl2, 1 mM DTT) +/−ATP. After autophosphorylation, the 100 ul reaction was treated with 25 ul 1M HCL at 37° C. for 15 min. The reaction was neutralized with 25 ul 1M NaOH. Acid treatment of the autophosphorylated rNm23 significantly reduces the binding of anti-1-pTza 7305-2 to the pNm23 band as shown in an immuno-(western) blot probed with anti-1-pTza antisera 1:500 (lane 5, see FIG. 7A). Coomassie stained gel demonstrates the presence of the rNm23-H1/H2 and shows a reduction in the phosphorylated pNm23-H1 in the acid treated lane (see FIG. 7B).
Figure 7B:
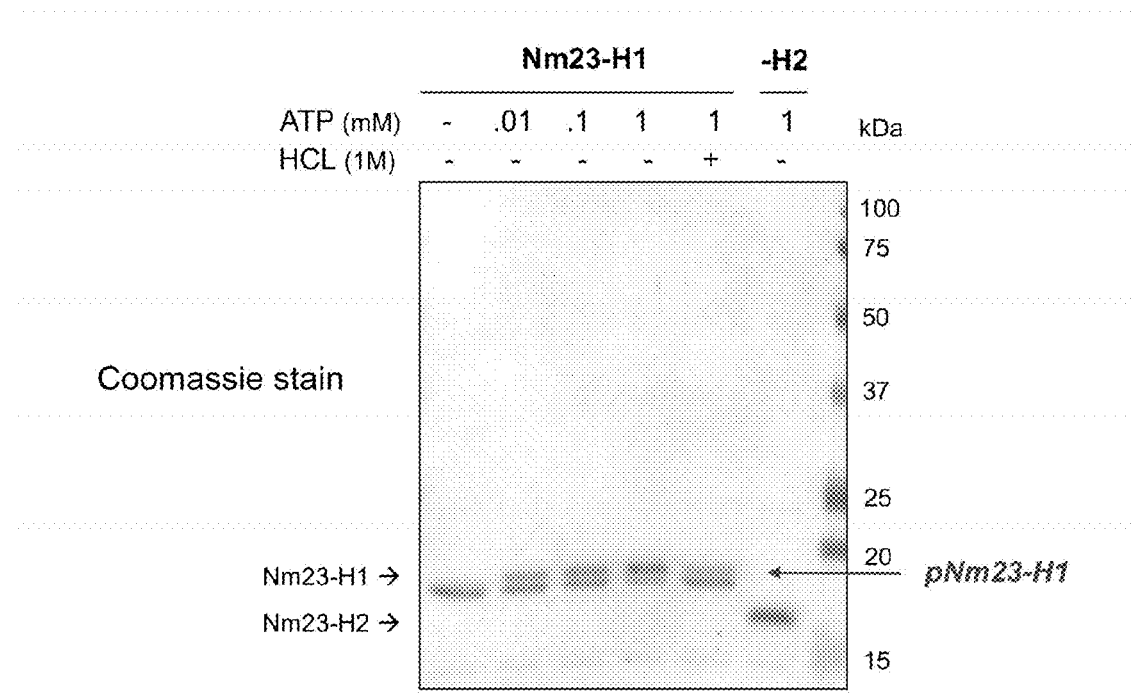

FIGS. 7-9 show preliminary tests (western blots) of the antisera's abilities to recognize the autophosphorylated Nm23-H1.

Results

The peptide libraries have been coupled to KLH via an N-terminal Cys present in the pHis analog containing peptides and an immunization protocol has been initiated for three rabbits per immunogen. Bleeds were screened for pHis detection by dot blot using the immunizing peptides. Unphosphorylated versions of the peptide libraries (with His in place of the pHis analog) were used as negative selection of Abs and served as a negative control for dot blot screening of antisera prior to purification. Anti-1- or -3-pHis-specific Abs were purified from antisera using first an affinity column consisting of immobilized unphosphorylated peptides followed by using affinity columns consisting of the immobilized libraries, which include one/either of the non-hydrolyzable analogues.

To remove Abs crossreactive with other phosphoamino acids, the column was washed with sodium phosphate followed by pSer, pThr and pTyr. That some anti-pTyr Abs cross-react with pHis demonstrates that pHis is indeed antigenic and using the approach outlined above generated Abs that specifically recognize pHis and not other phosphoamino acids. See FIGS. 5A-5E demonstrating polyclonal antibodies specific for the 3-pHis library polypeptides (7306 and 7305) or 3-pHis library polypeptide (7302, 7303 and 7304) were generated.

Figure 4:
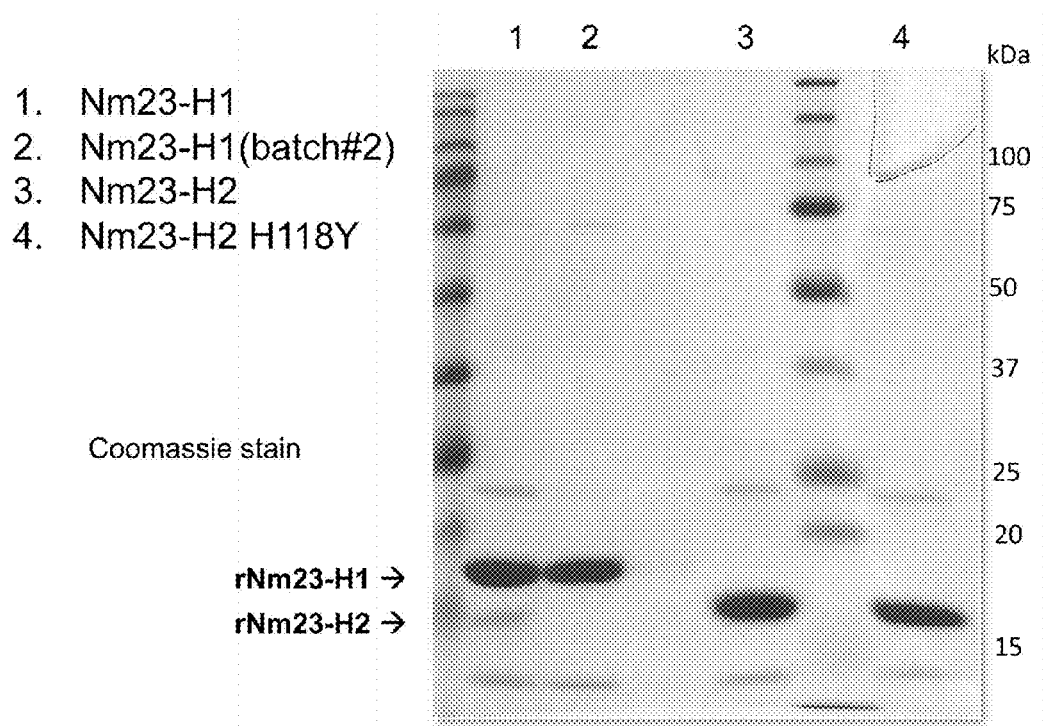
FIG. 4. Purification of recombinant Nm23-H1 & -H2. Wild type (WT) and the autophosphorylation site catalytic mutant (H118Y) of Nm23-H1 and Nm23-H2 were cloned into a GST fusion vector (pGEX-6P-1), transformed into the BL21 derivative, Rosetta 2(DE3) and expressed by IPTG induction. GST-tagged Nm23 proteins were purified with glutathione resin (GenScript). Nm23 proteins were released from the resin by cleavage of GST tags. Purification and complete cleavage of GST tag was assessed by SDS-PAGE and Coomassie staining. As expected, recombinant Nm23-H1 and Nm23-H2 migrate at 18 kDa and 16 kDa respectively.

To validate Ab specificity, autophosphorylated pH118 Nm23-H1/-H2 and dot blots with in vitro phosphorylated pHis substrates (e.g. histone H4) were used as positive controls. Recombinant GST-Nm23 proteins were expressed and purified using glutathione resin with subsequent cleavage of the GST using PreScission protease (See FIG. 4). In vitro autophosphorylation was conducted on the purified recombinant Nm23-H1 as described in the material and method section. Autophosphorylated rNm23 is detected by anti-1-pTza 7305 antisera in an immunoblot (see FIG. 5A); but anti-3-pTza 7305 antisera only produced background/non-specific binding to rNm23 (See FIG. 5B). Presumably this is due to a conserved Glu-NH hydrogen bond present at E129 in human Nm23 restricting autophosphorylation to only N1.

Figure 8A:
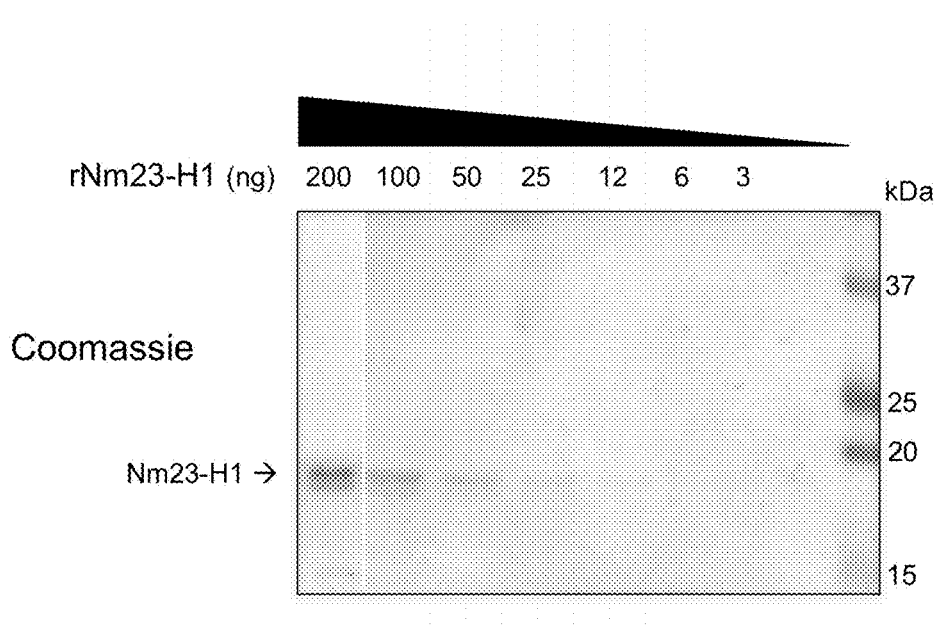
FIGS. 8A-8E.
Figure 8B:
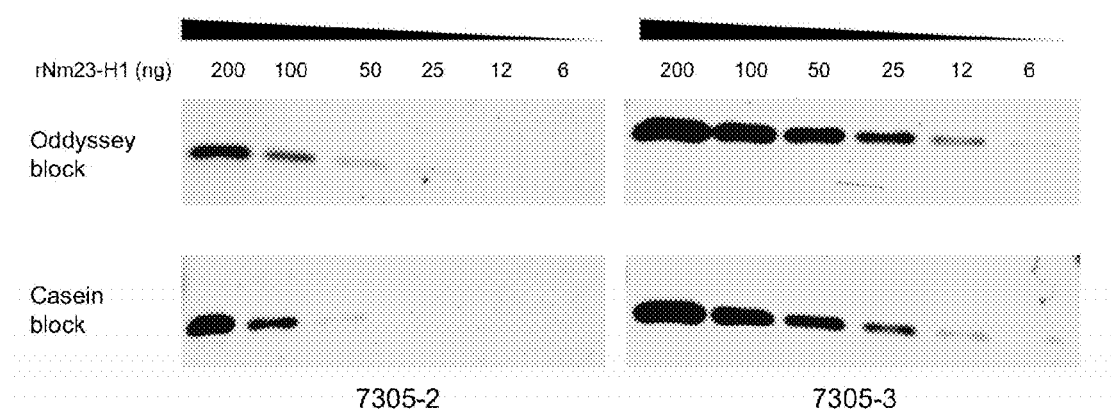
Figure 8C:
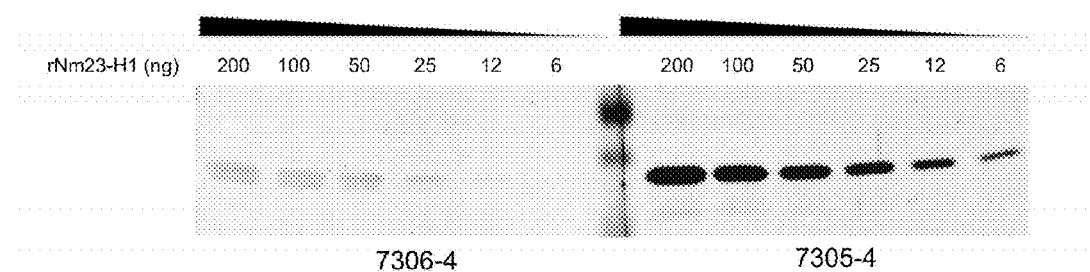
Figure 8D:
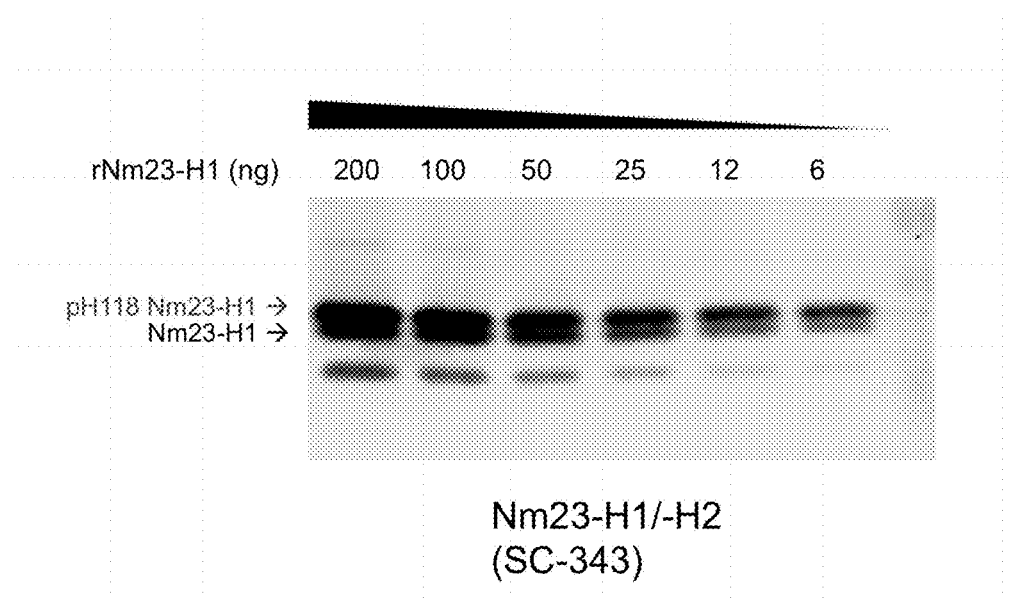
Figure 8E:
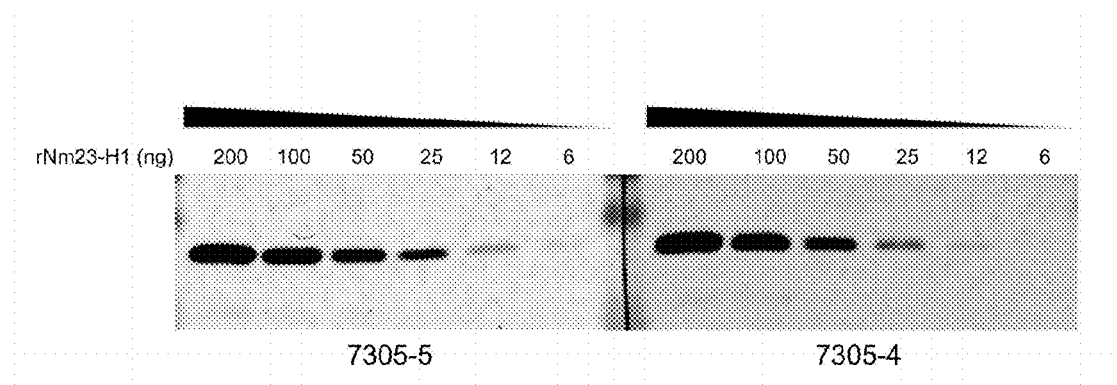
Figure 9A:
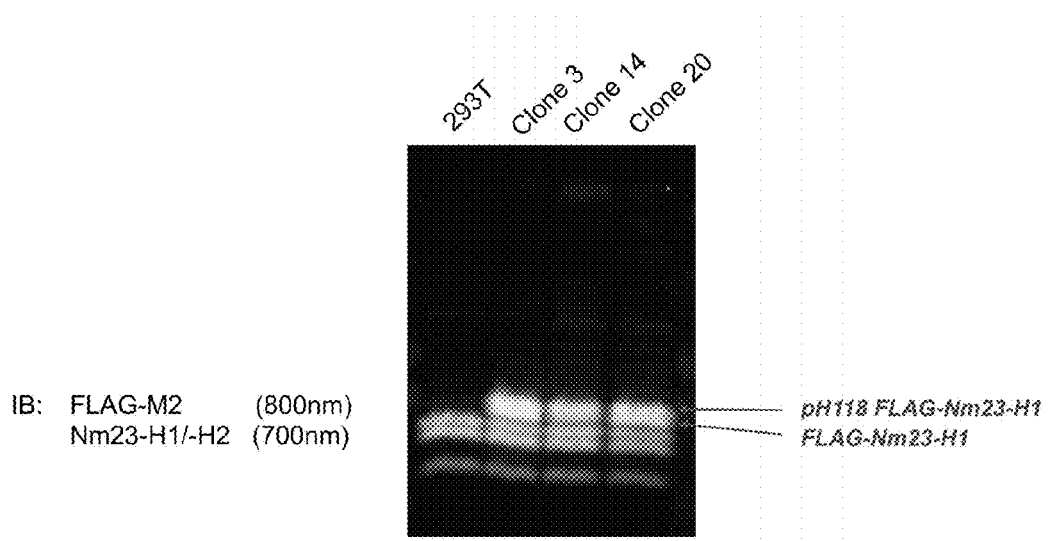
FIGS. 9A & 9B. presents data showing stable cell lines expressing FLAG-Nm23-H1. 293T cells were transfected with DNA constructs expression FLAG-Nm23-H1 and stable lines were identified. The clones with the highest expression relative to tubulin were used for all subsequent pHis immunoprecipitation experiments. Screening cell lines (See FIGS. 9A & 9B) revealed that clone 20 exhibited the highest expression of Nm23-H1 relative to tubulin.

The detected rNm23 autophosphorylation is reversible. Acid treatment (1M HCl at 37° C. for 15 min followed by neutralization with NaOH) of the autophosphorylated rNm23 significantly reduces the binding of anti-1-pTza 7305-2 to the pNm23 band (see FIG. 7A). Coomassie stained gel demonstrates the presence of the rNm23-H1/H2 and shows a reduction in the phosphorylated pNm23-H1 in the acid treated lane (See FIG. 7B). FIGS. 8A and 8B show the coomassie detection limit vs the anti-1-pTza antisera detection limit, respectively for rNm23-H1 autophosphorylation. FIG. 8C shows the titer levels continue to increase in the fourth bleed of 7306 and 7305 rabbits, with FIG. 8D showing the 7306 and 7305 fourth bleed detection limits FIG. 8E compares the titer of bleed 4 vs bleed 5 for detecting rNm23-H1 autophosphorylation using 7305 anti-sera.

Stable Cell Lines Expressing FLAG-Nm23-H1

Figure 9B:
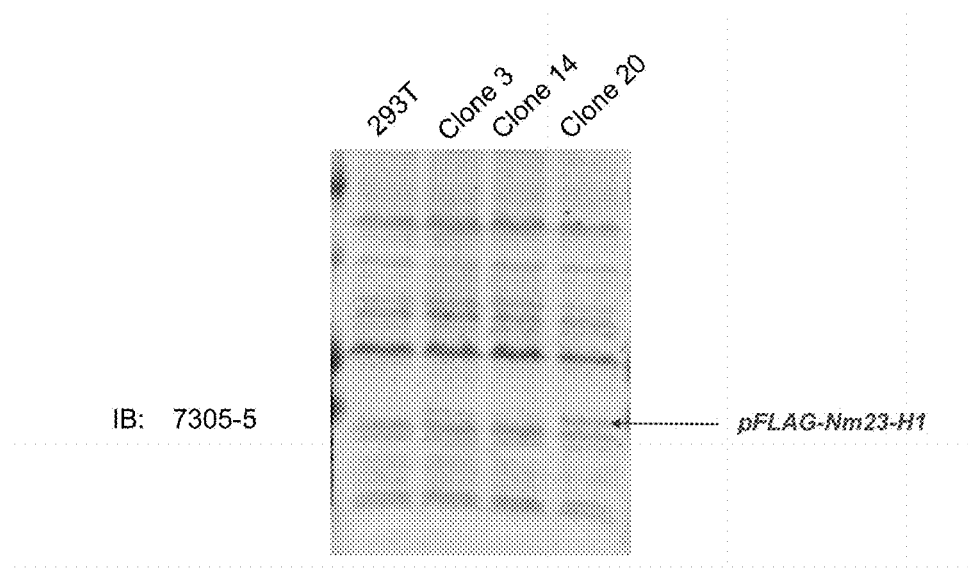

293T cell were transfected with DNA constructs expression FLAG-Nm23-H1 and stable lines were identified. The clones with the highest expression relative to tubulin was then used for all subsequent pHis immunoprecipitation experiments. Screening cell lines (See FIGS. 9A and 9B) revealed that clone 20 exhibited the highest expression of Nm23-H1 relative to tubulin. As shown in FIG. 9B 7305-5 anti-sera can detect pFLAG-Nm23-H1.

In general, pHis substrates will be identified by immunoprecipitation (IP) and immunoblotting (IB) with anti-pHis Abs, or by pHis peptide enrichment via an immobilized anti-pHis Ab affinity column and mass spectroscopy (MS) analysis. pHis substrates with relevance to cancer and metastasis will be identified by comparing cells with high and low Nm23 expression, followed by annotation using GO and pathway analysis to prioritize which substrates to study further.

EXAMPLE 2

Identification and Analysis of pHis Substrates
Endogenous pHis Substrates from Cancer Cells.

pHis-containing proteins from whole cell lysates (buffered to pH 8.0 to stabilize pHis) made from cancer cell lines or primary tumor samples with high metastatic potential (i.e. low Nm23 expression; breast, ovarian, hepatocellular, cervical and gastric carcinomas or low metastatic potential (i.e. high Nm23 expression) will be immunoprecipitated using anti-pHis Abs. The immunoprecipitated proteins will be digested into peptides and enriched for pHis prior to MS analysis. Protocols for the selective extraction of peptides containing phosphomonoester residues (pSer, pThr and pTyr) using immobilized Fe(III) or Ga(III) ion affinity chromatography are well established. A similar protocol has been developed for enrichment and identification of pHis peptides based on use of appropriate pH conditions, and immobilized Cu(II) ion affinity chromatography (Cu(II)-IMAC) followed by matrix-assisted laser desorption/ionization time-of-flight mass spectrometry (MALDI-TOF MS). The synthetic pHis immunogen peptides and recombinant, autophosphorylated Nm23 proteins will be used to optimize identification of pHis-containing peptides by MS. His phosphorylation levels due to Nm23 His kinase activity are expected to be reduced in highly metastatic cell lines relative to non-metastatic cell lines, reflecting the reduced Nm23-H1/-H2 expression in these cells. We will also deplete PHPT1 pHis phosphatase using shRNA in an attempt to increase the levels of pHis in proteins, analogous to using pervanadate to enhance pTyr levels.

Overexpression of Histidine Kinases in Cells.

Autophosphorylation of His118 (H118) on Nm23-H1 and Nm23-H2 is required for their kinase activity. Line IV human melanoma cells have high metastatic potential and low Nm23 expression. Line IV cell lines stably expressing Nm23-H1, Nm23-H2 and their respective, catalytically inactive mutants (H118Y) have been obtained. Cell lysates or tryptic digests will be probed for pHis with Abs and analyzed by MS as described in above. In vitro kinase assays using purified proteins will be used to validate selected substrates of interest identified by MS. Mutagenesis of specific His residues to generate pHis-deficient mutants will be used to investigate the in vivo function of pHis for each respective target by expression in a null background (e.g. knockout MEFs) or by re-expression in depleted cells (e.g. si/shRNA-treated cells) to determine if the pHis-deficient mutants rescue WT protein function.

Nm23-H1 and Nm23-H2 genes are 88% identical and yet have distinct substrates and functions. Nm23 genes are highly conserved between human and rodents and have similar organization and tissue expression. Nm23-H1−/− and Nm23-H2−/− mice are viable; however, H1/H2-deficient mice are not, suggesting some functional overlap and that compensation occurs. Tissues from Nm23-H1−/− and H2−/− mice will be analyzed for pHis (using methods outlined above, as well as straight IB) and compared with tissues of WT mice to determine substrates specific for Nm23-H1, Nm23-H2 or both. Selected targets identified in this way will be further investigated through the use of si/shRNA knockdown and re-expression of WT or pHis-deficient mutants to examine effects of His phosphorylation on tumor metastasis (e.g. migration, invasion, anchorage-independent colony formation, and tumorigenesis in nude mice).

EXAMPLE 3

Monoclonal Antibodies

Figure 10A:
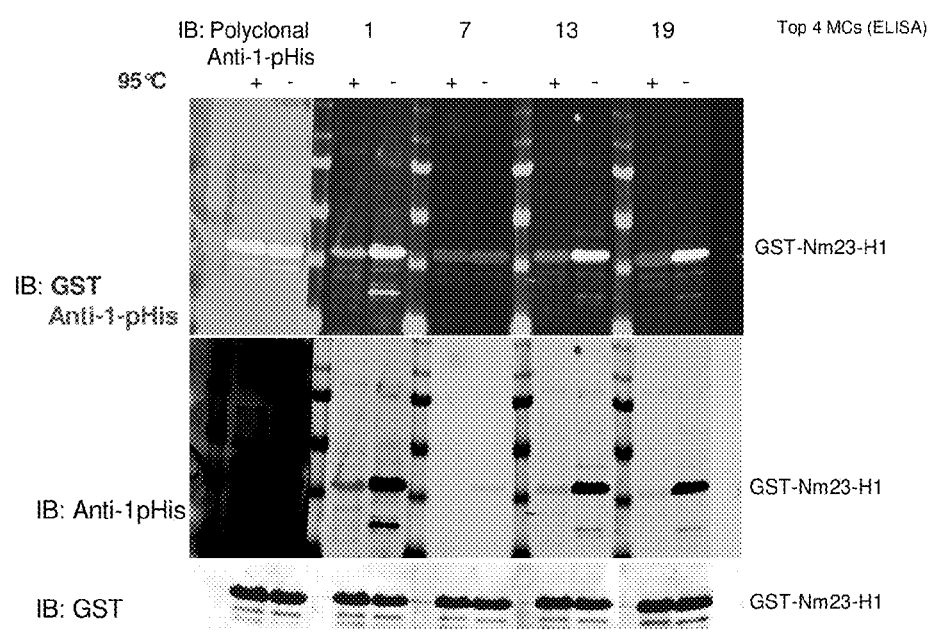
FIGS. 10A & 10B. show the data for four positive hybridoma multiclones and subclones recovered from the 7305 rabbit and their ability to bind to pGEX-Nm23-H1 transformed E. coli lysates.
Figure 10B:
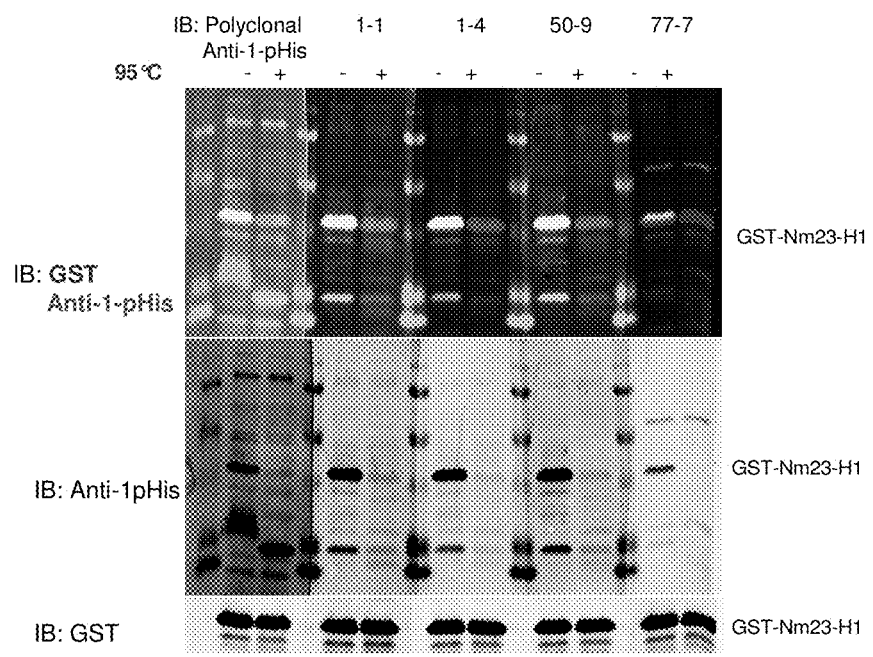

For 1-pHis, rabbit 7305 was chosen for hyperimmunization and rabbit monoclonal antibody (RabMab) production. The spleen was harvested and the rabbit splenic B cells were fused with rabbit partner cells (240E-W2 cells; U.S. Pat. No. 7,429,487, the disclosure of which is incorporated herein by reference). Culture supernatants from the hybridoma cells were screened by ELISA for recognition of 1-pHis and the identified antibodies having specificity for the immunogen were further characterized. For 1-pHis antibodies, 48 positive hybridoma multiclones were identified and screened against genuine pHis: E. coli expressing GST-Nm23-H1, a 293T-FLAG-Nm23-H1 stable cell line and immunoprecipitated FLAG-Nm23-H1 (See FIGS. 10A & 10B). The top 3 were selected for subcloning (clones 1, 50 and 77). Further analysis revealed the loss of pHis signal on Nm23 and other proteins after heating at 95° C. The three selected multiclones were subcloned and the best 9 subclones were selected: SC1-1, 1-3, 1-7, 1-9, 1-11, 50-3, 50-8, 50-11 & 77-11.

Figure 11:
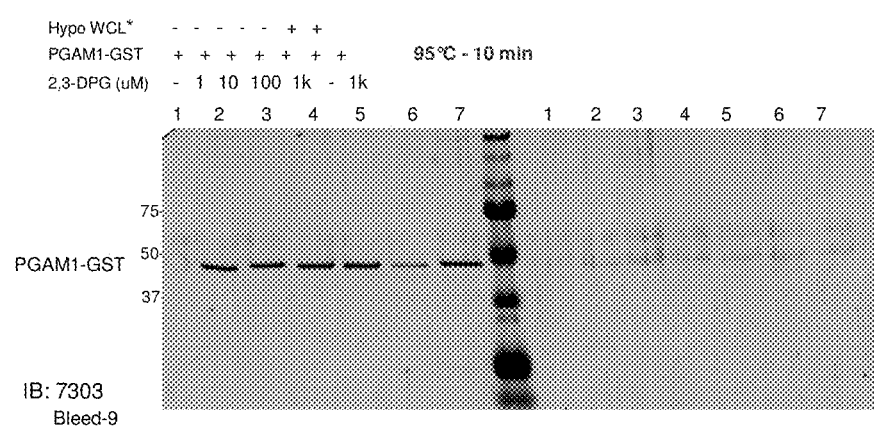
FIG. 11. shows the results of the 3-pHis screening with a preparation of phosphoglycerate mutase (PGAM) in vitro phosphorylated in the presence of 2,3-DPG, and using polyclonal antibodies recovered from the 7303 rabbit (bleed 9). Identical samples were heated to 95° C. for 10 min to confirm the detected signal results from binding to 3-pHis. 7303 (3-pTza rabbit) antisera detects only phosphorylated PGAM. Polyclonal antibodies recovered from the 7304 rabbit also produced a signal but much weaker than for 7303.
Figure 12A:
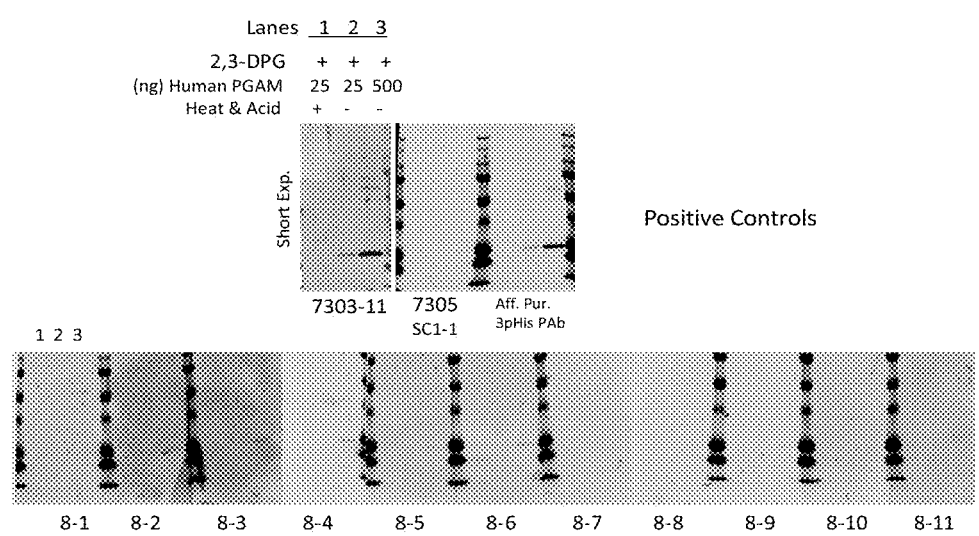
FIGS. 12A & 12B. shows the results of screening subclones of 3-pHis hybridoma multiclone 7303 MC8 with PGAM +/− heat & acid.
Figure 12B:
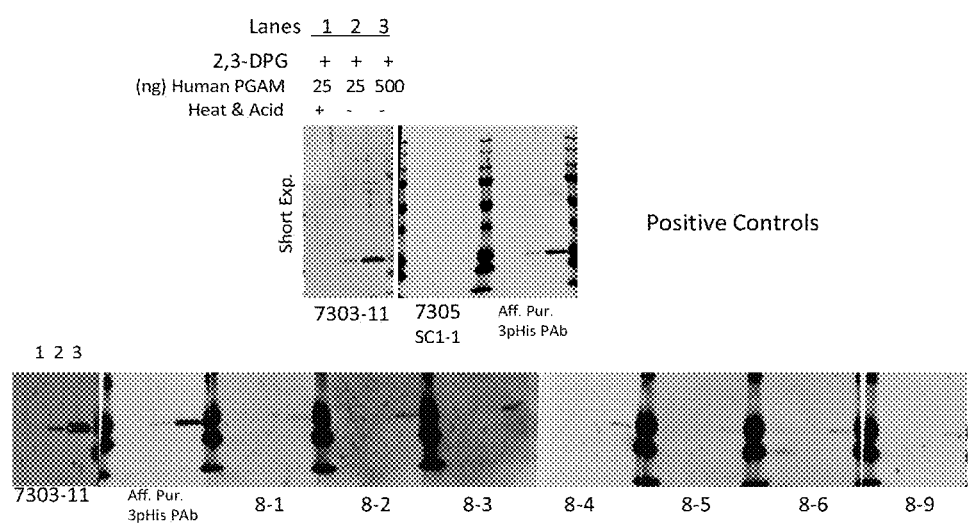

For 3-pHis, rabbit 7303 was chosen for Hyperimmunization and RabMab production. The spleen was harvested and the rabbit B cells were fused with rabbit partner cells (240E-W2 cells; U.S. Pat. No. 7,429,487, the disclosure of which is incorporated herein by reference). Culture supernatants from the hybridoma cells were screened by ELISA for recognition of 3-pHis and the identified antibodies having specificity for the immunogen were further characterized. ELISA screening was hindered by 3-pTza antigen solubility or lack of adherence to ELISA plates Improved solubility was achieved by coupling antigen to BSA for screening and 20 ELISA positive multiclones were obtained. A 3-pHis screening assay was developed based on the 2,3-DPG dependent PGAM phosphorylation. PGAM catalyzes step 8 of glycolysis: The internal transfer of phosphate to convert 3-phosphoglycerate (3PG) to 2-phosphoglycerate (2PG) through a 2,3-diphosphoglycerate (2,3-DPG) intermediate. In vitro phosphorylated PGAM was used as the assay for identifying antibodies specific for 3-pHis. As shown in FIG. 11, polyclonal antibodies recovered from rabbit 7303 were able to bind to phosphorylated PGAM (but not heat-treated PGAM). Only 6-7 PGAM positive multiclones were identified from the 20 ELISA positive multiclones. The top 3 hybridoma multiclones were selected for subcloning—MC6, MC8 and MC17, but only MC8 and MC17 were stable. None of the MC17 subclones could detect genuine 3-pHis in the PGAM assay, however, MC8 subclones could, though weakly, with 7 of 12 subclones producing antibodies that give a weak signal for pPGAM 500 ng (see FIGS. 12A & 12B). This is likely due to very low IgG concentration and should be overcome by purification and concentrating the antibody. Accordingly, subclones 8-1, 8-2, 8-3, 8-4, 8-5, 8-6 and 8-9 were selected.

EXAMPLE 4

Sequencing of SC1 Heavy and Light Variable Region Chains

The SC1-1hybridoma and the SC50-3 hybridoma, expressing monoclonal antibodies SC1-1 and SC50-3 respectively, were deposited in accordance with the Budapest Treaty with the American Type Culture Collection (ATCC) Patent Depository, 10801 University Blvd., Manassas, VA, 20110, on Oct. 30, 2014. The hybridoma expressing monoclonal antibody SC1-1 was deposited as Accession No. PTA 121685. The hybridoma expressing monoclonal antibody SC50-3 was deposited as Accession No. PTA-121686.

The heavy chain variable regions of the SC1-1, SC1-3 and SC50-3 hybridomas were sequenced using either a pooled set of primers or a single primer. Results are provided below.

```
Pooled VH primers - VHP:
RVH1_A
                                            (SEQ ID NO: 19)
5' AGTCGGTGGAGGAGTCCAGG 3'

RVH1_G
                                            (SEQ ID NO: 20)
5' AGTCGGTGGAGGAGTCCGGG 3'

RVH2
                                            (SEQ ID NO: 21)
5' AGTCGGTGAAGGAGTCCGAG 3'

RVH3_C
                                            (SEQ ID NO: 22)
5' AGTCGCTGGAGGAGTCCGGG 3'

RVH3_T
                                            (SEQ ID NO: 23)
5' AGTCGTTGGAGGAGTCCGGG 3'

RVH4_CA
                                            (SEQ ID NO: 24)
5' AGCAGCAGCTGATGGAGTCCGG 3'

RVH4_GA
                                            (SEQ ID NO: 25)
5' AGGAGCAGCTGATGGAGTCCGG 3'

RVH4_CG
                                            (SEQ ID NO: 26)
5' AGCAGCAGCTGGTGGAGTCCGG 3'

RVH4_GG
                                            (SEQ ID NO: 27)
5' AGGAGCAGCTGGTGGAGTCCGG 3'

>HI-SF3-VHP_C08 SC1-1
                                            (SEQ ID NO: 29)
GNNCAAAGTATGATCATCTTCTCTTAGGCAGATCACGACGGTTACTCCTC

ATCTGCTCCTAGTCTCTGGGTCCTCCTCGCTCCATGTCAGGGGCTGGAAT

GGATCGGAAGTGCTGGCGCTTATTGTAGAATATCCTACGCGAGCTGGGCG

AAAAGCCGATCCACCATCACCAGAAACACCAACCTGAACACGGTGACTCT

GAAAATGACCAGTCTGACATCCGCGGACACGGCCACTTATTTCTGTGCGA

GAAGAAGTGATGTTGGTACTTCTGTGGGTTTTGATTCCTGGGGCCCAGGC

ACCCTGGTCACCGTCTCTCTACCTTTTATCTGCCTGACTCCACCCGCTGC tTCCTAAAAATCGAAAAGGGGGGGGCCGGTACAGTTTGGGGTCGGGAGGG

GGGGGTCTGTGGGGATGTCGGCCAGGTAGGCCATTGTCCGCTGCCCGACG

AGGGTTTTATGGGTCGGTGTTAGTCGGGAATTGGGGTATCTACATAGGCG

CAATGAGTAGAATCTCTGATTTTTCTTTTGGGTTGTTGCGGTGCGAGAAA

GAATAGTCCACCGGATCGATCCTGTGTCATTGAGTTTGGGTGAGTCGAGG

TGCTTCCGATACTGCTCCCCTAGGCATCTCA

Single Primer: RVH2
                                            (SEQ ID NO: 30)
5' AGTCGGTGAAGGAGTCCGAG 3'

>HI-SF12-VH3_D09 SC1-1
                                            (SEQ ID NO: 28)
GNATCGCATCTGTACCTAGGTCCTCAGCAGGAAGGCTCATGTGTCCTCCC

TCGATGGGGTAGGCTTGGACTCTGGCCGGGGGGGCCTGGGGGGAGCCTTG

GCCCGGGACAACTAGCTGCAGGGTGGACACCACTTTGCCTAGCGGCACCC

TGGTCACCGTCTCTTCCACCATCACCAGAAACACCAACCTGAACACGGTG

ACTCTGAAAATGACCAGTCTGACAGCCGCGGACACGGCCACTTATTTCTG

TGCGAGAAGAAGTGATGTTGGTACTTCTGTGGGTTTTGATTCCTGGGGCC

CAGGCACCCTGGCACCGTCTCTCTATTGACCATTCCCCTACTCTTGCCGC

CTCTCTCTACGTCCTGGGCACTGCCACCCGCTGGCCCCTGGCCGTCCGCT

AATGGACCACGACCGCACTCGGGCTGCTGGCCATCCCTGTTATCATCCAC

CCCATCGACAGGTCGGTGGACTTCCTGCTGAACTCCAGCCTGCGTAAGCT

CTACCCATCCGTGGGGAAGCCCAGCTCCTCCTGAGCCCACCCTGGTACCT

GGCCTGCGAGTTGGCTCACTCCCACCATGGGAAGTGGGGGCCAGGCTCCC
```

-continued

CGGGGTCTGAGGCCCTGGCACCTGTGTGGATTAGAACTGGATGGAAGCTT

CTAGATGGGGTTTCTGGGAGCATCAGCTGCAGCGAGACCCATACGGAGG

CGGGACCTGACCCCCAACTGTCTCCACGGACACTGTGACAGTGGCGGGGA

GTGCGGGATGGCGCCATCCATAGCATGGAAGTCCTGTGCTCCCGCGGGG

ATACATATCTTATGCCTGGTATGGAG

SC1-3 Heavy Chain

Pooled VH primers - VHP:
\>HI-SF15-VHP_G09 SC1-3
(SEQ ID NO: 31)
GGCGTACGTATGATCATCACGCTCTTAGGTAGATCACGGCGTTACTCCTC

ATCGGCTACAAAATGTCCTGGGTCCTGCTCGCTCCATGTAAGGGGCTGGA

ATGGATCGGAAGTGCTGGCGCTTATGGTAGAATATACTACGCGAGCTGGG

CGAAAAGCCGATCCACCATCACCAGAAACACCAACCTGAACACGGTGACT

CTGAAAATGACCAGTCTGACAGCCGCGGACACGGCCACTTATTTCTGTGC

GAGAAGAAGTGATGTTGGTACTTCTGTGGGTTTTGATTCCTGGGGCCCAG

GCACCCTGGCACCGTCTCCCTCCCTCTTATCCAGCGTCTGGGGGAGGGCA

CGGGGAGTAGGAGCTGCGGGCCTGTGAGATGTTCGGCAGGGGCTCTTTCT

ACCGGGGTGCTGTGGGAGAGATGTGAAGTCGGCACGCACATTGAGTGGCT

GGAGGTTATACCGTCCTGGTGAGTGAGTTATGCTGGAATTGGAACTCCTC

CACCGACTAATAGACTATA

Single Primer: RVH2
(SEQ ID NO: 33)
5' AGTCGGTGAAGGAGTCCGAG 3'

\>HI-SF23-VH2_G10 SC1-3
(SEQ ID NO: 32)
AANCACGCATACACTGACCTCACCTGTACAGCCTCTGGGTTCTCCCTCAG

TGAGGCATGGAGTGATCTGGGTCCGCCAGGCTCCAGGGAAGGGGCTGGAA

TGGATCGGAAGTGCTGGCGCTTATGGTAGAATATACTACGCGAGCTGGGC

GAAAAGCCGATCCACCATCACCAGAAACACCAACCTGAACACGGTGACTC

TGAAAATGACCAGTCTGACAGCCGCGGACACGGCCACTTATTTCTGTGCG

AGAAGAAGTGATGTTGGTACTTCTGTGGGTTTTGATTCCTGGGGCCCAGG

CACCCTGCCTCCGTCTCTGAGATGGCTCCGTCGGGGACTTCGGTGGGGTA

GGATAAAGGACCAGGTGGTCAAGCAGTTTGTTGTCGATTCTGTAGGGGAC

GGCGGAAGGAGTTGGGTGGGCACGAGGCGGATCTTGGGGGGGGGACCAG

CTGGGGATCGGCGGGGGGATCCCTTGATTGAGCGCCCAAGTAGGATTGA

GATAAATTCTGTGTATGTAGAAGCGACTTCTAGCCTCCAGCACCCGTGCT

CGATTTTAAGATTGAAGCTGAGCTTTTTGGTG

SC50-3 Heavy Chain

Pooled VH primers - VHP:
\>HI-SF27-VHP_C11
(SEQ ID NO: 34)
NNCGCCTGGGATCGTAGAGCATCATCTCTCAGGCAGATGACGGGGTTACT

CCTGATGTGCTTCTAGAGACTGGGCCCTGCTCGCTCCCGGGGAGGGCCTG

GAATGGATCGGAAGTGCTGGTGCATATGGTAGAATATATTACCCAAACTG

GGCGAGAAGCCGAGCCACCATCACCAGAAACACCAACCTCAACACGGTGT

CTCTGAAAATGACCAGTCTGACAGCCGCGGACACGGCCACTTATTTCTGT

GCGAGAAGGACGAATGTTAGTACTTCTGTGGGTTTTGATTCCTGGGGACC

AGGCACCCTGGTCTCCGTCTCTTAAA

Single Primer: RVH2
(SEQ ID NO: 36)
5' AGTCGGTGAAGGAGTCCGAG 3'

\>HI-SF35-VH2_C12
(SEQ ID NO: 35)
GGGCTGAGCACGCATACACTGACCTCACCTGCACAGCCTCTGGGTTCTCC

CTCAATGGCTATGGAGTGATCTGGGTCCGCCAGGCTCCAGGGAAGGGCCT

GGAATGGATCGGAAGTGCTGGTGCATATGGTAGAATATATTACCCAAACT

GGGCGAGAAGCCGAGCCACCATCACCAGAAACACCAACCTCAACACGGTG

TCTCTGAAAATGACCAGTCTGACAGCCGCGGACACGGCCACTTATTTCTG

TGCGAGAAGGACGAATGTTAGTACTTCTGTGGGTTTTGATTCCTGGGGAC

CAGGCACCCTGCACCCGTCTCCCATACCTACTCAGTGTCTGTAACCGTCG

GGGGGGGGGGGATGGAACCAGGCGGCAAAGCGGAACGTAACTCGAAAAG

TGTACGGCCGGTGGTGCAGGCAGTCCCGGCAGCAGTGGAACCGCTGGGAG

GGACCAAGATGCTGGCTAAGGGAAAGGTTCCCGGTCATGGACAGCGCTGT

GTTCTACTCCCTGGTCACCATCTCCTAGAGAGG

SC1-1 Light Chain kappa

Pooled VL kappa primers - VKP
RHFabVκ1_A
(SEQ ID NO: 37)
5' GTGATGACCCAGACTCCA 3'

RHFabVκ1_C
(SEQ ID NO: 38)
5' GTGCTGACCCAGACTCCA 3'

RHFabVκ2_A
(SEQ ID NO: 39)
5' GATATGACCCAGACTCCA 3'

RHFabVκ2_C
(SEQ ID NO: 40)
5' GATCTGACCCAGACTCCA 3'

\>HI-SF1-VKP_A08 SC1-1
(SEQ ID NO: 41)
CCTATCAGCTGGTAGACAGTCACCATCATTGCCAGGCCAGTGAGAGCGTT

TATAGTAACAACCGCTTATCCTGGTTTCAGCAGAAACCAGGGCAGCCTCC

CAAACTCCTGATCTATCTGGTATCCACTCTGGCATCTGGGGTCCCATCGC

GATTCAAAGGCAGTGGATCTGGGACACAATTCACTCTCACCATTAGCGAT

GTGGTGTGTGACGATGCTGCCACTTACTACTGTGTAGGCTATAAAGTAG

TACCACTGATGGTTTGGCTTTCGGCGGAGGGACCGATGGATTGGTCAAAA

AACTGTGGTGGTGCGGGTATGTTGCCGGCGGGTAGTAGATGGCAGGGTCG

TGAGCACCAGACAGAAGGAAAGGGAAATTAAGGGAAGGACACGCCAAAGG

GAGGGGCGGGTATGGAGGGCAGAAAGGAGGTAGATTATATGTGGATGGGG

AGTAATGGGTTTGTTTGTAGTGAAAAAAGGAGGAGTCTTTTTTTTTTTAA

GAAAGCCACCTGCCCGAATTGGGGTGTGGTCGTTTTTCGCCCGGGGACGG

GATGTTGAAAGAGGAGTGCACCGGCTCCAAAAAAGCTGGATAGAGGATGT

TTGTTTTCGAAGTGTGGCGCTAGGAGACT

```
Primers VK2:
RHFabVκ2_A
                                         (SEQ ID NO: 42)
5' GATATGACCCAGACTCCA 3'

RHFabVκ2_C
                                         (SEQ ID NO: 43)
5' GATCTGACCCAGACTCCA 3'

>HI-SF8-VK2_H08 SC1-1
                                         (SEQ ID NO: 44)
```
GNCNGNCTGTGGTAGACAGTCACCATCATTGCCAGGCCAGTGAGAGCGTT

TATAGTAACAACCGCTTATCCTGGTTTCAGCAGAAACCAGGGCAGCCTCC

CAAACTCCTGATCTATCTGGTATCCACTCTGGCATCTGGGGTCCCATCGC

GATTCAAAGGCAGTGGATCTGGGACACAATTCACTCTCACCATTAGCGAT

GTGGTGTGTGACGATGCTGCCACTTACTACTGTGTAGGCTATAAAAGTAG

TACCACTGATGGTTTGGCTTTCGGCGGAGGGACCGACGGCGGATCCTAAA

AGCGGATGAGGCGACGGCATCTACACTTGCTCCGGTTAGTCAGAGGCGGT

TACCTTAGAAAACCAAACATTACGAGCTGGCGACTAAGGACAAGGGTTGT

GCTCGGCGCGGGACTTAGCCCACCAGCTCAGGACACCAGTATGACGACGC

CCATGCTGCATCTGTGTTCGAGTGCACCAAATGCACTAATCCATCTCTTG

AAAGTTATCGACATGTGAAAGGCCAGGTAACGTTATACGGCTTGCAACAC

AAATAGACTCGCGCACGCCGCGGCTCGTCCGTCACATCTTAATAACTTT

CAGATACAGTATTGCGACCGTAGCTCAGCTGACGCCAAGTTAACCATGCT

AGCTGCGAAACTGAGGTGCATAATATGATCGCGACATCCACTTCGGGATC

GGTTAGGGGTGGACTACGAGCTCAAGTCTAAATCCAGCGTTGTAACCCCA

CATGT

SC1-3 Light Chain kappa

```
Pooled VL kappa primers - VKP
>HI-SF13-VKP_E09 SC1-3
                                         (SEQ ID NO: 45)
```
TNTTTCTGTGGTAGACAGTCACCATCAATTGCCAGGCCAGTGAGAGCGTT

TATAGTAACAACCGCTTATCCTGGTTTCAGCAGAAACCAGGGCAGCCTCC

CAAACTCCTGATCTATCTGGTATCCACTCTGGCATCTGGGGTCCCATCGC

GATTCAAAGGCAGTGGATCTGGGACACAATTCACTCTCACCATTAGCGAT

GTGGTGTGTGACGATGCTGCCACTTACTACTGTGTAGGCTATAAAAGTAG

TACCACTGATGGTTTGGCTTTCGGCGGAGGGACCGAGGGAGGGGTCAAAA

AAAACATGTGGGCTACTTTTTATACAGTTCGGTAGTAGTGGCATCATCTG

ACACACCAGACTAATGTTTGAATGTTAATTGTGTCTAATACGATGGTTTA

AGGGGGGGGCCCCATTCGGAACGTAAAAAAAGAGCATGAGGAGTTTGAG

AAGGTGAATGGTTATTTCATTAACGAGAAAGGCGTCGGTTACTTAAA

```
Primers VK2:
RHFabVκ2_A
                                         (SEQ ID NO: 46)
5' GATATGACCCAGACTCCA 3'

RHFabVκ2_C
                                         (SEQ ID NO: 47)
5' GATCTGACCCAGACTCCA 3'

>HI-SF21-VK2_E10
                                         (SEQ ID NO: 48)
```
GACCTGTTCTCTGGTAGACAGTCACCATCAATTGCCAGGCCAGTGAGAGC

GTTTATAGTAACAACCGCTTATCCTGGTTTCAGCAGAAACCAGGGCAGCC

TCCCAAACTCCTGATCTATCTGGTATCCACTCTGGCATCTGGGGTCCCAT

CGCGATTCAAAGGCAGTGGATCTGGGACACAATTCACTCTCACCATTAGC

GATGTGGTGTGTGACGATGCTGCCACTTACTACTGTGTAGGCTATAAAAG

TAGTACCACTGATGGTTTGGCTTTCGGCGGAGGGACCGAGGGGGTGGTCA

AAAAAGGTTCCGCCC

SC50-3 Light Chain kappa

```
Pooled VL kappa primers - VKP
>HI-SF25-VKP_A11
                                         (SEQ ID NO: 49)
```
ACTGTCATGTGGTAGTCAGTCACCATCAATTGCCAGGCCAGTGAGACCGT

TTATAATAATGACCGCTTAGCCTGGTTTCAACAGAAACCAGGGCAGCCTC

CCAAGCTCCTGATCTATCTGGCATCCACTCTGCCATCTGGGGTCCCATCG

CGATTCAAAGGCAGTGGATCTGGGACACAGTTCACTCTCACCATTAGTGA

TGTGGGGTGTGATGATGCTGCCACTTATTATTGTGTAGGCTATAAAAGTA

GTACGACTGATGGTTTGGCTTTCGGCGGAGGGACCGAGGGGTTGGTCAAA

ACAACACGTTGTGTACTACTTTTATAACCTACACAATAATAAGTGGCAGC

ATCATCACACACGTAAAAATGGTGAGAGGGAACTGGGGTCCAAAACCTGC

CTTTGAATCGGATGGGACCAGATTGAGAGTGGAAGCAGATGAGATAGGAG

GGGGGGAAGGCGCTCGCTTTTTTTTTAAACCGGCCCGGGACCTTTTATAT

ATAAAAAAATTCTTTCACGGGGAATTGTGATGGGGAAAGAAACCCCCCCG

GGACAAAACTGTGGAGGAGGGAACTTGGGGGGCCCACCCAAGG

```
Primers VK1:
RHFabVκ1_A
                                         (SEQ ID NO: 50)
5' GTGATGACCCAGACTCCA 3'

RHFabVκ1_C
                                         (SEQ ID NO: 51)
5' GTGCTGACCCAGACTCCA 3'

>HI-SF29-VK_1E11
                                         (SEQ ID NO: 52)
```
GNCTNTTCTGTGGTAGTCAGTCACCATCAATTGCCAGGCCAGTGAGACCG

TTTATAATAATGACCGCTTAGCCTGGTTTCAACAGAAACCAGGGCAGCCT

CCCAAGCTCCTGATCTATCTGGCATCCACTCTGCCATCTGGGGTCCCATC

GCGATTCAAAGGCAGTGGATCTGGGACACAGTTCACTCTCACCATTAGTG

ATGTGGGGTGTGATGATGCTGCCACTTATTATTGTGTAGGCTATAAAAGT

AGTACGACTGATGGTTTGGCTTTCGGCGGAGGGACCGAGTGGCAGATCCT

AAAACAGCCCTGCAGGAGGGGGAACGTTGGTCATGCTCGGACGGGGAGT

-continued

```
GGGGCTGCCAAAGGAGTCTGATAGAGGAAAGGCTCCTGTAAAGGGGAAT

TGGCGTGGGAAGTGGGTAAGCCATCTGACGGGAATGACAAGAAGTTTCTT

ATGAAGGGGAGTGAAGTGTTGTAATTGAAGCATCGGCAAAATCACCCTAA

GATTATAGAGCTGATGAGAGAGTTGTAGAGTAGGCTCGCCGGG
```

EXAMPLE 4

VH Chain Translations

>HI-SF3-VHP_C08 SC1-1 GOOD SEQ
(SEQ ID NO: 53)
QSMIIFS*ADHDGYSSSAPSLWVLLAPCQGLEWIGSAGAYCRISYASWAK
SRSTITRNTNLNTVTLKMTSLTSADTATYFCARRSDVGTSVGFDSWGPGT
LVTVSLPFICLTPPAAPKNRKGGGRYSLGSGGGGLWGCRPGRPLSAARRG
FYGSVLVGNWGIYIGAMSRISDFSFGLLRCEKE*STGSILCH*VWVSRGA
SDTAPLGIS

>HI-SF11-VH2_C09
(SEQ ID NO: 54)
L*HGYTDLTCTASGFSLSGHGVIWVRQAPGKGLEWIGSAGAYGRIYYASW
AKSRSTITRNTNLNTVTLKMTSLTAADTATYFCARRSDVGTSVGFDSWGP
GTLVTVSL

>HI-SF15-VHP_G09 SC1-3 GOOD SEQ
(SEQ ID NO: 55)
RTYDHHALR*ITALLLIGYKMSWVLLAPCKGLEWIGSAGAYGRIYYASWA
KSRSTITRNTNLNTVTLKMTSLTAADTATYFCARRSDVGTSVGFDSWGPG
TLAPSPSLLSSVWGRARGVGAAGL*DVRQGLFLPGCCGRDVKSARTLSGW
RLYRPGE*VMLELELLHRLIDY

>HI-SF23-VH2_G10 SC1-3 GOOD SEQ
(SEQ ID NO: 56)
THTLTSPVQPLGSPSVRHGVIWVRQAPGKGLEWIGSAGAYGRIYYASWAK
SRSTITRNTNLNTVTLKMTSLTAADTATYFCARRSDVGTSVGFDSWGPGT
LPPSLRWLRRGLRWGRIKDQVVKQFVVDSVGDGGRSWVGTRRILGGGTSW
GSGGGIP*LSAQVGLR*ILCM*KRLLASSTRARF*D*S*AFW

>HI-SF27-VHP_C11 SC50-3 GOOD SEQ
(SEQ ID NO: 57)
PGIVEHHLSGR*RGYS*CASRDWALLAPGEGLEWIGSAGAYGRIYYPNWA
RSRATITRNTNLNTVSLKMTSLTAADTATYFCARRTNVSTSVGFDSWGPG
TLVSVS*

>HI-SF35-VH2_C12 SC50-3 GOOD SEQ
(SEQ ID NO: 58)
AEHAYTDLTCTASGFSLNGYGVIWVRQAPGKGLEWIGSAGAYGRIYYPNW
ARSRATITRNTNLNTVSLKMTSLTAADTATYFCARRTNVSTSVGFDSWGP
GTLHPSPIPTQCL*PSGGGGMEPGGKAERNSKSVRPVVQAVPAAVEPLGG
TKMLAKGKVPGHGQRCVLLPGHHLLER

>HI-SF10-VH1_B09
(SEQ ID NO: 59)
SGDHSAYEQQHDVDQDGPLDLRHPGHRLSRLHDVLLCWHFVLNITHAAGK
GGNGPRLLGPVTLVTLSLTSLTAADTATYFCARRSDVGTSVGFDSWGPGT
LVTVSLGPPLADVQVRQGHQLLGLQDVPQGHFQPRLPVHQVWAPRAQGVP
GGDASLQDHISCRPGLLPRLTTTTK

>HI-SF12-VH3_D09
(SEQ ID NO: 60)
IASVPRSSAGRLMCPPSMG*AWTLAGGAWGEPWPGTTSCRVDTTLPSGTL
VTVSSTITRNTNLNTVTLKMTSLTAADTATYFCARRSDVGTSVGFDSWGP
GTLAPSLY*PFPYSCRLSLRPGHCHPLAPGRPLMDHDRTRAAGHPCYHPP
HRQVGGLPAELQPA*ALPIRGEAQLLLSPPWYLACELAHSHHGKWGPGSP
GSEALAPVWIRTGWKLLDGGFWEHQLQRDPYGGGT*PPTVSTDTVTVAGS
AGMAPSIAWKSCAPAGIHILCLVW

>HI-SF22-VH1_F10 SC1-3
(SEQ ID NO: 61)
MSCVTKLMSSSTTLTRYGPLDLRHPGHRLSKLHDVLLFVHRVLIMTHAAV
MGGNGPRLLGPGTLVTVSLTSLTAADTATYFCARRSDVGTSVGFDSWGPG
TLVTVSLSPSLLDVHVRQGHHLLGLQHVPQGHFQPRLPVHQV*ARRAQGV
PGGDANLQDHISCWPGLHHLLTT

>HI-SF24-VH3_H10 SC1-3
(SEQ ID NO: 62)
ALGSLILTSQEEGPPWIG*TWEMAGGPWGKPLTGSQAWGGHHFA*RHPGH
HLIRITRNTNLNTVTLKMTSLTAADTATYFCARRSDVGTSVGFDSWGPGT
LVTVSLLTPPLLLPHLSTSCCCHPLAPGSPLMDLDRTRAAGRPCYHPRVR
RSVDFLLNSRLRKHYPSVGNPLLLSRPWYLACDLAHSHHGKWGPGSPGSD
ALLPVCIIKGWKPRDGGFREPSSA

>HI-SF34-VH1_B 12 SC50-3
(SEQ ID NO: 63)
VFAHVSLAFEQQHDVDQVWSSGSQAPWSPSPKAWCGAHVLAPRA*HDPRC
LDGRKQPHATGPCQPGVPQLTSLTAADTATYFCARRTNVSTSVGFDSWGP
GTLVTVSYTTTASRCTRSTRPPPARAATCSSRALSTTATCAPSVSSARTR
SAWR*CQPAGSHLLQTWTPPPTEY

VL Chain Translations

>HI-SF1-VKP_A08 SC1-1
(SEQ ID NO: 64)
YQLVDSHHHCQASESVYSNNRLSWFQQKPGQPPKLLIYLVSTLASGVPSR
FKGSGSGTQFTLTISDVVCDDAATYYCVGYKSSTTDGLAFGGGTDGLVKK
LWWCGYVAGG**MAGS*APDRRKGKLREGHAKGRGGYGGQKGGRLYVDGE
*WVCL**KKEESFFF*ESHLPELGCGRFSPGDGMLKEECTGSKKAG*RMF
VFEVWR*ET

>HI-SF5-VK1_E08
(SEQ ID NO: 65)
S*WKTVTINCQASESVYSNNRLSWFQQKPGQPPKLLIYLVSTLASGVPSR
FKGSGSGTQFTLTISDVVCDDAATYYCVGYKSSTTDGLAFGGGTDGNPKM
KDMGDGSRRCSGCRRR*ARVPGLPVATKDKGKVVAGVSRVDRNSSGRLDA
VLCVLVDDCQIHILKMFHLSSFVSFVC

>HI-SF6-VK1_F08
(SEQ ID NO: 66)
VVTVTINCQASESVYSNNRLSWFQQKPGQPPKLLIYLVSTLASGVPSRFK
GSGSGTQFTLTISDVVCDDAATYYCVGYKSSTTDGLAFGGGTEGMVKKSG

-continued
```
GGALMPYG*SGRIVTLTVQDRAGHADDKGHAVALAAAVGS*DPDSAKDGN

SALVILRRKDRSLS*DVRRLHRVLDSVTTRRPARPARPHPMSLKSFPVPT

RLAYAAVDKSPCLLHG
```

>HI-SF8-VK2_H08
(SEQ ID NO: 67)
```
VVDSHHHCQASESVYSNNRLSWFQQKPGQPPKLLIYLVSTLASGVPSRFK

GSGSGTQFTLTISDVVCDDAATYYCVGYKSSTTDGLAFGGGTDG#GS*KR

MRRRHLHLLRLVRGGYLRKPNITSWRLRTRVVLGAGLSPPAQDTSMTTPM

LHLCSSAPNALIHLLKVIDM*KAR*RYTACNTNRLAHAAARAVTS**LSD

TVLRP*LS*RQVNHASCETEVHNMIATSTSGSVRGGLRAQV*IQRCNPTC
```

>HI-SF9-VK2_A09
(SEQ ID NO: 68)
```
QMGDSHHHCQASESVYSNNRLSWFQQKPGQPPKLLIYLVSTLASGVPSRF

KGSGSGTQFTLTISDVVCDDAATYYCVGYKSSTTDGLAFGGGTEGWSKKR

VPCQ*SPAGTKWAHRYTHQ*GWRKCV
```

>HI-SF13-VKP_E09 SC1-3
(SEQ ID NO: 69)
```
FLW*TVTINCQASESVYSNNRLSWFQQKPGQPPKLLIYLVSTLASGVPSR

FKGSGSGTQFTLTISDVVCDDAATYYCVGYKSSTTDGLAFGGGTEGGVKK

TCGLLFIQFGSKWHHLTHQTNV*MLIVSNTMV*GGGPHSERKKRA*GV*E

GEWLFH*PRKASVT*
```

>HI-SF17-VK1_A10
(SEQ ID NO: 70)
```
S*WETVTINCQASESVYSNNRLSWFQQKPGQPPKLLIYLVSTLASGVPSR

FKGSGSGTQFTLTISDVVCDDAATYYCVGYKSSTTDGLAFGGGTDGIS*N
```

>HI-SF18-VK1_B10
(SEQ ID NO: 71)
```
LVLRGASHHHCQASESVYSNNRLSWFQQKPGQPPKLLIYLVSTLASGVPS

RFKGSGSGTQFTLTISDVVCDDAATYYCVGYKSNTTDGLAFGGGTEVVVK

KD
```

>HI-SF20-VK2_D10
(SEQ ID NO: 72)
```
LFMLGDSHHHCQASESVYSNNRLSWFQQKPGQPPKLLIYLVSTLASGVPS

RFKGSGSGTQFTLTISDVVCDDAATYYCVGYKSSTTDGLAFGGGTELEIL

KAPP
```

>HI-SF21-VK2_E10
(SEQ ID NO: 73)
```
PVLW*TVTINCQASESVYSNNRLSWFQQKPGQPPKLLIYLVSTLASGVPS

RFKGSGSGTQFTLTISDVVCDDAATYYCVGYKSSTTDGLAFGGGTEGVVK

KGSA
```

>HI-SF25-VKP_A11 SC50-3
(SEQ ID NO: 74)
```
TVMW*SVTINCQASETVYNNDRLAWFQQKPGQPPKLLIYLASTLPSGVPS

RFKGSGSGTQFTLTISDVGCDDAATYYCVGYKSSTTDGLAFGGGTEGLVK

TTRCVLLL*PTQ**VAASSHT*KW*EGTGVQNLPLNRMGPD*EWKQMR*E

GGKALAFELNRPGTFYI*KNSFTGNCDGERNPPGTKLWRRELGGPTQ
```

>HI-SF29-VK1_E11 SC50-3
(SEQ ID NO: 75)
```
LW*SVTINCQASETVYNNDRLAWFQQKPGQPPKLLIYLASTLPSGVPSRF

KGSGSGTQFTLTISDVGCDDAATYYCVGYKSSTTDGLAFGGGTEWQILKQ

PCRRGERWSCSDGEWGCQRSLIEERLL*RGNWRGKWVSHLTGMTRSFL*R

GVKCCN*SIGKITLRL*S**ESCRVGSP
```

>HI-SF30-VK1_F11 SC50-3
(SEQ ID NO: 76)
```
CLWQSVTINCQASETVYNNDRLAWFQQKPGQPPKLITYLASTLPSGVPSR

FKGSGSGTQFTLTISDVGCDDAATYYCVGYKSSTTDGLAFGGGTDGVVKT

IWSVWGGGLCIILGSGVTPQ*SLTGLMP*S*GGNGLGRECAR*HERKKK*

VHRHCIVWSQAGDLLYNEAIPYDREVQYAPGGNCYKRNLVSKQHH
```

>HI-SF33-VK2_A12 SC50-3
(SEQ ID NO: 77)
```
TVQWESVTINCQASETVYNNDRLAWFQQKPGQPPKLLIYLASTLPSGVPS

RFKGSGSGTQFTLTISDVGCDDAATYYCVGYKSSTTDGLAFGGGTEGVVK

K
```

>HI-SF32-VK2_H11 SC50-3
(SEQ ID NO: 78)
```
CS*WESVTINCQASETVYNNDRLPGFNRNQGSLPSS*SIWHPLCHLGSHR

DSKAVDLGHSSLSPLVMWGVMMLPLIIV*AIKVVRLMVWLSAEGPTADPK

TGV*GSRWEWGQGERSGETRL*GGL
```

---

What is claimed is:

1. An isolated monoclonal antibody, a humanized form thereof, chimeric form thereof, or an antigen-binding fragment thereof, wherein the monoclonal antibody, humanized form, chimeric form or antigen binding fragment comprises a heavy chain variable domain and a light chain variable domain, wherein:
   a) the heavy chain and light chain variable domains are produced by a hybridoma having ATCC accession No. PTA 121685; or
   b) the heavy chain and the light chain variable domains are produced by a hybridoma having ATCC accession No. PTA 121686,
   and wherein the monoclonal antibody, humanized form, chimeric form or antigen binding fragment thereof specifically binds a polypeptide comprising a histidine when the histidine is phosphorylated at position N1 of the imidazole ring, but does not specifically bind the polypeptide when the histidine is not phosphorylated at position N1 of the imidazole ring.

2. The isolated monoclonal antibody of claim 1, wherein the antibody is recombinant.

3. A hybridoma producing the monoclonal antibody of claim 1.

4. The isolated monoclonal antibody, humanized form, chimeric form, or antigen binding fragment of claim 1, conjugated to a label.

5. The isolated monoclonal antibody, humanized form, chimeric form, or antigen binding fragment of claim 4, wherein the label is a radiolabel, an enzyme or a fluorescent label.

6. The isolated monoclonal antibody, humanized form, chimeric form, or antigen binding fragment of claim 4, conjugated to a solid support.

7. The isolated antigen binding fragment of claim 1, wherein the antigen binding fragment is a Fab, Fab', F(ab')2, Fv, a disulfide-linked Fv, a single-chain Fv (scFv), or an sc(Fv)$_2$.

8. A diabody or polyspecific antibody comprising the monoclonal antibody, humanized form, chimeric form, or antigen binding fragment of claim 1.

9. A method for detecting a polypeptide comprising a phosphohistidine, comprising:
   a) contacting a sample comprising a polypeptide with the monoclonal antibody, humanized form, chimeric form, or antigen binding fragment of claim 1; and
   b) detecting binding of the monoclonal antibody, humanized form, chimeric form, or antigen binding fragment to the polypeptide in the sample to form an immune complex, wherein the presence of the immune complex indicates the presence of the polypeptide comprising a histidine phosphorylated at position N1.

10. The method of claim 9, wherein the monoclonal antibody, humanized form, chimeric form, or antigen binding fragment is labeled.

11. The method of claim 9, wherein the monoclonal antibody, humanized form, chimeric form, or antigen binding fragment is conjugated to a solid support.

12. The method of claim 11, wherein the label is a radiolabel, enzyme or fluorescent label.

13. A solid support conjugated to the monoclonal antibody of claim 1.

14. The solid support of claim 13, wherein the solid support is polystyrene or latex.

15. A composition comprising the monoclonal antibody of claim 1, humanized form thereof, or chimeric form thereof, or antigen binding fragment thereof, and a physiologically acceptable carrier.

16. The composition of claim 15, wherein the monoclonal antibody, humanized form thereof, chimeric form thereof, or antigen binding fragment thereof is labeled.

17. The composition of claim 16, wherein the label is a radiolabel, an enzyme or a fluorescent label.

* * * * *

SEQUENCE LISTING

```
<160> NUMBER OF SEQ ID NOS: 82

<210> SEQ ID NO 1
<211> LENGTH: 4
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(4)
<223> OTHER INFORMATION: Xaa can be any naturally occurring amino acid

<400> SEQUENCE: 1

Xaa Xaa Xaa Xaa
1
```

```
<210> SEQ ID NO 2
<211> LENGTH: 5
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(5)
<223> OTHER INFORMATION: Xaa can be any naturally occurring amino acid

<400> SEQUENCE: 2

Xaa Xaa Xaa Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(6)
<223> OTHER INFORMATION: Xaa can be any naturally occurring amino acid

<400> SEQUENCE: 3

Xaa Xaa Xaa Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(7)
<223> OTHER INFORMATION: Xaa can be any naturally occurring amino acid

<400> SEQUENCE: 4

Xaa Xaa Xaa Xaa Xaa Xaa Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(8)
<223> OTHER INFORMATION: Xaa can be any naturally occurring amino acid

<400> SEQUENCE: 5

Xaa Xaa Xaa Xaa Xaa Xaa Xaa Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(4)
<223> OTHER INFORMATION: Xaa can be any naturally occurring amino acid
```

```
<400> SEQUENCE: 6

Xaa Xaa Xaa Xaa
1

<210> SEQ ID NO 7
<211> LENGTH: 5
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(5)
<223> OTHER INFORMATION: Xaa can be any naturally occurring amino acid

<400> SEQUENCE: 7

Xaa Xaa Xaa Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(6)
<223> OTHER INFORMATION: Xaa can be any naturally occurring amino acid

<400> SEQUENCE: 8

Xaa Xaa Xaa Xaa Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(7)
<223> OTHER INFORMATION: Xaa can be any naturally occurring amino acid

<400> SEQUENCE: 9

Xaa Xaa Xaa Xaa Xaa Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: amino acid sequence for antibody generation
<220> FEATURE:
<221> NAME/KEY: misc_feature
<222> LOCATION: (1)..(8)
<223> OTHER INFORMATION: Xaa can be any naturally occurring amino acid

<400> SEQUENCE: 10

Xaa Xaa Xaa Xaa Xaa Xaa Xaa Xaa
1               5

<210> SEQ ID NO 11
<211> LENGTH: 152
<212> TYPE: PRT
<213> ORGANISM: Homo sapiens
```

<400> SEQUENCE: 11

Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150

<210> SEQ ID NO 12
<211> LENGTH: 152
<212> TYPE: PRT
<213> ORGANISM: Mus musculus

<400> SEQUENCE: 12

Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile His Leu Trp Phe Lys Pro Glu Glu Leu Ile Asp Tyr Lys Ser
    130                 135                 140

Cys Ala His Asp Trp Val Tyr Glu
145                 150

<210> SEQ ID NO 13
<211> LENGTH: 152
<212> TYPE: PRT
<213> ORGANISM: Homo sapiens

<400> SEQUENCE: 13

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
            130                 135                 140

Cys Ala Gln Asn Trp Ile Tyr Glu
145                 150

<210> SEQ ID NO 14
<211> LENGTH: 152
<212> TYPE: PRT
<213> ORGANISM: Mus musculus

<400> SEQUENCE: 14

Met Ala Asn Ser Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Leu Gln Ala Ser Glu Asp Leu Leu
            35                  40                  45

Lys Glu His Tyr Thr Asp Leu Lys Asp Arg Pro Phe Phe Thr Gly Leu
50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
            115                 120                 125

Glu Ile Ser Leu Trp Phe Gln Pro Glu Glu Leu Val Glu Tyr Lys Ser
            130                 135                 140

Cys Ala Gln Asn Trp Ile Tyr Glu
145                 150

<210> SEQ ID NO 15
<211> LENGTH: 30
<212> TYPE: DNA
<213> ORGANISM: Artificial Sequence
<220> FEATURE:
<223> OTHER INFORMATION: PCR primer

<400> SEQUENCE: 15
gatcggatcc atggccaact gtgagcgtac                              30

```
<210> SEQ ID NO 16
<211> LENGTH: 31
<212> TYPE: DNA
<213> ORGANISM: Artificial Sequence
<220> FEATURE:
<223> OTHER INFORMATION: PCR primer

<400> SEQUENCE: 16
gatcgaattc tcattcatag atccagttct c                              31

<210> SEQ ID NO 17
<211> LENGTH: 31
<212> TYPE: DNA
<213> ORGANISM: Artificial Sequence
<220> FEATURE:
<223> OTHER INFORMATION: PCR primer

<400> SEQUENCE: 17
gatcggatcc atggccgcct acaaactggt g                              31

<210> SEQ ID NO 18
<211> LENGTH: 31
<212> TYPE: DNA
<213> ORGANISM: Artificial Sequence
<220> FEATURE:
<223> OTHER INFORMATION: PCR primer

<400> SEQUENCE: 18
gatcgaattc tcacttcttg gccttgccct g                              31

<210> SEQ ID NO 19
<211> LENGTH: 20
<212> TYPE: DNA
<213> ORGANISM: Artificial Sequence
<220> FEATURE:
<223> OTHER INFORMATION: pcr primer

<400> SEQUENCE: 19
agtcggtgga ggagtccagg                                           20

<210> SEQ ID NO 20
<211> LENGTH: 20
<212> TYPE: DNA
<213> ORGANISM: Artificial Sequence
<220> FEATURE:
<223> OTHER INFORMATION: pcr primer

<400> SEQUENCE: 20
agtcggtgga ggagtccggg                                           20

<210> SEQ ID NO 21
<211> LENGTH: 20
<212> TYPE: DNA
<213> ORGANISM: Artificial Sequence
<220> FEATURE:
<223> OTHER INFORMATION: pcr primer

<400> SEQUENCE: 21
agtcggtgaa ggagtccgag                                           20

<210> SEQ ID NO 22
<211> LENGTH: 20
<212> TYPE: DNA
<213> ORGANISM: Artificial Sequence
<220> FEATURE:
```

<223> OTHER INFORMATION: pcr primer

<400> SEQUENCE: 22
agtcgctgga ggagtccggg                                              20

<210> SEQ ID NO 23
<211> LENGTH: 20
<212> TYPE: DNA
<213> ORGANISM: Artificial Sequence
<220> FEATURE:
<223> OTHER INFORMATION: pcr primer

<400> SEQUENCE: 23
agtcgttgga ggagtccggg                                              20

<210> SEQ ID NO 24
<211> LENGTH: 22
<212> TYPE: DNA
<213> ORGANISM: Artificial Sequence
<220> FEATURE:
<223> OTHER INFORMATION: pcr primer

<400> SEQUENCE: 24
agcagcagct gatggagtcc gg                                           22

<210> SEQ ID NO 25
<211> LENGTH: 22
<212> TYPE: DNA
<213> ORGANISM: Artificial Sequence
<220> FEATURE:
<223> OTHER INFORMATION: pcr primer

<400> SEQUENCE: 25
aggagcagct gatggagtcc gg                                           22

<210> SEQ ID NO 26
<211> LENGTH: 22
<212> TYPE: DNA
<213> ORGANISM: Artificial Sequence
<220> FEATURE:
<223> OTHER INFORMATION: pcr primer

<400> SEQUENCE: 26
agcagcagct ggtggagtcc gg                                           22

<210> SEQ ID NO 27
<211> LENGTH: 22
<212> TYPE: DNA
<213> ORGANISM: Artificial Sequence
<220> FEATURE:
<223> OTHER INFORMATION: pcr primer

<400> SEQUENCE: 27
aggagcagct ggtggagtcc gg                                           22

<210> SEQ ID NO 28
<211> LENGTH: 742
<212> TYPE: DNA
<213> ORGANISM: Oryctolagus cuniculus

<400> SEQUENCE: 28
cctgggggga gccttggccc gggacaacta gctgcagggt ggacaccact ttgcctagcg    60
gcaccctggt caccgtctct tccaccatca ccagaaacac caacctgaac acggtgactc   120
tgaaaatgac cagtctgaca gccgcggaca cggccactta tttctgtgcg agaagaagtg   180

-continued

```
atgttggtac ttctgtgggt tttgattcct ggggcccagg caccctggca ccgtctctct    240
attgaccatt cccctactct tgccgcctct ctctacgtcc tgggcactgc cacccgctgg    300
cccctggccg tccgctaatg gaccacgacc gcactcgggc tgctggccat ccctgttatc    360
atccacccca tcgacaggtc ggtggacttc ctgctgaact ccagcctgcg taagctctac    420
ccatccgtgg ggaagcccag ctcctcctga gcccaccctg gtacctggcc tgcgagttgg    480
ctcactccca ccatgggaag tgggggccag gctccccggg gtctgaggcc ctggcacctg    540
tgtggattag aactggatgg aagcttctag atggggtttt ctgggagcat cagctgcagc    600
gagacccata cggaggcggg acctgacccc caactgtctc cacggacact gtgacagtgg    660
cggggagtgc ggggatggcg ccatccatag catggaagtc ctgtgctccc gcggggatac    720
atatcttatg cctggtatgg ag    742

<210> SEQ ID NO 29
<211> LENGTH: 631
<212> TYPE: DNA
<213> ORGANISM: Oryctolagus cuniculus
<220> FEATURE:
<221> NAME/KEY: misc_feature
<222> LOCATION: (2)..(3)
<223> OTHER INFORMATION: n is a, c, g, or t

<400> SEQUENCE: 29
gnncaaagta tgatcatctt ctcttaggca gatcacgacg gttactcctc atctgctcct    60
agtctctggg tcctcctcgc tccatgtcag gggctggaat ggatcggaag tgctggcgct    120
tattgtagaa tatcctacgc gagctgggcg aaaagccgat ccaccatcac cagaaacacc    180
aacctgaaca cggtgactct gaaaatgacc agtctgacat ccgcggacac ggccacttat    240
ttctgtgcga gaagaagtga tgttggtact tctgtgggtt ttgattcctg ggcccaggc    300 accctggtca ccgtctctct accttttatc tgcctgactc cacccgctgc ttcctaaaaa    360
tcgaaaaggg gggggccggt acagtttggg gtcgggaggg ggggtctgt ggggatgtcg    420 gccaggtagg ccattgtccg ctgcccgacg agggttttat gggtcggtgt tagtcgggaa    480
ttggggtatc tacataggcg caatgagtag aatctctgat ttttcttttg ggttgttgcg    540
gtgcgagaaa gaatagtcca ccggatcgat cctgtgtcat tgagtttggg tgagtcgagg    600
tgcttccgat actgctcccc taggcatctc a    631

<210> SEQ ID NO 30
<211> LENGTH: 20
<212> TYPE: DNA
<213> ORGANISM: Oryctolagus cuniculus

<400> SEQUENCE: 30
agtcggtgaa ggagtccgag    20

<210> SEQ ID NO 31
<211> LENGTH: 519
<212> TYPE: DNA
<213> ORGANISM: Oryctolagus cuniculus

<400> SEQUENCE: 31
ggcgtacgta tgatcatcac gctcttaggt agatcacggc gttactcctc atcggctaca    60
aaatgtcctg ggtcctgctc gctccatgta aggggctgga atggatcgga agtgctggcg    120
cttatggtag aatatactac gcgagctggg cgaaaagccg atccaccatc accagaaaca    180
```

```
ccaacctgaa cacggtgact ctgaaaatga ccagtctgac agccgcggac acggccactt    240
atttctgtgc gagaagaagt gatgttggta cttctgtggg ttttgattcc tggggcccag    300
gcaccctggc accgtctccc tccctcttat ccagcgtctg ggggagggca cggggagtag    360
gagctgcggg cctgtgagat gttcggcagg ggctctttct accggggtgc tgtgggagag    420
atgtgaagtc ggcacgcaca ttgagtggct ggaggttata ccgtcctggt gagtgagtta    480
tgctggaatt ggaactcctc caccgactaa tagactata                          519

<210> SEQ ID NO 32
<211> LENGTH: 582
<212> TYPE: DNA
<213> ORGANISM: Oryctolagus cuniculus
<220> FEATURE:
<221> NAME/KEY: misc_feature
<222> LOCATION: (3)..(3)
<223> OTHER INFORMATION: n is a, c, g, or t

<400> SEQUENCE: 32
aancacgcat acactgacct cacctgtaca gcctctgggt tctccctcag tgaggcatgg     60
agtgatctgg gtccgccagg ctccagggaa ggggctggaa tggatcggaa gtgctggcgc    120
ttatggtaga atatactacg cgagctgggc gaaaagccga tccaccatca ccagaaacac    180
caacctgaac acggtgactc tgaaaatgac cagtctgaca gccgcggaca cggccactta    240
tttctgtgcg agaagaagtg atgttggtac ttctgtgggt tttgattcct ggggcccagg    300
caccctgcct ccgtctctga gatggctccg tcggggactt cggtggggta ggataaagga    360
ccaggtggtc aagcagtttg ttgtcgattc tgtaggggac ggcggaagga gttgggtggg    420
cacgaggcgg atcttggggg ggggaccag ctggggatcg gcgggggga tcccttgatt    480 gagcgcccaa gtaggattga gataaattct gtgtatgtag aagcgacttc tagcctccag    540 caccccgtgct cgattttaag attgaagctg agcttttggg tg                     582

<210> SEQ ID NO 33
<211> LENGTH: 20
<212> TYPE: DNA
<213> ORGANISM: Oryctolagus cuniculus

<400> SEQUENCE: 33
agtcggtgaa ggagtccgag                                                20

<210> SEQ ID NO 34
<211> LENGTH: 326
<212> TYPE: DNA
<213> ORGANISM: Oryctolagus cuniculus
<220> FEATURE:
<221> NAME/KEY: misc_feature
<222> LOCATION: (1)..(2)
<223> OTHER INFORMATION: n is a, c, g, or t

<400> SEQUENCE: 34
nncgcctggg atcgtagagc atcatctctc aggcagatga cggggttact cctgatgtgc     60
ttctagagac tgggccctgc tcgctcccgg ggagggcctg gaatggatcg gaagtgctgg    120
tgcatatggt agaatatatt acccaaactg ggcgagaagc cgagccacca tcaccagaaa    180
caccaacctc aacacggtgt ctctgaaaat gaccagtctg acagccgcgg acacggccac    240
ttatttctgt gcgagaagga cgaatgttag tacttctgtg ggttttgatt cctggggacc    300
aggcaccctg gtctccgtct cttaaa                                         326
```

```
<210> SEQ ID NO 35
<211> LENGTH: 533
<212> TYPE: DNA
<213> ORGANISM: Oryctolagus cuniculus

<400> SEQUENCE: 35
gggctgagca cgcatacact gacctcacct gcacagcctc tgggttctcc ctcaatggct      60
atggagtgat ctgggtccgc caggctccag ggaagggcct ggaatggatc ggaagtgctg     120
gtgcatatgg tagaatatat taccaaaact gggcgagaag ccgagccacc atcaccagaa     180
acaccaacct caacacggtg tctctgaaaa tgaccagtct gacagccgcg gacacggcca     240
cttatttctg tgcgagaagg acgaatgtta gtacttctgt gggttttgat tcctggggac     300
caggcaccct gcaccgtctc ccataccta ctcagtgtct gtaaccgtcg ggggggggg      360 ggatggaacc aggcggcaaa gcggaacgta actcgaaaag tgtacggccg gtggtgcagg     420
cagtcccggc agcagtggaa ccgctgggag ggaccaagat gctggctaag ggaaaggttc     480
ccggtcatgg acagcgctgt gttctactcc ctggtcacca tctcctagag agg            533

<210> SEQ ID NO 36
<211> LENGTH: 20
<212> TYPE: DNA
<213> ORGANISM: Oryctolagus cuniculus

<400> SEQUENCE: 36
agtcggtgaa ggagtccgag                                                  20

<210> SEQ ID NO 37
<211> LENGTH: 18
<212> TYPE: DNA
<213> ORGANISM: Artificial Sequence
<220> FEATURE:
<223> OTHER INFORMATION: sequence primer

<400> SEQUENCE: 37
gtgatgaccc agactcca                                                    18

<210> SEQ ID NO 38
<211> LENGTH: 18
<212> TYPE: DNA
<213> ORGANISM: Artificial Sequence
<220> FEATURE:
<223> OTHER INFORMATION: sequence primer

<400> SEQUENCE: 38
gtgctgaccc agactcca                                                    18

<210> SEQ ID NO 39
<211> LENGTH: 18
<212> TYPE: DNA
<213> ORGANISM: Artificial Sequence
<220> FEATURE:
<223> OTHER INFORMATION: sequence primer

<400> SEQUENCE: 39
gatatgaccc agactcca                                                    18

<210> SEQ ID NO 40
<211> LENGTH: 18
<212> TYPE: DNA
<213> ORGANISM: Artificial Sequence
<220> FEATURE:
<223> OTHER INFORMATION: sequence primer
```

```
<400> SEQUENCE: 40
gatctgaccc agactcca                                                 18

<210> SEQ ID NO 41
<211> LENGTH: 629
<212> TYPE: DNA
<213> ORGANISM: Oryctolagus cuniculus

<400> SEQUENCE: 41
cctatcagct ggtagacagt caccatcatt gccaggccag tgagagcgtt tatagtaaca    60
accgcttatc ctggtttcag cagaaaccag ggcagcctcc caaactcctg atctatctgg   120
tatccactct ggcatctggg gtcccatcgc gattcaaagg cagtggatct gggacacaat   180
tcactctcac cattagcgat gtggtgtgtg acgatgctgc cacttactac tgtgtaggct   240
ataaaagtag taccactgat ggtttggctt tcggcggagg gaccgatgga ttggtcaaaa   300
aactgtggtg gtgcgggtat gttgccggcg ggtagtagat ggcagggtcg tgagcaccag   360
acagaaggaa agggaaatta agggaaggac acgccaaagg gaggggcggg tatggagggc   420
agaaaggagg tagattatat gtggatgggg agtaatgggt ttgtttgtag tgaaaaaagg   480
aggagtcttt ttttttttaa gaaagccacc tgcccgaatt ggggtgtggt cgttttcgc    540 ccggggacgg gatgttgaaa gaggagtgca ccggctccaa aaaagctgga tagaggatgt   600
ttgttttcga agtgtggcgc taggagact                                     629

<210> SEQ ID NO 42
<211> LENGTH: 18
<212> TYPE: DNA
<213> ORGANISM: Artificial Sequence
<220> FEATURE:
<223> OTHER INFORMATION: sequence primer

<400> SEQUENCE: 42
gatatgaccc agactcca                                                 18

<210> SEQ ID NO 43
<211> LENGTH: 18
<212> TYPE: DNA
<213> ORGANISM: Artificial Sequence
<220> FEATURE:
<223> OTHER INFORMATION: sequence primer

<400> SEQUENCE: 43
gatctgaccc agactcca                                                 18

<210> SEQ ID NO 44
<211> LENGTH: 755
<212> TYPE: DNA
<213> ORGANISM: Oryctolagus cuniculus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 44
gncngnctgt ggtagacagt caccatcatt gccaggccag tgagagcgtt tatagtaaca    60
```

```
accgcttatc ctggtttcag cagaaaccag ggcagcctcc caaactcctg atctatctgg    120
tatccactct ggcatctggg gtcccatcgc gattcaaagg cagtggatct gggacacaat    180
tcactctcac cattagcgat gtggtgtgtg acgatgctgc cacttactac tgtgtaggct    240
ataaaagtag taccactgat ggtttggctt tcggcggagg gaccgacggc ggatcctaaa    300
agcggatgag gcgacggcat ctacacttgc tccggttagt cagaggcggt taccttagaa    360
aaccaaacat tacgagctgg cgactaagga caagggttgt gctcggcgcg ggacttagcc    420
caccagctca ggacaccagt atgacgacgc ccatgctgca tctgtgttcg agtgcaccaa    480
atgcactaat ccatctcttg aaagttatcg acatgtgaaa ggccaggtaa cgttatacgg    540
cttgcaacac aaatagactc gcgcacgccg cggctcgtgc cgtcacatct taataacttt    600
cagatacagt attgcgaccg tagctcagct gacgccaagt taaccatgct agctgcgaaa    660
ctgaggtgca taatatgatc gcgacatcca cttcgggatc ggttaggggt ggactacgag    720
ctcaagtcta aatccagcgt tgtaaccccca catgt                              755

<210> SEQ ID NO 45
<211> LENGTH: 498
<212> TYPE: DNA
<213> ORGANISM: Oryctolagus cuniculus
<220> FEATURE:
<221> NAME/KEY: misc_feature
<222> LOCATION: (2)..(2)
<223> OTHER INFORMATION: n is a, c, g, or t

<400> SEQUENCE: 45
tntttctgtg gtagacagtc accatcaatt gccaggccag tgagagcgtt tatagtaaca     60
accgcttatc ctggtttcag cagaaaccag ggcagcctcc caaactcctg atctatctgg    120
tatccactct ggcatctggg gtcccatcgc gattcaaagg cagtggatct gggacacaat    180
tcactctcac cattagcgat gtggtgtgtg acgatgctgc cacttactac tgtgtaggct    240
ataaaagtag taccactgat ggtttggctt tcggcggagg gaccgaggga ggggtcaaaa    300
aaacatgtgg gctacttttt atacagttcg gtagtaagtg gcatcatctg acacaccaga    360
ctaatgtttg aatgttaatt gtgtctaata cgatggttta aggggggggg ccccattcgg    420
aacgtaaaaa aagagcatga ggagtttgag aaggtgaatg gttatttcat taaccgagaa    480
aggcgtcggt tacttaaa                                                  498

<210> SEQ ID NO 46
<211> LENGTH: 18
<212> TYPE: DNA
<213> ORGANISM: Artificial Sequence
<220> FEATURE:
<223> OTHER INFORMATION: sequence primer

<400> SEQUENCE: 46
gatatgaccc agactcca                                                   18

<210> SEQ ID NO 47
<211> LENGTH: 18
<212> TYPE: DNA
<213> ORGANISM: Artificial Sequence
<220> FEATURE:
<223> OTHER INFORMATION: Sequence primer

<400> SEQUENCE: 47
gatctgaccc agactcca                                                   18
```

<210> SEQ ID NO 48
<211> LENGTH: 315
<212> TYPE: DNA
<213> ORGANISM: Oryctolagus cuniculus

<400> SEQUENCE: 48
gacctgttct ctggtagaca gtcaccatca attgccaggc cagtgagagc gtttatagta      60
acaaccgctt atcctggttt cagcagaaac cagggcagcc tcccaaactc ctgatctatc     120
tggtatccac tctggcatct ggggtcccat cgcgattcaa aggcagtgga tctgggacac     180
aattcactct caccattagc gatgtggtgt gtgacgatgc tgccacttac tactgtgtag     240
gctataaaag tagtaccact gatggtttgg ctttcggcgg agggaccgag ggggtggtca     300
aaaaaggttc cgccc                                                       315

<210> SEQ ID NO 49
<211> LENGTH: 593
<212> TYPE: DNA
<213> ORGANISM: Oryctolagus cuniculus

<400> SEQUENCE: 49
actgtcatgt ggtagtcagt caccatcaat tgccaggcca gtgagaccgt ttataataat      60
gaccgcttag cctggtttca acagaaacca gggcagcctc ccaagctcct gatctatctg     120
gcatccactc tgccatctgg ggtcccatcg cgattcaaag cagtggatc tgggacacag      180 ttcactctca ccattagtga tgtggggtgt gatgatgctg ccacttatta ttgtgtaggc     240
tataaaagta gtacgactga tggtttggct ttcggcggag ggaccgaggg gttggtcaaa     300
acaacacgtt gtgtactact tttataacct acacaataat aagtggcagc atcatcacac     360
acgtaaaaat ggtgagaggg aactggggtc caaaacctgc ctttgaatcg gatgggacca     420
gattgagagt ggaagcagat gagataggag gggggaagg cgctcgcttt tttttttaaac     480 cggcccggga cctttttatat ataaaaaaat tctttcacgg ggaattgtga tgggaaaga    540 aaccccccg ggacaaaact gtggaggagg gaacttgggg ggcccaccca agg             593

<210> SEQ ID NO 50
<211> LENGTH: 18
<212> TYPE: DNA
<213> ORGANISM: Artificial Sequence
<220> FEATURE:
<223> OTHER INFORMATION: sequence primer

<400> SEQUENCE: 50
gtgatgaccc agactcca                                                    18

<210> SEQ ID NO 51
<211> LENGTH: 18
<212> TYPE: DNA
<213> ORGANISM: Artificial Sequence
<220> FEATURE:
<223> OTHER INFORMATION: sequence primer

<400> SEQUENCE: 51
gtgctgaccc agactcca                                                    18

<210> SEQ ID NO 52
<211> LENGTH: 543
<212> TYPE: DNA
<213> ORGANISM: Oryctolagus cuniculus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 52

```
gnctnttctg tggtagtcag tcaccatcaa ttgccaggcc agtgagaccg tttataataa    60
tgaccgctta gcctggtttc aacagaaacc agggcagcct cccaagctcc tgatctatct   120
ggcatccact ctgccatctg ggtcccatc  gcgattcaaa ggcagtggat ctgggacaca   180
gttcactctc accattagtg atgtggggtg tgatgatgct gccacttatt attgtgtagg   240
ctataaaagt agtacgactg atggtttggc tttcggcgga gggaccgagt ggcagatcct   300
aaaacagccc tgcaggaggg gggaacgttg gtcatgctcg acggggagt  ggggctgcca   360
aaggagtctg atagaggaaa ggctcctgta aagggggaat tggcgtggga agtgggtaag   420
ccatctgacg ggaatgacaa gaagtttctt atgaagggga gtgaagtgtt gtaattgaag   480
catcggcaaa atcaccctaa gattatagag ctgatgagag agttgtagag taggctcgcc   540
ggg                                                                 543
```

<210> SEQ ID NO 53
<211> LENGTH: 104
<212> TYPE: PRT
<213> ORGANISM: Oryctolagus cuniculus

<400> SEQUENCE: 53

```
Leu Phe Met Leu Gly Asp Ser His His His Cys Gln Ala Ser Glu Ser
1               5                   10                  15

Val Tyr Ser Asn Asn Arg Leu Ser Trp Phe Gln Gln Lys Pro Gly Gln
            20                  25                  30

Pro Pro Lys Leu Leu Ile Tyr Leu Val Ser Thr Leu Ala Ser Gly Val
        35                  40                  45

Pro Ser Arg Phe Lys Gly Ser Gly Ser Gly Thr Gln Phe Thr Leu Thr
    50                  55                  60

Ile Ser Asp Val Val Cys Asp Asp Ala Ala Thr Tyr Tyr Cys Val Gly
65                  70                  75                  80

Tyr Lys Ser Ser Thr Thr Asp Gly Leu Ala Phe Gly Gly Gly Thr Glu
                85                  90                  95

Leu Glu Ile Leu Lys Ala Pro Pro
            100
```

<210> SEQ ID NO 54
<211> LENGTH: 209
<212> TYPE: PRT
<213> ORGANISM: Oryctolagus cuniculus
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid

<400> SEQUENCE: 54

Gln Ser Met Ile Ile Phe Ser Xaa Ala Asp His Asp Gly Tyr Ser Ser

```
                1               5                   10                  15
            Ser Ala Pro Ser Leu Trp Val Leu Leu Ala Pro Cys Gln Gly Leu Glu
                            20                  25                  30

Trp Ile Gly Ser Ala Gly Ala Tyr Cys Arg Ile Ser Tyr Ala Ser Trp
                            35                  40                  45

Ala Lys Ser Arg Ser Thr Ile Thr Arg Asn Thr Asn Leu Asn Thr Val
                50                  55                  60

Thr Leu Lys Met Thr Ser Leu Thr Ser Ala Asp Thr Ala Thr Tyr Phe
            65                  70                  75                  80

Cys Ala Arg Arg Ser Asp Val Gly Thr Ser Val Gly Phe Asp Ser Trp
                            85                  90                  95

Gly Pro Gly Thr Leu Val Thr Val Ser Leu Pro Phe Ile Cys Leu Thr
                            100                 105                 110

Pro Pro Ala Ala Pro Lys Asn Arg Lys Gly Gly Gly Arg Tyr Ser Leu
                            115                 120                 125

Gly Ser Gly Gly Gly Leu Trp Gly Cys Arg Pro Gly Arg Pro Leu
            130                 135                 140

Ser Ala Ala Arg Arg Gly Phe Tyr Gly Ser Val Leu Val Gly Asn Trp
            145                 150                 155                 160

Gly Ile Tyr Ile Gly Ala Met Ser Arg Ile Ser Asp Phe Ser Phe Gly
                            165                 170                 175

Leu Leu Arg Cys Glu Lys Glu Xaa Ser Thr Gly Ser Ile Leu Cys His
                            180                 185                 190

Xaa Val Trp Val Ser Arg Gly Ala Ser Asp Thr Ala Pro Leu Gly Ile
                            195                 200                 205

Ser

<210> SEQ ID NO 55
            <211> LENGTH: 108
            <212> TYPE: PRT
            <213> ORGANISM: Oryctolagus cuniculus
            <220> FEATURE:
            <221> NAME/KEY: misc_feature
            <222> LOCATION: (2)..(2)
            <223> OTHER INFORMATION: Xaa can be any naturally occurring amino acid

<400> SEQUENCE: 55

Leu Xaa His Gly Tyr Thr Asp Leu Thr Cys Thr Ala Ser Gly Phe Ser
            1               5                   10                  15

Leu Ser Gly His Gly Val Ile Trp Val Arg Gln Ala Pro Gly Lys Gly
                            20                  25                  30

Leu Glu Trp Ile Gly Ser Ala Gly Ala Tyr Gly Arg Ile Tyr Tyr Ala
                            35                  40                  45

Ser Trp Ala Lys Ser Arg Ser Thr Ile Thr Arg Asn Thr Asn Leu Asn
                50                  55                  60

Thr Val Thr Leu Lys Met Thr Ser Leu Thr Ala Ala Asp Thr Ala Thr
            65                  70                  75                  80

Tyr Phe Cys Ala Arg Arg Ser Asp Val Gly Thr Ser Val Gly Phe Asp
                            85                  90                  95

Ser Trp Gly Pro Gly Thr Leu Val Thr Val Ser Leu
                            100                 105

<210> SEQ ID NO 56
            <211> LENGTH: 172
            <212> TYPE: PRT
            <213> ORGANISM: Oryctolagus cuniculus
            <220> FEATURE:
```

<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid

<400> SEQUENCE: 56

```
Arg Thr Tyr Asp His His Ala Leu Arg Xaa Ile Thr Ala Leu Leu Leu
1               5                   10                  15

Ile Gly Tyr Lys Met Ser Trp Val Leu Leu Ala Pro Cys Lys Gly Leu
            20                  25                  30

Glu Trp Ile Gly Ser Ala Gly Ala Tyr Gly Arg Ile Tyr Tyr Ala Ser
        35                  40                  45

Trp Ala Lys Ser Arg Ser Thr Ile Thr Arg Asn Thr Asn Leu Asn Thr
    50                  55                  60

Val Thr Leu Lys Met Thr Ser Leu Thr Ala Ala Asp Thr Ala Thr Tyr
65                  70                  75                  80

Phe Cys Ala Arg Arg Ser Asp Val Gly Thr Ser Val Gly Phe Asp Ser
                85                  90                  95

Trp Gly Pro Gly Thr Leu Ala Pro Ser Pro Ser Leu Ser Ser Val
            100                 105                 110

Trp Gly Arg Ala Arg Gly Val Gly Ala Ala Gly Leu Xaa Asp Val Arg
        115                 120                 125

Gln Gly Leu Phe Leu Pro Gly Cys Cys Gly Arg Asp Val Lys Ser Ala
    130                 135                 140

Arg Thr Leu Ser Gly Trp Arg Leu Tyr Arg Pro Gly Glu Xaa Val Met
145                 150                 155                 160

Leu Glu Leu Glu Leu Leu His Arg Leu Ile Asp Tyr
                165                 170
```

<210> SEQ ID NO 57
<211> LENGTH: 192
<212> TYPE: PRT
<213> ORGANISM: Oryctolagus cuniculus
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid

<400> SEQUENCE: 57

```
Thr His Thr Leu Thr Ser Pro Val Gln Pro Leu Gly Ser Pro Ser Val
1               5                   10                  15

Arg His Gly Val Ile Trp Val Arg Gln Ala Pro Gly Lys Gly Leu Glu
            20                  25                  30

Trp Ile Gly Ser Ala Gly Ala Tyr Gly Arg Ile Tyr Tyr Ala Ser Trp
            35                  40                  45

Ala Lys Ser Arg Ser Thr Ile Thr Arg Asn Thr Asn Leu Asn Thr Val
    50                  55                  60

Thr Leu Lys Met Thr Ser Leu Thr Ala Ala Asp Thr Ala Thr Tyr Phe
65                  70                  75                  80

Cys Ala Arg Arg Ser Asp Val Gly Thr Ser Val Gly Phe Asp Ser Trp
                85                  90                  95

Gly Pro Gly Thr Leu Pro Pro Ser Leu Arg Trp Leu Arg Arg Gly Leu
            100                 105                 110

Arg Trp Gly Arg Ile Lys Asp Gln Val Val Lys Gln Phe Val Val Asp
            115                 120                 125

Ser Val Gly Asp Gly Gly Arg Ser Trp Val Gly Thr Arg Ile Leu
130                 135                 140

Gly Gly Gly Thr Ser Trp Gly Ser Gly Gly Ile Pro Xaa Leu Ser
145                 150                 155                 160

Ala Gln Val Gly Leu Arg Xaa Ile Leu Cys Met Xaa Lys Arg Leu Leu
            165                 170                 175

Ala Ser Ser Thr Arg Ala Arg Phe Xaa Asp Xaa Ser Xaa Ala Phe Trp
            180                 185                 190

<210> SEQ ID NO 58
<211> LENGTH: 107
<212> TYPE: PRT
<213> ORGANISM: Oryctolagus cuniculus
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 58

Pro Gly Ile Val Glu His His Leu Ser Gly Arg Xaa Arg Gly Tyr Ser
1               5                   10                  15

Xaa Cys Ala Ser Arg Asp Trp Ala Leu Leu Ala Pro Gly Glu Gly Leu
            20                  25                  30

Glu Trp Ile Gly Ser Ala Gly Ala Tyr Gly Arg Ile Tyr Tyr Pro Asn
            35                  40                  45

Trp Ala Arg Ser Arg Ala Thr Ile Thr Arg Asn Thr Asn Leu Asn Thr
    50                  55                  60

Val Ser Leu Lys Met Thr Ser Leu Thr Ala Ala Asp Thr Ala Thr Tyr
65                  70                  75                  80

Phe Cys Ala Arg Arg Thr Asn Val Ser Thr Ser Val Gly Phe Asp Ser
                85                  90                  95

Trp Gly Pro Gly Thr Leu Val Ser Val Ser Xaa
            100                 105

<210> SEQ ID NO 59
```

```
<211> LENGTH: 177
<212> TYPE: PRT
<213> ORGANISM: Oryctolagus cuniculus
<220> FEATURE:
<221> NAME/KEY: misc_feature
<222> LOCATION: (114)..(114)
<223> OTHER INFORMATION: Xaa can be any naturally occurring amino acid

<400> SEQUENCE: 59

Ala Glu His Ala Tyr Thr Asp Leu Thr Cys Thr Ala Ser Gly Phe Ser
1               5                   10                  15

Leu Asn Gly Tyr Gly Val Ile Trp Val Arg Gln Ala Pro Gly Lys Gly
            20                  25                  30

Leu Glu Trp Ile Gly Ser Ala Gly Ala Tyr Gly Arg Ile Tyr Tyr Pro
        35                  40                  45

Asn Trp Ala Arg Ser Arg Ala Thr Ile Thr Arg Asn Thr Asn Leu Asn
    50                  55                  60

Thr Val Ser Leu Lys Met Thr Ser Leu Thr Ala Ala Asp Thr Ala Thr
65                  70                  75                  80

Tyr Phe Cys Ala Arg Arg Thr Asn Val Ser Thr Val Gly Phe Asp
                85                  90                  95

Ser Trp Gly Pro Gly Thr Leu His Pro Ser Pro Ile Pro Thr Gln Cys
            100                 105                 110

Leu Xaa Pro Ser Gly Gly Gly Met Glu Pro Gly Gly Lys Ala Glu
            115                 120                 125

Arg Asn Ser Lys Ser Val Arg Pro Val Val Gln Ala Val Pro Ala Ala
130                 135                 140

Val Glu Pro Leu Gly Gly Thr Lys Met Leu Ala Lys Gly Lys Val Pro
145                 150                 155                 160

Gly His Gly Gln Arg Cys Val Leu Leu Pro Gly His His Leu Leu Glu
                165                 170                 175

Arg

<210> SEQ ID NO 60
<211> LENGTH: 175
<212> TYPE: PRT
<213> ORGANISM: Oryctolagus cuniculus

<400> SEQUENCE: 60

Ser Gly Asp His Ser Ala Tyr Glu Gln Gln His Asp Val Asp Gln Asp
1               5                   10                  15

Gly Pro Leu Asp Leu Arg His Pro Gly His Arg Leu Ser Arg Leu His
            20                  25                  30

Asp Val Leu Leu Cys Trp His Phe Val Leu Asn Ile Thr His Ala Ala
        35                  40                  45

Gly Lys Gly Gly Asn Gly Pro Arg Leu Leu Gly Pro Val Thr Leu Val
    50                  55                  60

Thr Leu Ser Leu Thr Ser Leu Thr Ala Ala Asp Thr Ala Thr Tyr Phe
65                  70                  75                  80

Cys Ala Arg Arg Ser Asp Val Gly Thr Ser Val Gly Phe Asp Ser Trp
                85                  90                  95

Gly Pro Gly Thr Leu Val Thr Val Ser Leu Gly Pro Leu Ala Asp
            100                 105                 110

Val Gln Val Arg Gln Gly His Gln Leu Leu Gly Leu Gln Asp Val Pro
        115                 120                 125

Gln Gly His Phe Gln Pro Arg Leu Pro Val His Gln Val Trp Ala Pro
    130                 135                 140
```

Arg Ala Gln Gly Val Pro Gly Gly Asp Ala Ser Leu Gln Asp His Ile
145                 150                 155                 160

Ser Cys Arg Pro Gly Leu Leu Pro Arg Leu Thr Thr Thr Lys
                165                 170                 175

<210> SEQ ID NO 61
<211> LENGTH: 274
<212> TYPE: PRT
<213> ORGANISM: Oryctolagus cuniculus
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid

<400> SEQUENCE: 61

Ile Ala Ser Val Pro Arg Ser Ser Ala Gly Arg Leu Met Cys Pro Pro
1               5                   10                  15

Ser Met Gly Xaa Ala Trp Thr Leu Ala Gly Gly Ala Trp Gly Glu Pro
                20                  25                  30

Trp Pro Gly Thr Thr Ser Cys Arg Val Asp Thr Thr Leu Pro Ser Gly
            35                  40                  45

Thr Leu Val Thr Val Ser Ser Thr Ile Thr Arg Asn Thr Asn Leu Asn
        50                  55                  60

Thr Val Thr Leu Lys Met Thr Ser Leu Thr Ala Ala Asp Thr Ala Thr
65                  70                  75                  80

Tyr Phe Cys Ala Arg Arg Ser Asp Val Gly Thr Ser Val Gly Phe Asp
                85                  90                  95

Ser Trp Gly Pro Gly Thr Leu Ala Pro Ser Leu Tyr Xaa Pro Phe Pro
            100                 105                 110

Tyr Ser Cys Arg Leu Ser Leu Arg Pro Gly His Cys His Pro Leu Ala
        115                 120                 125

Pro Gly Arg Pro Leu Met Asp His Asp Arg Thr Arg Ala Ala Gly His
130                 135                 140

Pro Cys Tyr His Pro Pro His Arg Gln Val Gly Gly Leu Pro Ala Glu
                145                 150                 155                 160

Leu Gln Pro Ala Xaa Ala Leu Pro Ile Arg Gly Glu Ala Gln Leu Leu
                165                 170                 175

Leu Ser Pro Pro Trp Tyr Leu Ala Cys Glu Leu Ala His Ser His His
            180                 185                 190

Gly Lys Trp Gly Pro Gly Ser Pro Gly Ser Glu Ala Leu Ala Pro Val
        195                 200                 205

Trp Ile Arg Thr Gly Trp Lys Leu Leu Asp Gly Gly Phe Trp Glu His
    210                 215                 220

Gln Leu Gln Arg Asp Pro Tyr Gly Gly Gly Thr Xaa Pro Pro Thr Val
225                 230                 235                 240

Ser Thr Asp Thr Val Thr Val Ala Gly Ser Ala Gly Met Ala Pro Ser
                245                 250                 255

Ile Ala Trp Lys Ser Cys Ala Pro Gly Ile His Ile Leu Cys Leu
                260                 265                 270

Val Trp

<210> SEQ ID NO 62
<211> LENGTH: 173
<212> TYPE: PRT
<213> ORGANISM: Oryctolagus cuniculus
<220> FEATURE:
<221> NAME/KEY: misc_feature
<222> LOCATION: (143)..(143)
<223> OTHER INFORMATION: Xaa can be any naturally occurring amino acid

<400> SEQUENCE: 62

Met Ser Cys Val Thr Lys Leu Met Ser Ser Thr Thr Leu Thr Arg
1               5                   10                  15

Tyr Gly Pro Leu Asp Leu Arg His Pro Gly His Arg Leu Ser Lys Leu
                20                  25                  30

His Asp Val Leu Leu Phe Val His Arg Val Leu Ile Met Thr His Ala
            35                  40                  45

Ala Val Met Gly Gly Asn Gly Pro Arg Leu Leu Gly Pro Gly Thr Leu
        50                  55                  60

Val Thr Val Ser Leu Thr Ser Leu Thr Ala Ala Asp Thr Ala Thr Tyr
65                  70                  75                  80

Phe Cys Ala Arg Arg Ser Asp Val Gly Thr Ser Val Gly Phe Asp Ser
                85                  90                  95

Trp Gly Pro Gly Thr Leu Val Thr Val Ser Leu Ser Pro Ser Leu Leu
                100                 105                 110

Asp Val His Val Arg Gln Gly His His Leu Leu Gly Leu Gln His Val
            115                 120                 125

Pro Gln Gly His Phe Gln Pro Arg Leu Pro Val His Gln Val Xaa Ala
        130                 135                 140

Arg Arg Ala Gln Gly Val Pro Gly Gly Asp Ala Asn Leu Gln Asp His
145                 150                 155                 160

Ile Ser Cys Trp Pro Gly Leu His His Leu Leu Thr Thr
                165                 170

<210> SEQ ID NO 63
<211> LENGTH: 224
<212> TYPE: PRT
<213> ORGANISM: Oryctolagus cuniculus
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 63

Ala Leu Gly Ser Leu Ile Leu Thr Ser Gln Glu Glu Gly Pro Pro Trp
1               5                   10                  15

Ile Gly Xaa Thr Trp Glu Met Ala Gly Gly Pro Trp Gly Lys Pro Leu
                20                  25                  30

Thr Gly Ser Gln Ala Trp Gly Gly His His Phe Ala Xaa Arg His Pro
            35                  40                  45

Gly His His Leu Ile Arg Ile Thr Arg Asn Thr Asn Leu Asn Thr Val
        50                  55                  60

Thr Leu Lys Met Thr Ser Leu Thr Ala Ala Asp Thr Ala Thr Tyr Phe

```
                65                  70                  75                  80
Cys Ala Arg Arg Ser Asp Val Gly Thr Ser Val Gly Phe Asp Ser Trp
                    85                  90                  95
Gly Pro Gly Thr Leu Val Thr Val Ser Leu Leu Thr Pro Pro Leu Leu
                100                 105                 110
Leu Pro His Leu Ser Thr Ser Cys Cys His Pro Leu Ala Pro Gly
                115                 120                 125
Ser Pro Leu Met Asp Leu Asp Arg Thr Arg Ala Ala Gly Arg Pro Cys
130                 135                 140
Tyr His Pro Arg Val Arg Arg Ser Val Asp Phe Leu Leu Asn Ser Arg
145                 150                 155                 160
Leu Arg Lys His Tyr Pro Ser Val Gly Asn Pro Leu Leu Ser Arg
                165                 170                 175
Pro Trp Tyr Leu Ala Cys Asp Leu Ala His Ser His His Gly Lys Trp
                180                 185                 190
Gly Pro Gly Ser Pro Gly Ser Asp Ala Leu Leu Pro Val Cys Ile Ile
                195                 200                 205
Lys Gly Trp Lys Pro Arg Asp Gly Gly Phe Arg Glu Pro Ser Ser Ala
210                 215                 220
```

<210> SEQ ID NO 64
<211> LENGTH: 174
<212> TYPE: PRT
<213> ORGANISM: Oryctolagus cuniculus
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid

<400> SEQUENCE: 64

```
Val Phe Ala His Val Ser Leu Ala Phe Glu Gln Gln His Asp Val Asp
1               5                   10                  15
Gln Val Trp Ser Ser Gly Ser Gln Ala Pro Trp Ser Pro Ser Pro Lys
                20                  25                  30
Ala Trp Cys Gly Ala His Val Leu Ala Pro Arg Ala Xaa His Asp Pro
                35                  40                  45
Arg Cys Leu Asp Gly Arg Lys Gln Pro His Ala Thr Gly Pro Cys Gln
50                  55                  60
Pro Gly Val Pro Gln Leu Thr Ser Leu Thr Ala Ala Asp Thr Ala Thr
65                  70                  75                  80
Tyr Phe Cys Ala Arg Arg Thr Asn Val Ser Thr Ser Val Gly Phe Asp
                85                  90                  95
Ser Trp Gly Pro Gly Thr Leu Val Thr Val Ser Tyr Thr Thr Thr Ala
                100                 105                 110
Ser Arg Cys Thr Arg Ser Thr Arg Pro Pro Ala Arg Ala Ala Thr
                115                 120                 125
Cys Ser Ser Arg Ala Leu Ser Thr Thr Ala Cys Ala Pro Ser Val
130                 135                 140
Ser Ser Ala Arg Thr Arg Ser Ala Trp Arg Xaa Cys Gln Pro Ala Gly
145                 150                 155                 160
Ser His Leu Leu Gln Thr Trp Thr Pro Pro Thr Glu Tyr
                165                 170
```

-continued

```
<210> SEQ ID NO 65
<211> LENGTH: 209
<212> TYPE: PRT
<213> ORGANISM: Oryctolagus cuniculus
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid

<400> SEQUENCE: 65

Tyr Gln Leu Val Asp Ser His His Cys Gln Ala Ser Glu Ser Val
1               5                   10                  15

Tyr Ser Asn Asn Arg Leu Ser Trp Phe Gln Gln Lys Pro Gly Gln Pro
                20                  25                  30

Pro Lys Leu Leu Ile Tyr Leu Val Ser Thr Leu Ala Ser Gly Val Pro
            35                  40                  45

Ser Arg Phe Lys Gly Ser Gly Ser Gly Thr Gln Phe Thr Leu Thr Ile
        50                  55                  60

Ser Asp Val Val Cys Asp Asp Ala Ala Thr Tyr Tyr Cys Val Gly Tyr
65                  70                  75                  80

Lys Ser Ser Thr Thr Asp Gly Leu Ala Phe Gly Gly Gly Thr Asp Gly
                85                  90                  95

Leu Val Lys Lys Leu Trp Trp Cys Gly Tyr Val Ala Gly Gly Xaa Xaa
                100                 105                 110

Met Ala Gly Ser Xaa Ala Pro Asp Arg Arg Lys Gly Lys Leu Arg Glu
            115                 120                 125

Gly His Ala Lys Gly Arg Gly Tyr Gly Gly Gln Lys Gly Gly Arg
        130                 135                 140

Leu Tyr Val Asp Gly Glu Xaa Trp Val Cys Leu Xaa Xaa Lys Lys Glu
145                 150                 155                 160

Glu Ser Phe Phe Phe Xaa Glu Ser His Leu Pro Glu Leu Gly Cys Gly
                165                 170                 175

Arg Phe Ser Pro Gly Asp Gly Met Leu Lys Glu Glu Cys Thr Gly Ser
            180                 185                 190

Lys Lys Ala Gly Xaa Arg Met Phe Val Phe Glu Val Trp Arg Xaa Glu
        195                 200                 205

Thr

<210> SEQ ID NO 66
<211> LENGTH: 177
```

```
<212> TYPE: PRT
<213> ORGANISM: Oryctolagus cuniculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid

<400> SEQUENCE: 66

Ser Xaa Trp Lys Thr Val Thr Ile Asn Cys Gln Ala Ser Glu Ser Val
1               5                   10                  15

Tyr Ser Asn Asn Arg Leu Ser Trp Phe Gln Gln Lys Pro Gly Gln Pro
            20                  25                  30

Pro Lys Leu Leu Ile Tyr Leu Val Ser Thr Leu Ala Ser Gly Val Pro
        35                  40                  45

Ser Arg Phe Lys Gly Ser Gly Ser Gly Thr Gln Phe Thr Leu Thr Ile
50                  55                  60

Ser Asp Val Val Cys Asp Asp Ala Ala Thr Tyr Tyr Cys Val Gly Tyr
65                  70                  75                  80

Lys Ser Ser Thr Thr Asp Gly Leu Ala Phe Gly Gly Gly Thr Asp Gly
                85                  90                  95

Asn Pro Lys Met Lys Asp Met Gly Asp Gly Ser Arg Arg Cys Ser Gly
            100                 105                 110

Cys Arg Arg Arg Xaa Ala Arg Val Pro Gly Leu Pro Val Ala Thr Lys
        115                 120                 125

Asp Lys Gly Lys Val Val Ala Gly Val Ser Arg Val Asp Arg Asn Ser
    130                 135                 140

Ser Gly Arg Leu Asp Ala Val Leu Cys Val Leu Val Asp Asp Cys Gln
145                 150                 155                 160

Ile His Ile Leu Lys Met Phe His Leu Ser Ser Phe Val Ser Phe Val
                165                 170                 175

Cys

<210> SEQ ID NO 67
<211> LENGTH: 216
<212> TYPE: PRT
<213> ORGANISM: Oryctolagus cuniculus
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid

<400> SEQUENCE: 67

Val Val Thr Val Thr Ile Asn Cys Gln Ala Ser Glu Ser Val Tyr Ser
1               5                   10                  15

Asn Asn Arg Leu Ser Trp Phe Gln Gln Lys Pro Gly Gln Pro Pro Lys
            20                  25                  30

Leu Leu Ile Tyr Leu Val Ser Thr Leu Ala Ser Gly Val Pro Ser Arg
        35                  40                  45

Phe Lys Gly Ser Gly Ser Gly Thr Gln Phe Thr Leu Thr Ile Ser Asp
50                  55                  60
```

```
Val Val Cys Asp Asp Ala Ala Thr Tyr Tyr Cys Val Gly Tyr Lys Ser
 65                  70                  75                  80

Ser Thr Thr Asp Gly Leu Ala Phe Gly Gly Thr Glu Gly Met Val
                 85                  90                  95

Lys Lys Ser Gly Gly Gly Ala Leu Met Pro Tyr Gly Xaa Ser Gly Arg
            100                 105                 110

Ile Val Thr Leu Thr Val Gln Asp Arg Ala Gly His Ala Asp Asp Lys
            115                 120                 125

Gly His Ala Val Ala Leu Ala Ala Val Gly Ser Xaa Asp Pro Asp
130                 135                 140

Ser Ala Lys Asp Gly Asn Ser Ala Leu Val Ile Leu Arg Arg Lys Asp
145                 150                 155                 160

Arg Ser Leu Ser Xaa Asp Val Arg Arg Leu His Arg Val Leu Asp Ser
                165                 170                 175

Val Thr Thr Arg Arg Pro Ala Arg Pro Ala Arg Pro His Pro Met Ser
            180                 185                 190

Leu Lys Ser Phe Pro Val Pro Thr Arg Leu Ala Tyr Ala Ala Val Asp
            195                 200                 205

Lys Ser Pro Cys Leu Leu His Gly
    210                 215

<210> SEQ ID NO 68
<211> LENGTH: 249
<212> TYPE: PRT
<213> ORGANISM: Oryctolagus cuniculus
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid

<400> SEQUENCE: 68

Val Val Asp Ser His His His Cys Gln Ala Ser Glu Ser Val Tyr Ser
  1               5                  10                  15

Asn Asn Arg Leu Ser Trp Phe Gln Gln Lys Pro Gly Gln Pro Pro Lys
             20                  25                  30

Leu Leu Ile Tyr Leu Val Ser Thr Leu Ala Ser Gly Val Pro Ser Arg
         35                  40                  45

Phe Lys Gly Ser Gly Ser Gly Thr Gln Phe Thr Leu Thr Ile Ser Asp
     50                  55                  60
```

```
Val Val Cys Asp Asp Ala Ala Thr Tyr Tyr Cys Val Gly Tyr Lys Ser
 65                  70                  75                  80

Ser Thr Thr Asp Gly Leu Ala Phe Gly Gly Thr Asp Gly Gly Ser
                 85                  90                  95

Xaa Lys Arg Met Arg Arg His Leu His Leu Leu Arg Leu Val Arg
                100                 105                 110

Gly Gly Tyr Leu Arg Lys Pro Asn Ile Thr Ser Trp Arg Leu Arg Thr
            115                 120                 125

Arg Val Val Leu Gly Ala Gly Leu Ser Pro Pro Ala Gln Asp Thr Ser
        130                 135                 140

Met Thr Thr Pro Met Leu His Leu Cys Ser Ser Ala Pro Asn Ala Leu
145                 150                 155                 160

Ile His Leu Leu Lys Val Ile Asp Met Xaa Lys Ala Arg Xaa Arg Tyr
                165                 170                 175

Thr Ala Cys Asn Thr Asn Arg Leu Ala His Ala Ala Ala Arg Ala Val
            180                 185                 190

Thr Ser Xaa Xaa Leu Ser Asp Thr Val Leu Arg Pro Xaa Leu Ser Xaa
        195                 200                 205

Arg Gln Val Asn His Ala Ser Cys Glu Thr Glu Val His Asn Met Ile
210                 215                 220

Ala Thr Ser Thr Ser Gly Ser Val Arg Gly Gly Leu Arg Ala Gln Val
225                 230                 235                 240

Xaa Ile Gln Arg Cys Asn Pro Thr Cys
                245

<210> SEQ ID NO 69
<211> LENGTH: 126
<212> TYPE: PRT
<213> ORGANISM: Oryctolagus cuniculus
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid

<400> SEQUENCE: 69

Gln Met Gly Asp Ser His His His Cys Gln Ala Ser Glu Ser Val Tyr
 1               5                  10                  15

Ser Asn Asn Arg Leu Ser Trp Phe Gln Gln Lys Pro Gly Gln Pro Pro
                20                  25                  30

Lys Leu Leu Ile Tyr Leu Val Ser Thr Leu Ala Ser Gly Val Pro Ser
             35                  40                  45

Arg Phe Lys Gly Ser Gly Ser Gly Thr Gln Phe Thr Leu Thr Ile Ser
         50                  55                  60

Asp Val Val Cys Asp Asp Ala Ala Thr Tyr Tyr Cys Val Gly Tyr Lys
 65                  70                  75                  80

Ser Ser Thr Thr Asp Gly Leu Ala Phe Gly Gly Thr Glu Gly Trp
                 85                  90                  95

Ser Lys Lys Arg Val Pro Cys Gln Xaa Ser Pro Ala Gly Thr Lys Trp
            100                 105                 110

Ala His Arg Tyr Thr His Gln Xaa Gly Trp Arg Lys Cys Val
        115                 120                 125

<210> SEQ ID NO 70
<211> LENGTH: 165
```

```
<212> TYPE: PRT
<213> ORGANISM: Oryctolagus cuniculus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid

<400> SEQUENCE: 70

Phe Leu Trp Xaa Thr Val Thr Ile Asn Cys Gln Ala Ser Glu Ser Val
1               5                   10                  15

Tyr Ser Asn Asn Arg Leu Ser Trp Phe Gln Gln Lys Pro Gly Gln Pro
            20                  25                  30

Pro Lys Leu Leu Ile Tyr Leu Val Ser Thr Leu Ala Ser Gly Val Pro
        35                  40                  45

Ser Arg Phe Lys Gly Ser Gly Ser Gly Thr Gln Phe Thr Leu Thr Ile
    50                  55                  60

Ser Asp Val Val Cys Asp Asp Ala Ala Thr Tyr Tyr Cys Val Gly Tyr
65                  70                  75                  80

Lys Ser Ser Thr Thr Asp Gly Leu Ala Phe Gly Gly Gly Thr Glu Gly
                85                  90                  95

Gly Val Lys Lys Thr Cys Gly Leu Leu Phe Ile Gln Phe Gly Ser Lys
            100                 105                 110

Trp His His Leu Thr His Gln Thr Asn Val Xaa Met Leu Ile Val Ser
        115                 120                 125

Asn Thr Met Val Xaa Gly Gly Pro His Ser Glu Arg Lys Lys Arg
    130                 135                 140

Ala Xaa Gly Val Xaa Glu Gly Glu Trp Leu Phe His Xaa Pro Arg Lys
145                 150                 155                 160

Ala Ser Val Thr Xaa
                165

<210> SEQ ID NO 71
<211> LENGTH: 100
<212> TYPE: PRT
<213> ORGANISM: Oryctolagus cuniculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
```

<400> SEQUENCE: 71

Ser Xaa Trp Glu Thr Val Thr Ile Asn Cys Gln Ala Ser Glu Ser Val
1               5                   10                  15

Tyr Ser Asn Asn Arg Leu Ser Trp Phe Gln Gln Lys Pro Gly Gln Pro
            20                  25                  30

Pro Lys Leu Leu Ile Tyr Leu Val Ser Thr Leu Ala Ser Gly Val Pro
        35                  40                  45

Ser Arg Phe Lys Gly Ser Gly Ser Gly Thr Gln Phe Thr Leu Thr Ile
    50                  55                  60

Ser Asp Val Val Cys Asp Asp Ala Ala Thr Tyr Tyr Cys Val Gly Tyr
65                  70                  75                  80

Lys Ser Ser Thr Thr Asp Gly Leu Ala Phe Gly Gly Gly Thr Asp Gly
                85                  90                  95

Ile Ser Xaa Asn
            100

<210> SEQ ID NO 72
<211> LENGTH: 102
<212> TYPE: PRT
<213> ORGANISM: Oryctolagus cuniculus

<400> SEQUENCE: 72

Leu Val Leu Arg Gly Ala Ser His His His Cys Gln Ala Ser Glu Ser
1               5                   10                  15

Val Tyr Ser Asn Asn Arg Leu Ser Trp Phe Gln Gln Lys Pro Gly Gln
            20                  25                  30

Pro Pro Lys Leu Leu Ile Tyr Leu Val Ser Thr Leu Ala Ser Gly Val
        35                  40                  45

Pro Ser Arg Phe Lys Gly Ser Gly Ser Gly Thr Gln Phe Thr Leu Thr
    50                  55                  60

Ile Ser Asp Val Val Cys Asp Asp Ala Ala Thr Tyr Tyr Cys Val Gly
65                  70                  75                  80

Tyr Lys Ser Asn Thr Thr Asp Gly Leu Ala Phe Gly Gly Gly Thr Glu
                85                  90                  95

Val Val Val Lys Lys Asp
            100

<210> SEQ ID NO 73
<211> LENGTH: 104
<212> TYPE: PRT
<213> ORGANISM: Oryctolagus cuniculus
<220> FEATURE:
<221> NAME/KEY: misc_feature
<222> LOCATION: (5)..(5)
<223> OTHER INFORMATION: Xaa can be any naturally occurring amino acid

<400> SEQUENCE: 73

Pro Val Leu Trp Xaa Thr Val Thr Ile Asn Cys Gln Ala Ser Glu Ser
1               5                   10                  15

Val Tyr Ser Asn Asn Arg Leu Ser Trp Phe Gln Gln Lys Pro Gly Gln
            20                  25                  30

Pro Pro Lys Leu Leu Ile Tyr Leu Val Ser Thr Leu Ala Ser Gly Val
        35                  40                  45

Pro Ser Arg Phe Lys Gly Ser Gly Ser Gly Thr Gln Phe Thr Leu Thr
    50                  55                  60

Ile Ser Asp Val Val Cys Asp Asp Ala Ala Thr Tyr Tyr Cys Val Gly
65                  70                  75                  80

Tyr Lys Ser Ser Thr Thr Asp Gly Leu Ala Phe Gly Gly Thr Glu
                85                  90                  95

Gly Val Val Lys Lys Gly Ser Ala
            100

<210> SEQ ID NO 74
<211> LENGTH: 197
<212> TYPE: PRT
<213> ORGANISM: Oryctolagus cuniculus
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid

<400> SEQUENCE: 74

Thr Val Met Trp Xaa Ser Val Thr Ile Asn Cys Gln Ala Ser Glu Thr
1               5                   10                  15

Val Tyr Asn Asn Asp Arg Leu Ala Trp Phe Gln Gln Lys Pro Gly Gln
            20                  25                  30

Pro Pro Lys Leu Leu Ile Tyr Leu Ala Ser Thr Leu Pro Ser Gly Val
        35                  40                  45

Pro Ser Arg Phe Lys Gly Ser Gly Ser Gly Thr Gln Phe Thr Leu Thr
    50                  55                  60

Ile Ser Asp Val Gly Cys Asp Asp Ala Ala Thr Tyr Tyr Cys Val Gly
65                  70                  75                  80

Tyr Lys Ser Ser Thr Thr Asp Gly Leu Ala Phe Gly Gly Gly Thr Glu
                85                  90                  95

Gly Leu Val Lys Thr Thr Arg Cys Val Leu Leu Xaa Pro Thr Gln
            100                 105                 110

Xaa Xaa Val Ala Ala Ser Ser His Thr Xaa Lys Trp Xaa Glu Gly Thr
        115                 120                 125

Gly Val Gln Asn Leu Pro Leu Asn Arg Met Gly Pro Asp Xaa Glu Trp
    130                 135                 140

Lys Gln Met Arg Xaa Glu Gly Gly Lys Ala Leu Ala Phe Phe Leu Asn
145                 150                 155                 160

Arg Pro Gly Thr Phe Tyr Ile Xaa Lys Asn Ser Phe Thr Gly Asn Cys
                165                 170                 175

Asp Gly Glu Arg Asn Pro Pro Gly Thr Lys Leu Trp Arg Arg Glu Leu
            180                 185                 190

Gly Gly Pro Thr Gln
        195

<210> SEQ ID NO 75
<211> LENGTH: 178
<212> TYPE: PRT
<213> ORGANISM: Oryctolagus cuniculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (169)..(170)
<223> OTHER INFORMATION: Xaa can be any naturally occurring amino acid

<400> SEQUENCE: 75

Leu Trp Xaa Ser Val Thr Ile Asn Cys Gln Ala Ser Glu Thr Val Tyr
1               5                   10                  15

Asn Asn Asp Arg Leu Ala Trp Phe Gln Gln Lys Pro Gly Gln Pro Pro
            20                  25                  30

Lys Leu Leu Ile Tyr Leu Ala Ser Thr Leu Pro Ser Gly Val Pro Ser
        35                  40                  45

Arg Phe Lys Gly Ser Gly Ser Gly Thr Gln Phe Thr Leu Thr Ile Ser
50                  55                  60

Asp Val Gly Cys Asp Asp Ala Ala Thr Tyr Tyr Cys Val Gly Tyr Lys
65                  70                  75                  80

Ser Ser Thr Thr Asp Gly Leu Ala Phe Gly Gly Thr Glu Trp Gln
            85                  90                  95

Ile Leu Lys Gln Pro Cys Arg Arg Gly Glu Arg Trp Ser Cys Ser Asp
            100                 105                 110

Gly Glu Trp Gly Cys Gln Arg Ser Leu Ile Glu Glu Arg Leu Leu Xaa
        115                 120                 125

Arg Gly Asn Trp Arg Gly Lys Trp Val Ser His Leu Thr Gly Met Thr
130                 135                 140

Arg Ser Phe Leu Xaa Arg Gly Val Lys Cys Cys Asn Xaa Ser Ile Gly
145                 150                 155                 160

Lys Ile Thr Leu Arg Leu Xaa Ser Xaa Xaa Glu Ser Cys Arg Val Gly
            165                 170                 175

Ser Pro

<210> SEQ ID NO 76
<211> LENGTH: 195
<212> TYPE: PRT
<213> ORGANISM: Oryctolagus cuniculus

```
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid

<400> SEQUENCE: 76

Cys Leu Trp Gln Ser Val Thr Ile Asn Cys Gln Ala Ser Glu Thr Val
1               5                   10                  15

Tyr Asn Asn Asp Arg Leu Ala Trp Phe Gln Gln Lys Pro Gly Gln Pro
                20                  25                  30

Pro Lys Leu Leu Ile Tyr Leu Ala Ser Thr Leu Pro Ser Gly Val Pro
            35                  40                  45

Ser Arg Phe Lys Gly Ser Gly Ser Gly Thr Gln Phe Thr Leu Thr Ile
    50                  55                  60

Ser Asp Val Gly Cys Asp Ala Ala Thr Tyr Tyr Cys Val Gly Tyr
65                  70                  75                  80

Lys Ser Ser Thr Thr Asp Gly Leu Ala Phe Gly Gly Thr Asp Gly
                85                  90                  95

Val Val Lys Thr Ile Trp Ser Val Trp Gly Gly Leu Cys Ile Ile
                100                 105                 110

Leu Gly Ser Gly Val Thr Pro Gln Xaa Ser Leu Thr Gly Leu Met Pro
            115                 120                 125

Xaa Ser Xaa Gly Gly Asn Gly Leu Gly Arg Glu Cys Ala Arg Xaa His
    130                 135                 140

Glu Arg Lys Lys Lys Xaa Val His Arg His Cys Ile Val Trp Ser Gln
145                 150                 155                 160

Ala Gly Asp Leu Leu Tyr Asn Glu Ala Ile Pro Tyr Asp Arg Glu Val
                165                 170                 175

Gln Tyr Ala Pro Gly Gly Asn Cys Tyr Lys Arg Asn Leu Val Ser Lys
            180                 185                 190

Gln His His
        195

<210> SEQ ID NO 77
<211> LENGTH: 101
<212> TYPE: PRT
<213> ORGANISM: Oryctolagus cuniculus

<400> SEQUENCE: 77

Thr Val Gln Trp Glu Ser Val Thr Ile Asn Cys Gln Ala Ser Glu Thr
1               5                   10                  15

Val Tyr Asn Asn Asp Arg Leu Ala Trp Phe Gln Gln Lys Pro Gly Gln
                20                  25                  30

Pro Pro Lys Leu Leu Ile Tyr Leu Ala Ser Thr Leu Pro Ser Gly Val
            35                  40                  45
```

```
Pro Ser Arg Phe Lys Gly Ser Gly Ser Gly Thr Gln Phe Thr Leu Thr
    50                  55                  60

Ile Ser Asp Val Gly Cys Asp Ala Ala Thr Tyr Tyr Cys Val Gly
 65              70                  75                  80

Tyr Lys Ser Ser Thr Thr Asp Gly Leu Ala Phe Gly Gly Gly Thr Glu
                85                  90                  95

Gly Val Val Lys Lys
            100
```

```
<210> SEQ ID NO 78
<211> LENGTH: 125
<212> TYPE: PRT
<213> ORGANISM: Oryctolagus cuniculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid

<400> SEQUENCE: 78
```

```
Cys Ser Xaa Trp Glu Ser Val Thr Ile Asn Cys Gln Ala Ser Glu Thr
 1               5                  10                  15

Val Tyr Asn Asn Asp Arg Leu Pro Gly Phe Asn Arg Asn Gln Gly Ser
                20                  25                  30

Leu Pro Ser Ser Xaa Ser Ile Trp His Pro Leu Cys His Leu Gly Ser
            35                  40                  45

His Arg Asp Ser Lys Ala Val Asp Leu Gly His Ser Ser Leu Ser Pro
        50                  55                  60

Leu Val Met Trp Gly Val Met Met Leu Pro Leu Ile Ile Val Xaa Ala
 65              70                  75                  80

Ile Lys Val Val Arg Leu Met Val Trp Leu Ser Ala Glu Gly Pro Thr
                85                  90                  95

Ala Asp Pro Lys Thr Gly Val Xaa Gly Ser Arg Trp Glu Trp Gly Gln
            100                 105                 110

Gly Glu Arg Ser Gly Glu Thr Arg Leu Xaa Gly Gly Leu
        115                 120                 125
```

```
<210> SEQ ID NO 79
<211> LENGTH: 85
<212> TYPE: PRT
<213> ORGANISM: Oryctolagus cuniculus
<220> FEATURE:
<221> NAME/KEY: MISC_FEATURE
<222> LOCATION: (8)..(8)
<223> OTHER INFORMATION: Xaa at position 8 is glutamine or lysine
<220> FEATURE:
<221> NAME/KEY: MISC_FEATURE
<222> LOCATION: (22)..(22)
<223> OTHER INFORMATION: Xaa at position 22 is glycine or cysteine,
<220> FEATURE:
<221> NAME/KEY: misc_feature
```

```
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: Xaa at position 10 is tyrosnie or serine

<400> SEQUENCE: 79

Trp Val Leu Leu Ala Pro Cys Xaa Gly Leu Glu Trp Ile Gly Ser Ala
1               5                   10                  15

Gly Ala Tyr Cys Arg Ile Xaa Tyr Ala Ser Trp Ala Lys Ser Arg Ser
            20                  25                  30

Thr Ile Thr Arg Asn Thr Asn Leu Asn Thr Val Thr Leu Lys Met Thr
        35                  40                  45

Ser Leu Thr Xaa Ala Asp Thr Ala Thr Tyr Phe Cys Ala Arg Arg Ser
    50                  55                  60

Asp Val Gly Thr Ser Val Gly Phe Asp Ser Trp Gly Pro Gly Thr Leu
65              70                  75                  80

Val Thr Val Ser Leu
                85

<210> SEQ ID NO 80
<211> LENGTH: 92
<212> TYPE: PRT
<213> ORGANISM: Oryctolagus cuniculus

<400> SEQUENCE: 80

Asp Ser His His His Cys Gln Ala Ser Glu Ser Val Tyr Ser Asn Asn
1               5                   10                  15

Arg Leu Ser Trp Phe Gln Gln Lys Pro Gly Gln Pro Pro Lys Leu Leu
            20                  25                  30

Ile Tyr Leu Val Ser Thr Leu Ala Ser Gly Val Pro Ser Arg Phe Lys
        35                  40                  45

Gly Ser Gly Ser Gly Thr Gln Phe Thr Leu Thr Ile Ser Asp Val Val
    50                  55                  60

Cys Asp Asp Ala Ala Thr Tyr Tyr Cys Val Gly Tyr Lys Ser Ser Thr
65              70                  75                  80

Thr Asp Gly Leu Ala Phe Gly Gly Gly Thr Asp Gly
                85                  90

<210> SEQ ID NO 81
<211> LENGTH: 90
<212> TYPE: PRT
<213> ORGANISM: Oryctolagus cuniculus

<400> SEQUENCE: 81

Thr Val Thr Ile Asn Cys Gln Ala Ser Glu Ser Val Tyr Ser Asn Asn
1               5                   10                  15

Arg Leu Ser Trp Phe Gln Gln Lys Pro Gly Gln Pro Pro Lys Leu Leu
            20                  25                  30

Ile Tyr Leu Val Ser Thr Leu Ala Ser Gly Val Pro Ser Arg Phe Lys
        35                  40                  45

Gly Ser Gly Ser Gly Thr Gln Phe Thr Leu Thr Ile Ser Asp Val Val
    50                  55                  60

Cys Asp Asp Ala Ala Thr Tyr Tyr Cys Val Gly Tyr Lys Ser Ser Thr
65              70                  75                  80

Thr Asp Gly Leu Ala Phe Gly Gly Gly Thr
                85                  90
```

```
<210> SEQ ID NO 82
<211> LENGTH: 59
<212> TYPE: PRT
<213> ORGANISM: Oryctolagus cuniculus

<400> SEQUENCE: 82

Gly Thr Leu Val Thr Val Ser Ser Thr Ile Thr Arg Asn Thr Asn Leu
1               5                   10                  15

Asn Thr Val Thr Leu Lys Met Thr Ser Leu Thr Ala Ala Asp Thr Ala
            20                  25                  30

Thr Tyr Phe Cys Ala Arg Arg Ser Asp Val Gly Thr Ser Val Gly Phe
        35                  40                  45

Asp Ser Trp Gly Pro Gly Thr Leu Ala Pro Ser
    50                  55
```